(12) United States Patent
Yeh et al.

(10) Patent No.: US 10,485,980 B2
(45) Date of Patent: Nov. 26, 2019

(54) MIDFIELD TRANSMITTER AND RECEIVER SYSTEMS

(71) Applicant: NeuSpera Medical Inc., San Jose, CA (US)

(72) Inventors: Alexander Yeh, Los Altos Hills, CA (US); Timothy A. Fayram, Gilroy, CA (US); Elia Junco, Palo Alto, CA (US)

(73) Assignee: NeuSpera Medical Inc., San Jose, CA (US)

(*) Notice: Subject to any disclaimer, the term of this patent is extended or adjusted under 35 U.S.C. 154(b) by 0 days.

(21) Appl. No.: 16/004,894

(22) Filed: Jun. 11, 2018

(65) Prior Publication Data

US 2018/0289971 A1 Oct. 11, 2018

Related U.S. Application Data

(63) Continuation of application No. PCT/US2018/016051, filed on Jan. 30, 2018.

(Continued)

(51) Int. Cl.
*A61N 1/372* (2006.01)
*A61N 1/375* (2006.01)
(Continued)

(52) U.S. Cl.
CPC ........ *A61N 1/37229* (2013.01); *A61B 5/0015* (2013.01); *A61B 5/0031* (2013.01); *A61B 5/0205* (2013.01); *A61B 5/686* (2013.01); *A61B 17/3468* (2013.01); *A61N 1/025* (2013.01); *A61N 1/0558* (2013.01); *A61N 1/36* (2013.01); *A61N 1/36125* (2013.01); *A61N 1/372* (2013.01); *A61N 1/3754* (2013.01); *A61N 1/37205* (2013.01); *A61B* 17/1128 (2013.01); *A61B 2560/0219* (2013.01); *A61N 1/326* (2013.01); *A61N 1/3601* (2013.01); *A61N 1/36002* (2017.08); *A61N 1/36007* (2013.01);
(Continued)

(58) Field of Classification Search
CPC ...... A61N 1/37229; A61N 1/025; A61N 1/36; A61N 1/36125; A61N 1/372; A61N 1/37205; A61N 1/3754; A61B 5/0015; A61B 5/0031; A61B 5/686; A61B 17/3468
See application file for complete search history.

(56) References Cited

U.S. PATENT DOCUMENTS

| | | | |
|---|---|---|---|
| 2008/0269740 A1 | 10/2008 | Bonde et al. | |
| 2014/0036409 A1* | 2/2014 | Stevenson | A61N 1/3754 361/302 |
| 2016/0344238 A1 | 11/2016 | Yeh et al. | |

FOREIGN PATENT DOCUMENTS

WO  WO-2018140983 A1  8/2015

OTHER PUBLICATIONS

"International Application Serial No. PCT/US2018/016051, International Search Report dated May 10, 2018", 5 pgs.

(Continued)

*Primary Examiner* — Paula J Stice
(74) *Attorney, Agent, or Firm* — Schwegman Lundberg & Woessner, P.A.

(57) ABSTRACT

Generally discussed herein are systems, devices, and methods for providing a therapy (e.g., stimulation) and/or data signal using an implantable device. Systems, devices and methods for interacting with (e.g., communicating with, receiving power from) an external device are also provided.

18 Claims, 54 Drawing Sheets

Related U.S. Application Data

(60) Provisional application No. 62/598,855, filed on Dec. 14, 2017, provisional application No. 62/562,023, filed on Sep. 22, 2017, provisional application No. 62/515,220, filed on Jun. 5, 2017, provisional application No. 62/512,560, filed on May 30, 2017, provisional application No. 62/511,075, filed on May 25, 2017, provisional application No. 62/452,052, filed on Jan. 30, 2017.

(51) Int. Cl.
*A61N 1/02* (2006.01)
*A61N 1/05* (2006.01)
*A61N 1/36* (2006.01)
*A61B 17/34* (2006.01)
*A61B 5/00* (2006.01)
*A61B 5/0205* (2006.01)
*A61B 17/11* (2006.01)
*A61N 1/32* (2006.01)
*H02J 50/12* (2016.01)

(52) U.S. Cl.
CPC ...... *A61N 1/36071* (2013.01); *A61N 1/36107* (2013.01); *A61N 1/36117* (2013.01); *H02J 50/12* (2016.02)

(56) References Cited

OTHER PUBLICATIONS

"International Application Serial No. PCT/US2018/016051, Invitation to Pay Add'l Fees and Partial Search Rpt dated Mar. 23, 2018", 2 pgs.

"International Application Serial No. PCT/US2018/016051, Written Opinion dated May 10, 2018", 7 pgs.

\* cited by examiner

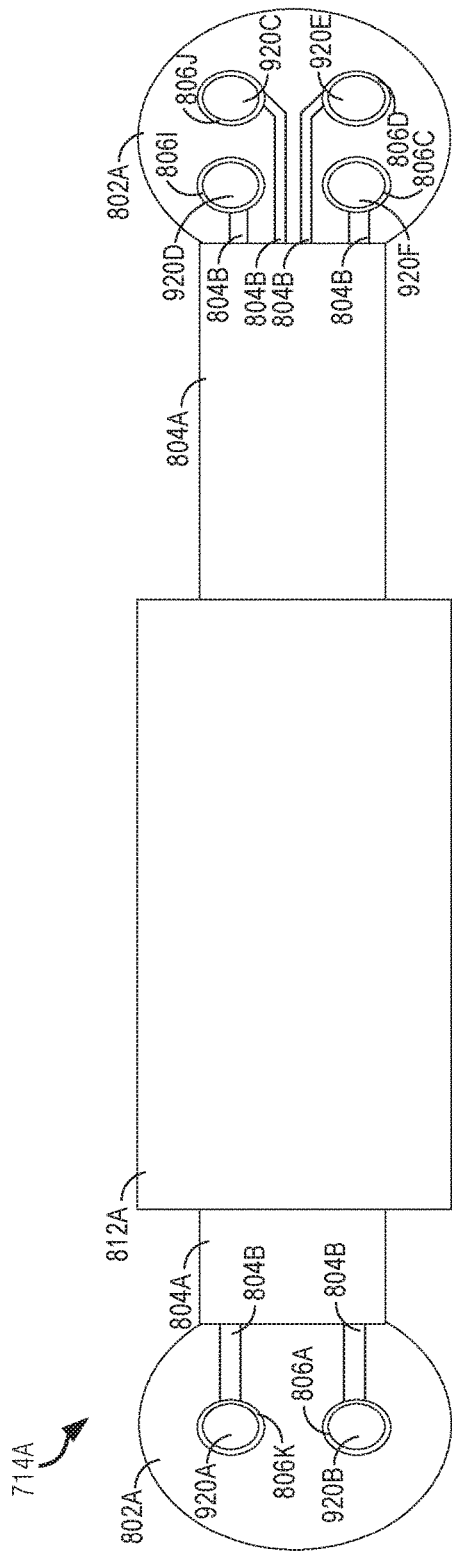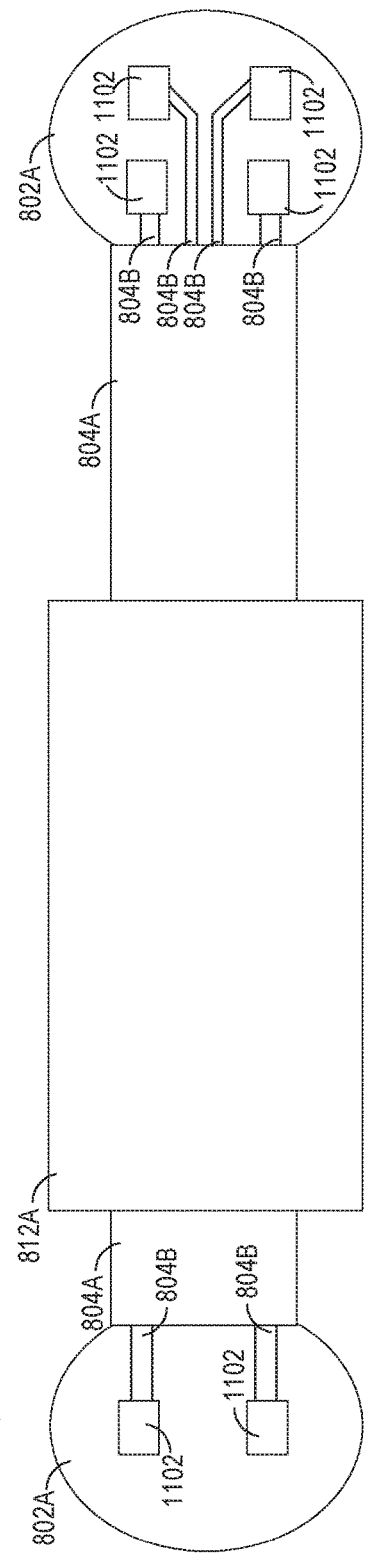

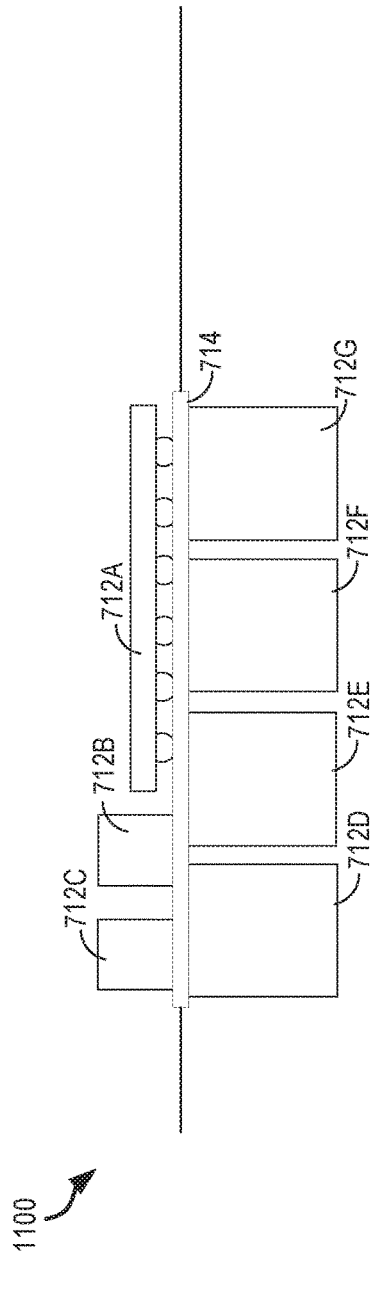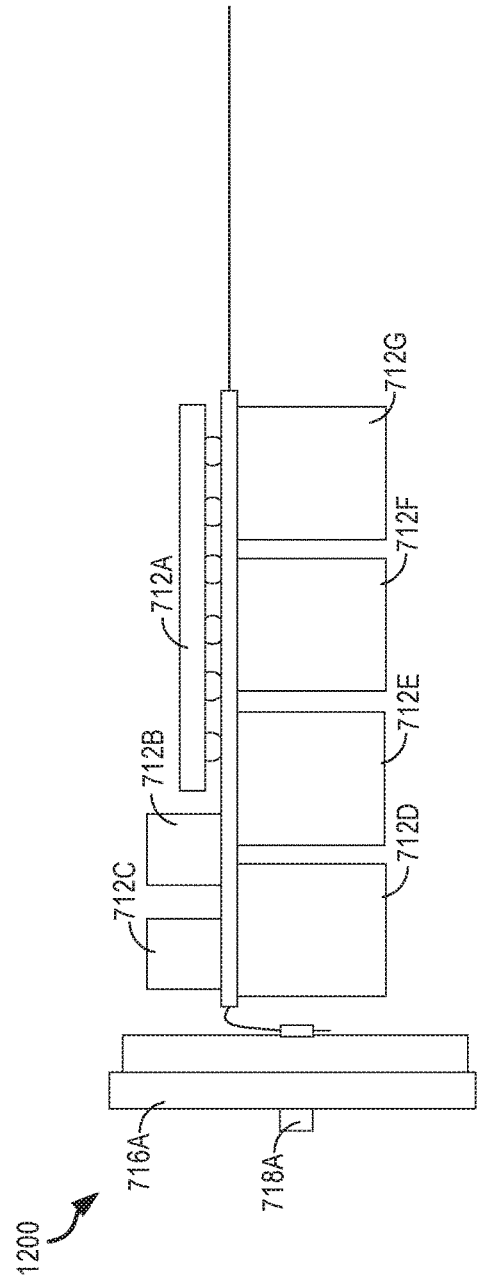

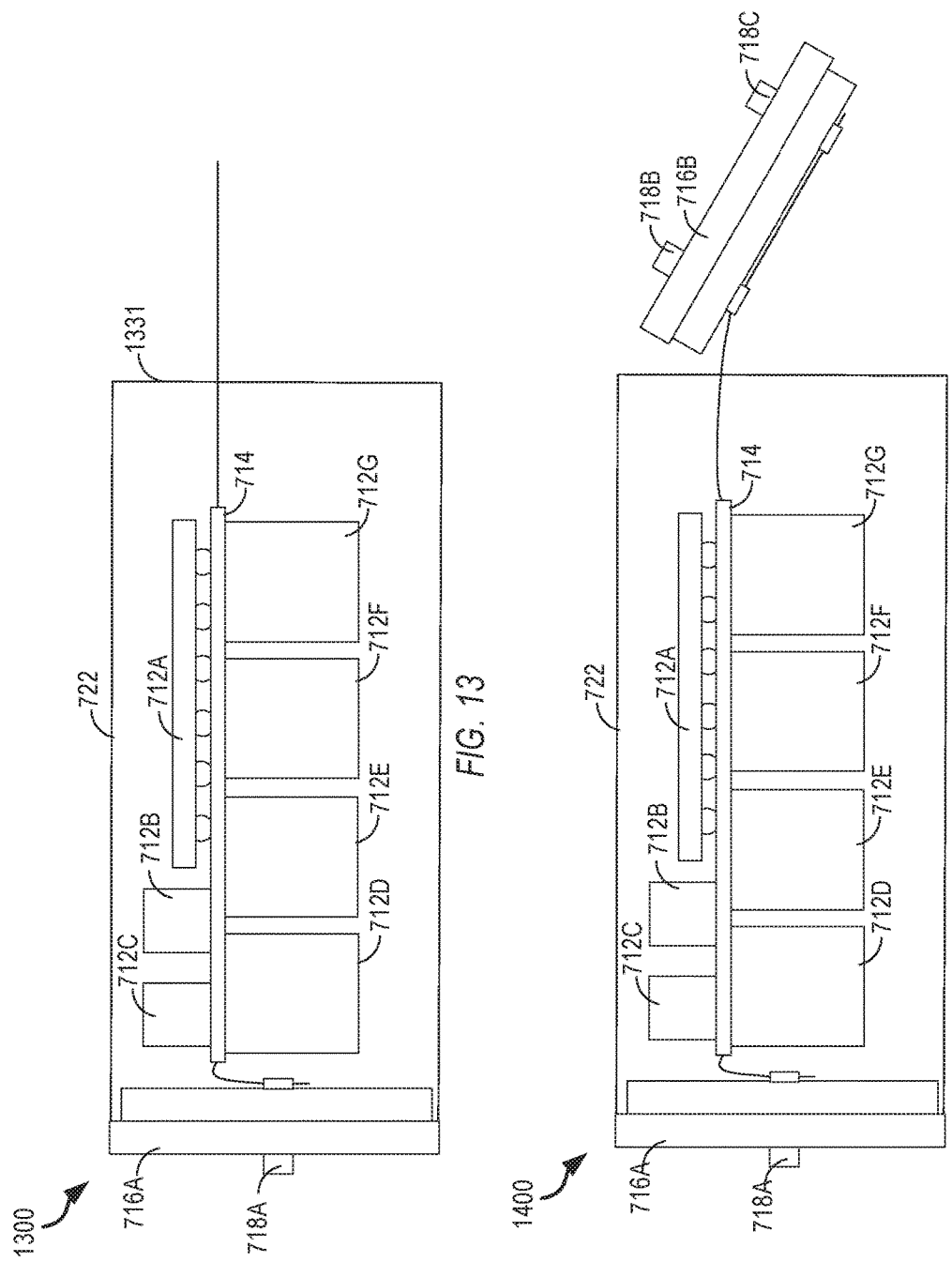

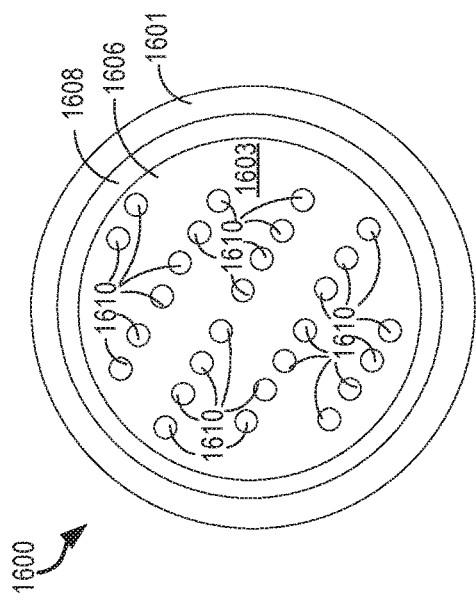
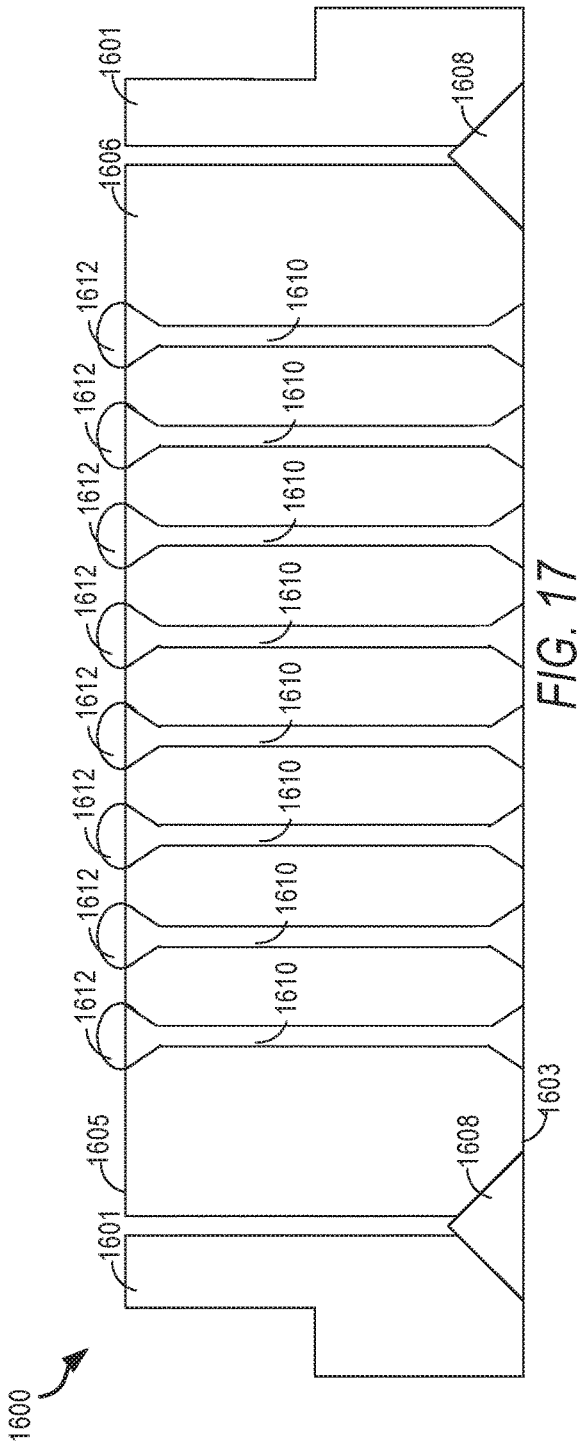

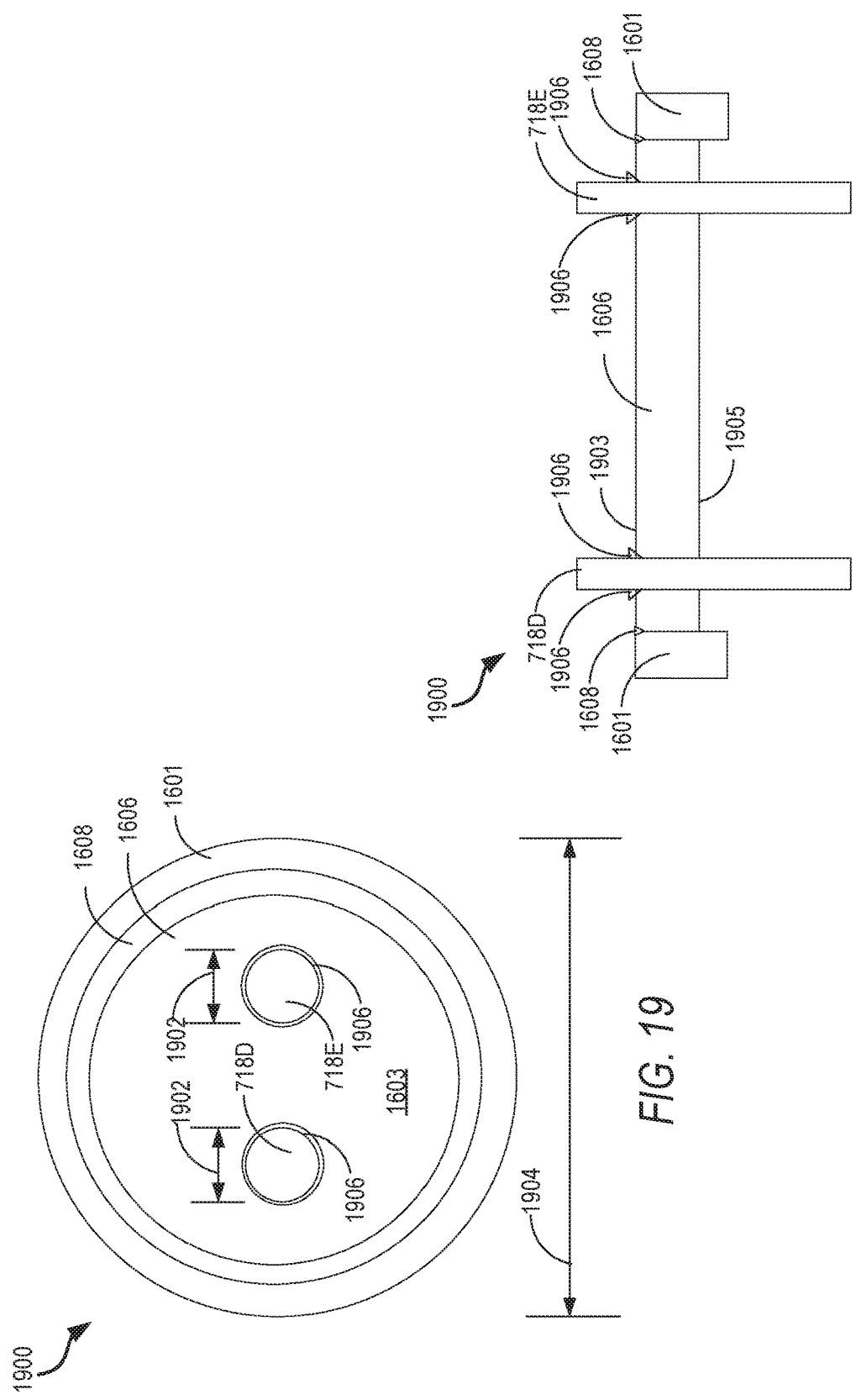

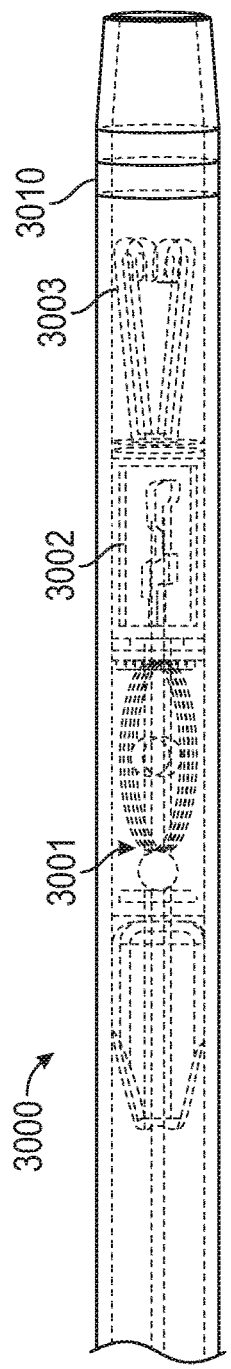
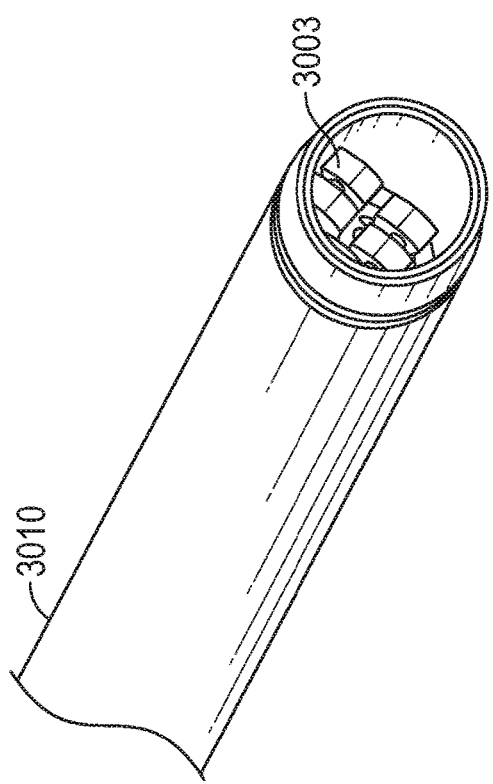
FIG. 30A
FIG. 30B

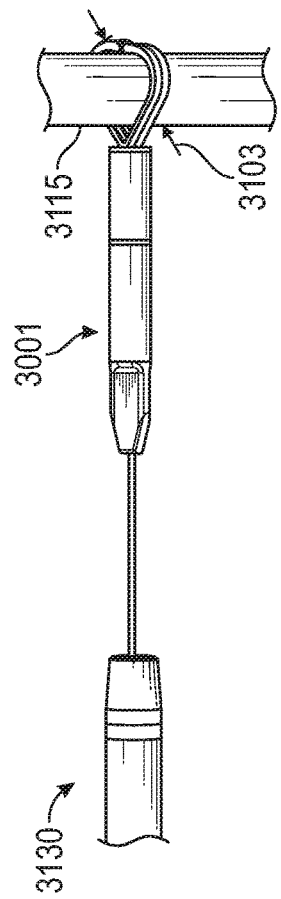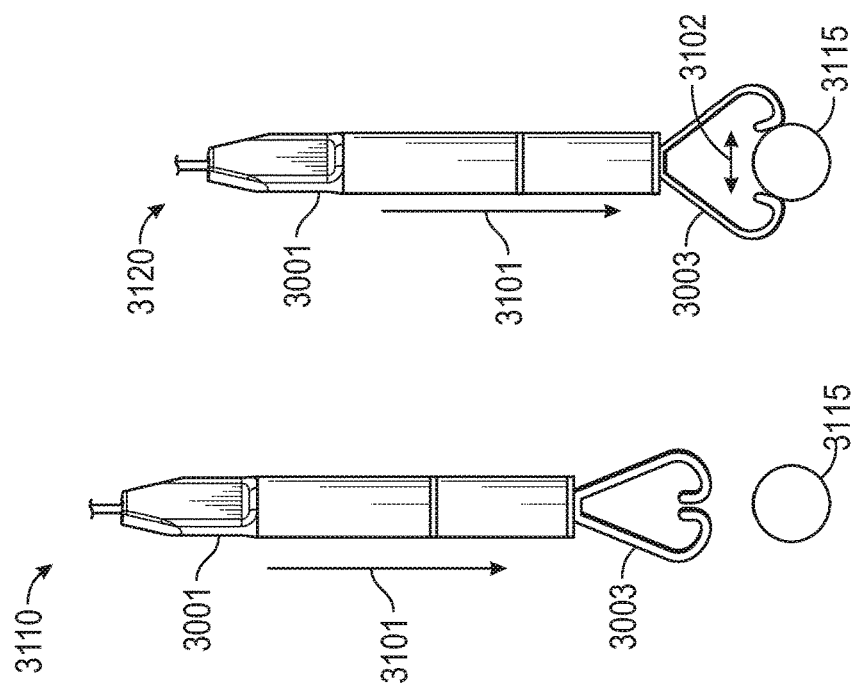
FIG. 31C
FIG. 31B
FIG. 31A

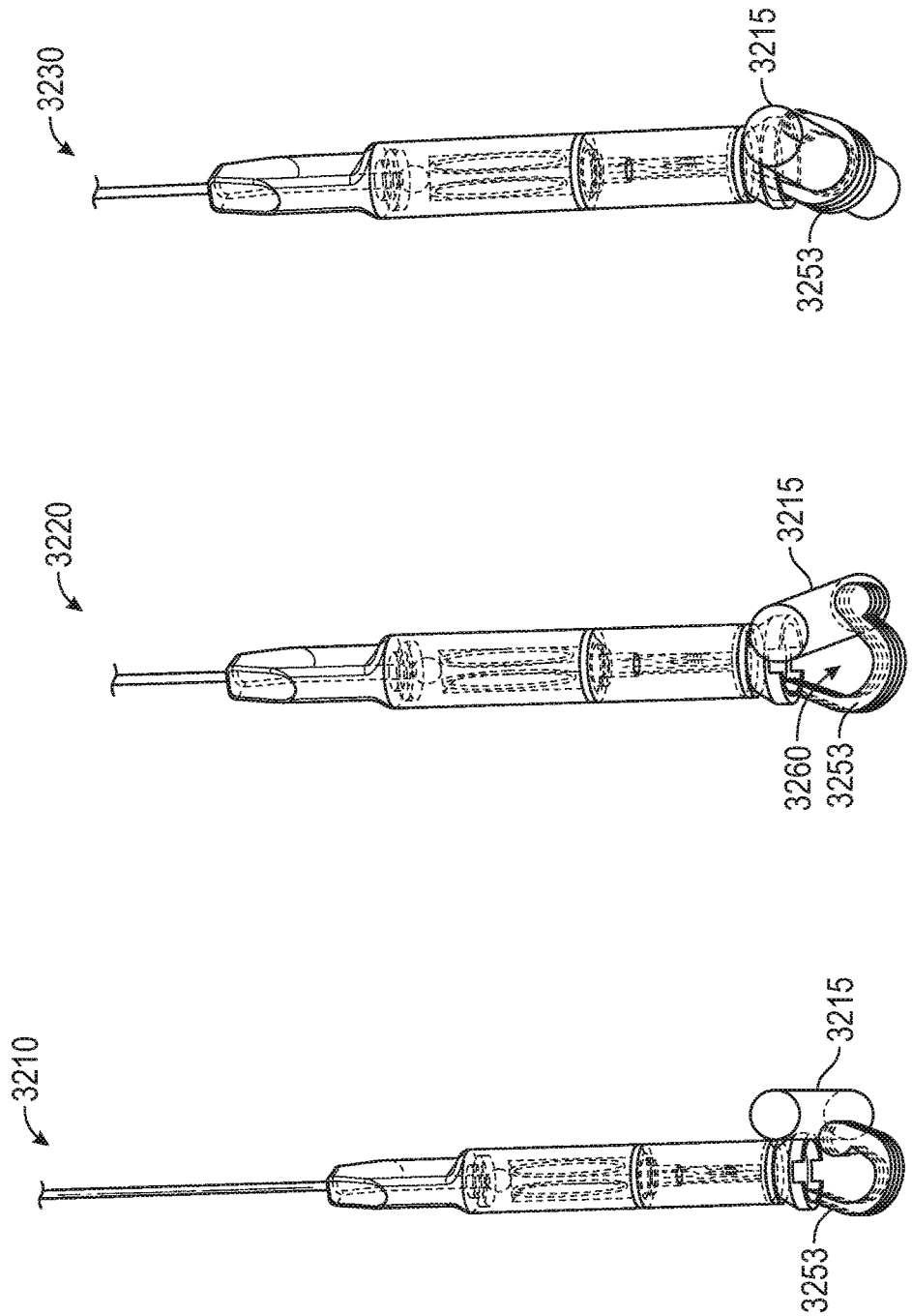

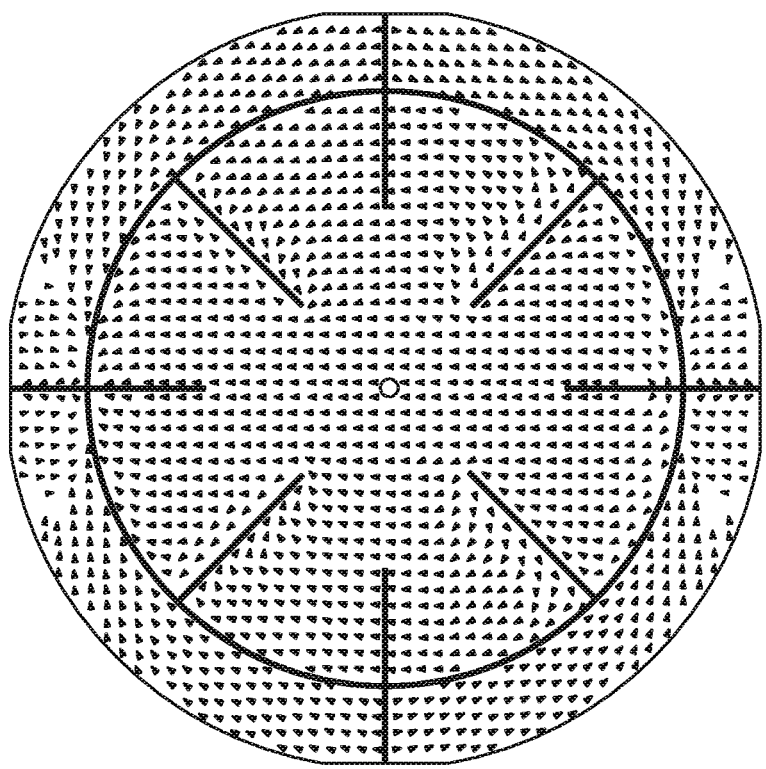
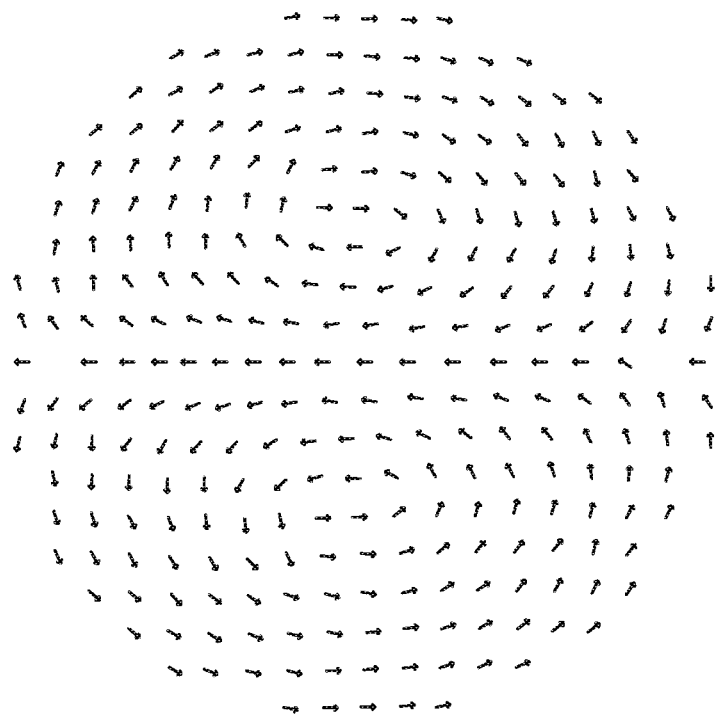
FIG. 75

MIDFIELD TRANSMITTER AND RECEIVER SYSTEMS

RELATED APPLICATIONS

This application is a Continuation of PCT Patent Application Number PCT/US2018/016051, filed on Jan. 30, 2018, which is herein incorporated by reference in its entirety and which claims the benefit of priority of the following U.S. Provisional Application No. 62/452,052 filed Jan. 30, 2017, and titled "Circuitry Housing Assembly"; U.S. Provisional Application No. 62/511,075 filed May 25, 2017, and titled "Injectable Nerve-wrapping Electrode"; U.S. Provisional Application No. 62/515,220 filed Jun. 5, 2017, and titled "Elongated Implantable Devices"; U.S. Provisional Application No. 62/512,560 filed May 30, 2017, and titled "Midfield Device Deployed in Arterial System"; U.S. Provisional Application No. 62/562,023 filed Sep. 22, 2017, and titled "Midfield Device Deployable Inside Vasculature"; and U.S. Provisional Application No. 62/598,855, filed Dec. 14, 2017, and titled "Layered Midfield Transmitter with Dielectric Tuning". The entire content of each of the identified U.S. provisional applications is hereby incorporated by reference herein.

TECHNICAL FIELD

One or more examples discussed herein regard devices, systems, and methods for providing signals (e.g., wireless midfield signals) to an implantable device (e.g., stimulation device) using an external device (e.g., external midfield coupler or midfield power source). One or more examples discussed herein regard devices, systems, and methods for providing therapy (e.g., stimulation or other modulation) or diagnostics from an implantable device. One or more examples discussed herein regard configurations for the implantable device and the external device. One or more examples discussed herein regard communicating data from the implantable device to the external device. One or more examples discussed herein regard devices, systems, and methods for positioning the implantable device at or near a specific location and/or shaping the implantable device.

TECHNICAL BACKGROUND

Various wireless powering methods for implantable electronics are based on nearfield or farfield coupling. These and other methods suffer from several disadvantages. A power harvesting structure in an implanted device is typically large (e.g., typically on the order of a centimeter or larger). Coils external to the body in nearfield coupling can similarly be bulky and inflexible. Such constraints present difficulties regarding incorporation of an external device into a patient's daily life. Furthermore, the intrinsic exponential decay of nearfield signals limits miniaturization of an implanted device beyond superficial depths (e.g., greater than 1 cm). On the other hand, the radiative nature of farfield signals can limit energy transfer efficiency.

Generally discussed herein are systems, devices, and methods for providing or delivering a patient therapy using an implantable device. In an example, the patient therapy includes an electrostimulation therapy provided to one or more neural targets in a patient body. In an example, the electrostimulation therapy is provided using an implantable device that wirelessly receives power and data signals from a midfield transmitter.

Wireless midfield powering technology can be used to provide power from an external power source to an implanted electrostimulation device. The external power source, or transmitter, can be located on or near a tissue surface, such as at an external surface of a patient's skin. Midfield-based devices can have various advantages over conventional implantable devices. For example, midfield powering technology need not require a relatively large implanted pulse generator and one or more leads that electrically connect the pulse generator to stimulation electrodes. A midfield device can provide a simpler implant procedure, which can lead to a lower cost and a lower risk of infection or other implant complications.

Another advantage of using midfield powering technology includes a battery or power source that can be provided externally to the patient, and thus the low power consumption and high efficiency circuit requirements of battery-powered implantable devices can be relaxed. Another advantage of using midfield powering technology can include an implanted device that can be physically smaller than a battery-powered device. Thus, midfield powering technology can help enable better patient tolerance and comfort along with potentially lower manufacturing and implantation costs.

There is a current unmet need that includes communicating power and/or data using midfield transmitters and receivers, such as to communicate power and/or data from an external midfield transmitter to or from an implanted device, such as a neural stimulation device or a sensor device.

SUMMARY

Although considerable progress has been made in the realm of medical device therapy, a need exists for therapy devices that provide stimulation or other therapy to targeted locations within a body. A need further exists for efficient, wireless power and data communication with an implanted therapy delivery device and/or an implanted diagnostic (e.g., sensor) device.

In accordance with several embodiments, an implantable system can include an elongate structure configured for implantation in a patient body using a catheter. The system can include an elongate circuit board assembly including, in order along its lengthwise direction, a proximal portion, a first flexible portion, a central portion, a second flexible portion, and a distal portion, and a hermetic enclosure configured to enclose the elongate circuit board assembly. In an example, the hermetic enclosure includes a first end cap with a conductive first feedthrough coupled to a conductor on the proximal portion of the elongate circuit board assembly, and a second end cap with a conductive second feedthrough coupled to a conductor on the distal portion of the elongate circuit board assembly. In an example, the first and second flexible portions have different length characteristics.

Various elongate midfield devices can be provided. In an example, such an elongate device can include at least one antenna configured to wirelessly receive power signals from an external device, a first circuitry housing including first circuitry therein coupled to the antenna, and a second circuitry housing including second circuitry therein. The elongate device can include an elongated portion between the first circuitry housing and the second circuitry housing, the elongated portion including one or more conductors extending therethrough and electrically coupling the first circuitry and the second circuitry. The elongate device can further include a body portion coupled to the second circuitry housing, and one or more electrodes exposed on, or at least partially in, the body portion.

In an example, an electrode system can be deployable inside of a patient body at a neural target using a cannula. Such an electrode system can include or use an elongated assembly body configured to house electrostimulation circuitry or sense circuitry, and an electrode assembly coupled to the electrostimulation circuitry or sense circuitry and configured to provide electrostimulation to, or sense electrical signal activity from, the neural target inside of the patient body. In an example, the electrode assembly includes multiple elongate members that extend away from the assembly body in a predominately longitudinal direction, and the electrode assembly can have a retracted first configuration when the electrode assembly is inside of the cannula, and an expanded second configuration when the electrode assembly is outside of the cannula. In an example, the electrode assembly has a further expanded third configuration while the electrode assembly receives the neural target.

In an example, an electrostimulation and/or sensor system can be provided for implantation inside of a blood vessel of a patient. Such a system can include or use a wireless receiver circuit configured to receive a wireless power and/or data signal from a source device external to the patient, and an expandable and contractible support structure having a first contracted configuration inside of a delivery catheter and having a second expanded configuration outside of the delivery catheter. In an example, the support structure is coupled to the wireless receiver circuit.

In an example, a midfield transmitter can include a layered structure, such as can include at least a first conductive plane provided on a first layer of the transmitter, one or more microstrips provided on a second layer of the transmitter, and a third conductive plane provided on a third layer of the transmitter, the third conductive plane electrically coupled to the first conductive plane using one or more vias that extend through the second layer. In an example, the midfield transmitter can include a first dielectric member interposed between the first and second conductive planes, and a different second dielectric member interposed between the second and third conductive planes.

This Summary is intended to provide an overview of subject matter of the present application. It is not intended to provide an exclusive or exhaustive explanation of the invention or inventions discussed herein. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 9 illustrates generally a top view diagram of an embodiment of a circuit board.

FIG. 10 illustrates generally a top view diagram of an embodiment of a circuit board.

FIG. 11 illustrates generally an embodiment of a device that includes various electrical and/or electronic components coupled to a circuit board.

FIG. 12 illustrates generally an embodiment of a device that includes various components coupled to a circuit board and the circuit board coupled to a first end cap.

FIG. 13 illustrates generally an embodiment of a device that includes a circuit board coupled to a first end cap and disposed in an enclosure.

FIG. 14 illustrates generally an embodiment of a device that includes a circuit board coupled to first and second end caps and disposed in an enclosure.

FIG. 16 illustrates generally an example of a top view of an end cap.

FIG. 17 illustrates generally an example of a cross-section view of the end cap from FIG. 16.

FIG. 19 illustrates generally an example of a top view of a dual-port cap.

FIG. 20 illustrates generally an example that includes a cross-section view of the dual-port cap from FIG. 19.

FIGS. 30A and 30B illustrate generally different views of an example of an implantable electrode assembly inside of a cannula.

FIG. 31A illustrates generally a first example of an implantable electrode assembly approaching a neural target.

FIG. 31B illustrates generally a second example of an implantable electrode assembly with nerve-wrapping electrodes flexing away from a neural target.

FIG. 31C illustrates generally a third example of an implantable electrode assembly with nerve-wrapping electrodes provided about a neural target.

FIGS. 32A, 32B, and 32C illustrate generally examples of using a flexible electrode configuration to receive and retain a neural target.

FIG. 75 illustrates generally an example that shows surface currents that result when a midfield transmitter is excited.

DETAILED DESCRIPTION

Figure 1:
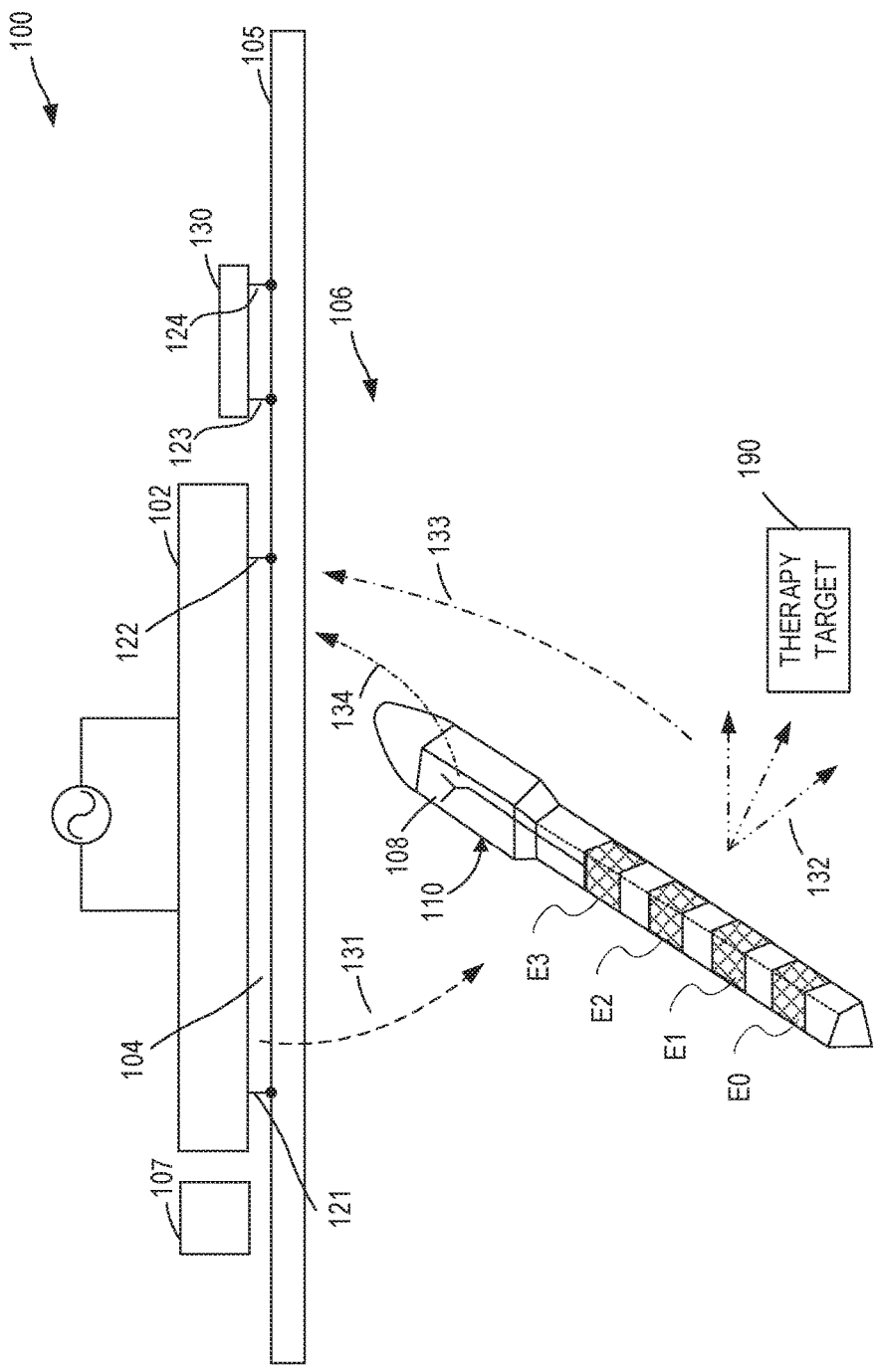
FIG. 1 illustrates generally a schematic of an embodiment of a system using wireless communication paths.

In the following description that includes examples of different nerve-electrode interfaces, reference is made to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. The present inventors contemplate examples using any combination or permutation of those elements shown or described (or one or more aspects thereof), either with respect to a particular example (or one or more aspects thereof), or with respect to other examples (or one or more aspects thereof) shown or described herein. Generally discussed herein are implantable devices and methods of assembling the implantable devices.

I. Implantable Systems and Devices

Section headings herein, like the one above ("IMPLANTABLE SYSTEMS AND DEVICES"), are provided to guide a reader generally to material corresponding to the topic indicated by the heading. However, discussions under a particular heading are not to be construed as applying only to configurations of a single type; instead, the various features discussed in the various sections or subsections herein can be combined in various ways and permutations. For example, some discussion of features and benefits of implantable systems and devices may be found in the text and corresponding figures under the present section heading "IMPLANTABLE SYSTEMS AND DEVICES".

Midfield powering technology can provide power to a deeply implanted electrostimulation device from an external power source located on or near a tissue surface, such as at an external surface of a user's skin. The user can be a clinical patient or other user. The midfield powering technology can have one or more advantages over implantable pulse generators. For example, a pulse generator can have one or more relatively large, implanted batteries and/or one or more lead systems. Midfield devices, in contrast, can include relatively small battery cells that can be configured to receive and store relatively small amounts of power. A midfield device can include one or more electrodes integrated in a unitary implantable package. Thus, in some examples, a midfield-powered device can provide a simpler implant procedure over other conventional devices, which can lead to a lower cost and a lower risk of infection or other implant complications. One or more of the advantages can be from an amount of power transferred to the implanted device. The ability to focus the energy from the midfield device can allow for an increase in the amount of power transferred to the implanted device.

An advantage of using midfield powering technology can include a main battery or power source being provided externally to the patient, and thus low power consumption and high efficiency circuitry requirements of conventional battery-powered implantable devices can be relaxed. Another advantage of using midfield powering technology can include an implanted device that can be physically smaller than a battery-powered device. Midfield powering technology can thus help enable better patient tolerance and comfort along with potentially lower costs to manufacture and/or to implant in patient tissue.

There is a current unmet need that includes communicating power and/or data using midfield transmitters and receivers, such as to communicate power and/or data from an external midfield coupler or source device to one or more implanted neural stimulation devices and/or one or more implanted sensor devices. The unmet need can further include communicating data from the one or more implanted neural stimulation devices and implanted sensor devices to the external midfield coupler or source device.

In one or more examples, multiple devices can be implanted in patient tissue and can be configured to deliver a therapy and/or sense physiologic information about a patient and/or about the therapy. The multiple implanted devices can be configured to communicate with one or more external devices. In one or more examples, the one or more external devices are configured to provide power and/or data signals to the multiple implanted devices, such as concurrently or in a time-multiplexed (e.g., "round-robin") fashion. The provided power and/or data signals can be steered or directed by an external device to transfer the signals to an implant efficiently. Although the present disclosure may refer to a power signal or data signal specifically, such references are to be generally understood as optionally including one or both of power and data signals.

Several embodiments described herein can be advantageous because they include one, several, or all of the following benefits: (i) a system configured to (a) communicate power and/or data signals from a midfield coupler device to an implantable device via midfield radiofrequency (RF) signals, (b) generate and provide a therapy signal via one or more electrodes coupled to the implantable device, the therapy signal including an information component, and producing a signal incident to providing the therapy signal, (c) receive a signal, based on the therapy signal, using electrodes coupled to the midfield coupler device, and (d) at the midfield coupler device or another device, decode and react to the information component from the received signal; (ii) a dynamically configurable, active midfield transceiver that is configured to provide RF signals to modulate an evanescent field at a tissue surface and thereby generate a propagating field within tissue, such as to transmit power and/or data signals to an implanted target device (see, e.g., the example of FIG. 74 that shows signal penetration inside tissue); (iii) an implantable device including an antenna configured to receive a midfield power signal from the midfield transceiver and including a therapy delivery circuitry configured to provide signal pulses to electrostimulation electrodes using a portion of the received midfield power signal, wherein the signal pulses include therapy pulses and data pulses, and the data pulses can be interleaved with or embedded in the therapy pulses; (iv) an implantable device configured to encode information, in a therapy signal, about the device itself, such as including information about the device's operating status, or about a previously-provided, concurrent, or planned future therapy provided by the device; (v) a midfield transceiver including electrodes that are configured to sense electrical signals at a tissue surface; and/or (vi) adjustable wireless signal sources and receivers that are configured together to enable a communication loop or feedback loop.

In one or more examples, one or more of these benefits and others can be realized using a system for manipulating an evanescent field at or near an external tissue surface to transmit power and/or data wirelessly to one or more target devices implanted in the tissue. In one or more examples, one or more of these benefits can be realized using a device or devices implanted in a body or capable of being implanted in a body and as described herein. In one or more examples, one or more of these benefits can be realized using a midfield powering and/or communication device (e.g., a transmitter device and/or a receiver device or a transceiver device).

A system can include a signal generator system adapted to provide multiple different sets of signals (e.g., RF signals). Each set can include two or more separate signals in some embodiments. The system can also include a midfield transmitter including multiple excitation ports, the midfield transmitter coupled to the RF signal generator system, and the midfield transmitter being adapted to transmit the multiple different sets of RF signals at respective different times via the excitation ports. The excitation ports can be adapted to receive respective ones of the separate signals from each set of RF signals. Each of the transmitted sets of RF signals can include a non-negligible magnetic field (H-field) component that is substantially parallel to the external tissue surface. In one or more examples, each set of transmitted RF signals is adapted or selected to differently manipulate an evanescent field at or near the tissue surface to transmit a power and/or data signal to one or more target devices implanted in the tissue via a midfield signal instead of via inductive nearfield coupling or radiative far-field transmission.

In one or more examples, one or more of the above-mentioned benefits, among others, can be realized, at least in part, using an implantable therapy delivery device (e.g., a device configured to provide neural stimulation) that includes receiver circuitry including an antenna (e.g., an electric-field or magnetic field based antenna) configured to receive a midfield power signal from an external source device, such as when the receiver circuitry is implanted within tissue. The implantable therapy delivery device can include therapy delivery circuitry. The therapy delivery circuitry can be coupled to the receiver circuitry. The therapy delivery circuitry can be configured to provide signal pulses to one or more energy delivery members (e.g., electrostimulation electrodes), which may be integrally coupled to a body of the therapy delivery device or positioned separately from (e.g., not located on) the body of the therapy delivery device), such as by using a portion of the received midfield power signal from the external source device (e.g., sometimes referred to herein as an external device, an external source, an external midfield device, a midfield transmitter device, a midfield coupler, a midfield powering device, a powering device, or the like, depending on the configuration and/or usage context of the device). The signal pulses can include one or more electrostimulation therapy pulses and/or data pulses. In one or more examples, one or more of the above-mentioned benefits, among others, can be realized, at least in part, using an external transmitter and/or receiver (e.g., transceiver) device that includes an electrode pair configured to be disposed at an external tissue surface, and the electrode pair is configured to receive an electrical signal via the tissue. The electrical signal can correspond to an electrostimulation therapy delivered to the tissue by the therapy delivery device. A demodulator circuitry can be coupled to the electrode pair and can be configured to demodulate a portion of the received electrical signal, such as to recover a data signal originated by the therapy delivery device.

In one or more examples that include using a midfield wireless coupler, tissue can act as a dielectric to tunnel energy. Coherent interference of propagating modes can confine a field at a focal plane to less than a corresponding vacuum wavelength, for example, with a spot size subject to a diffraction limit in a high-index material. In one or more examples, a receiver (e.g., implanted in tissue) positioned at such a high energy density region, can be one or more orders of magnitude smaller than a conventional nearfield implantable receiver, or can be implanted more deeply in tissue (e.g., greater than 1 cm in depth). In one or more examples, a transmitter source described herein can be configured to provide electromagnetic energy to various target locations, including for example to one or more deeply implanted devices. In an example, the energy can be provided to a location with greater than about a few millimeters of positioning accuracy. That is, a transmitted power or energy signal can be directed or focused to a target location that is within about one wavelength of the signal in tissue. Such energy focusing is substantially more accurate than the focusing available via traditional inductive means and is sufficient to provide adequate power to a receiver on a millimeter scale. In other wireless powering approaches using nearfield coupling (inductive coupling and its resonant enhanced derivatives), evanescent components outside tissue (e.g., near the source) remain evanescent inside tissue, which does not allow for effective depth penetration. Unlike nearfield coupling, energy from a midfield source is primarily carried in propagating modes and, as a result, an energy transport depth is limited by environmental losses rather than by intrinsic decay of the nearfield. Energy transfer implemented with these characteristics can be at least two to three orders of magnitude more efficient than nearfield systems.

One or more of the systems, apparatuses, and methods discussed herein can be used to help treat fecal or urinary incontinence (e.g., overactive bladder), such as by stimulating the tibial nerve or any branch of the tibial nerve, such as but not limited to the posterior tibial nerve, one or more nerves or nerve branches originating from the sacral plexus, including but not limited to S1-S4, the tibial nerve, and/or the pudendal nerve. Urinary incontinence may be treated by stimulating one or more of muscles of the pelvic floor, nerves innervating the muscles of the pelvic floor, internal urethral sphincter, external urethral sphincter, and the pudendal nerve or branches of the pudendal nerve.

One or more of the systems, apparatuses, and methods discussed herein can be used to help treat sleep apnea and/or snoring by stimulating one or more of a nerve or nerve branches of the hypoglossal nerve, the base of the tongue (muscle), phrenic nerve(s), intercostal nerve(s), accessory nerve(s), and cervical nerves C3-C6. Treating sleep apnea and/or snoring can include providing energy to an implant to sense a decrease, impairment, or cessation of breathing (such as by measuring oxygen saturation).

One or more of the systems, apparatuses, and methods discussed herein can be used to help treat vaginal dryness, such as by stimulating one or more of Bartholin gland(s), Skene's gland(s), and inner wall of vagina. One or more of the systems, apparatuses, and methods discussed herein can be used to help treat migraines or other headaches, such as by stimulating one or more of the occipital nerve, supraorbital nerve, C2 cervical nerve, or branches thereof, and the frontal nerve, or branches thereof. One or more of the systems, apparatuses, and methods discussed herein can be used to help treat post-traumatic stress disorder, hot flashes, and/or complex regional pain syndrome such as by stimulating one or more of the stellate ganglion and the C4-C7 of the sympathetic chain.

One or more of the systems, apparatuses, and methods discussed herein can be used to help treat neuralgia (e.g., trigeminal neuralgia), such as by stimulating one or more of the sphenopalatine ganglion nerve block, the trigeminal nerve, or branches of the trigeminal nerve. One or more of the systems, apparatuses, and methods discussed herein can be used to help treat dry mouth (e.g., caused by side effects from medications, chemotherapy or radiation therapy cancer treatments, Sjogren's disease, or by other cause of dry mouth), such as by stimulating one or more of Parotid glands, submandibular glands, sublingual glands, submucosa of the oral mucosa in the oral cavity within the tissue of the buccal, labial, and/or lingual mucosa, the soft palate, the lateral parts of the hard palate, and/or the floor of the mouth and/or between muscle fibers of the tongue, Von Ebner glands, glossopharyngeal nerve (CN IX), including branches of CN IX, including otic ganglion, a facial nerve (CN VII), including branches of CN VII, such as the submandibular ganglion, and branches of T1-T3, such as the superior cervical ganglion.

One or more of the systems, apparatuses, and methods discussed herein can be used to help treat a transected nerve, such as by sensing electrical output from the proximal portion of a transected nerve and delivering electrical input into the distal portion of a transected nerve, and/or sensing electrical output from the distal portion of a transected nerve and delivering electrical input into the proximal portion of a transected nerve. One or more of the systems, apparatuses, and methods discussed herein can be used to help treat cerebral palsy, such as by stimulating one or more muscles or one or more nerves innervation one or more muscles affected in a patient with cerebral palsy. One or more of the systems, apparatuses, and methods discussed herein can be used to help treat erectile dysfunction, such as by stimulating one or more of pelvic splanchnic nerves (S2-S4) or any branches thereof, the pudendal nerve, cavernous nerve(s), and inferior hypogastric plexus.

One or more of the systems, apparatuses, and methods discussed herein can be used to help treat menstrual pain, such as by stimulating one or more of the uterus and the vagina. One or more of the systems, apparatuses, and methods discussed herein can be used as an intrauterine device, such as by sensing one or more PH and blood flow or delivering current or drugs to aid in contraception, fertility, bleeding, or pain. One or more of the systems, apparatuses, and methods discussed herein can be used to incite human arousal, such as by stimulating female genitalia, including external and internal, including clitoris or other sensory active parts of the female, or by stimulating male genitalia.

One or more of the systems, apparatuses, and methods discussed herein can be used to help treat hypertension, such as by stimulating one or more of a carotid sinus, left or right cervical vagus nerve, or a branch of the vagus nerve. One or more of the systems, apparatuses, and methods discussed herein can be used to help treat paroxysmal supraventricular tachycardia, such as by stimulating one or more of trigeminal nerve or branches thereof, anterior ethmoidal nerve, and the vagus nerve. One or more of the systems, apparatuses, and methods discussed herein can be used to help treat vocal cord dysfunction, such as by sensing the activity of a vocal cord and the opposite vocal cord or just stimulating one or more of the vocal cords by stimulating nerves innervating the vocal cord, the left and/or Right recurrent laryngeal nerve, and the vagus nerve.

One or more of the systems, apparatuses, and methods discussed herein can be used to help repair tissue, such as by stimulating tissue to do one or more of enhancing microcirculation and protein synthesis to heal wounds and restoring integrity of connective and/or dermal tissues. One or more of the systems, apparatuses, and methods discussed herein can be used to help asthma or chronic obstructive pulmonary disease, such as by one or more of stimulating the vagus nerve or a branch thereof, blocking the release of norepinephrine and/or acetylcholine and/or interfering with receptors for norepinephrine and/or acetylcholine.

One or more of the systems, apparatuses, and methods discussed herein can be used to help treat cancer, such as by stimulating, to modulate one or more nerves near or in a tumor, such as to decrease the sympathetic innervation, such as epinephrine/NE release, and/or parasympathetic innervation, such as Ach. One or more of the systems, apparatuses, and methods discussed herein can be used to help treat diabetes, such as by powering a sensor inside the human body that detects parameters of diabetes, such as a glucose level or ketone level and using such sensor data to adjust delivery of exogenous insulin from an insulin pump. One or more of the systems, apparatuses, and methods discussed herein can be used to help treat diabetes, such as by powering a sensor inside the human body that detects parameters of diabetes, such as a glucose level or ketone level, and using a midfield coupler to stimulate the release of insulin from islet beta cells.

One or more of the systems, apparatuses, and methods discussed herein can be used to help treat neurological conditions, disorders or diseases (such as Parkinson's disease (e.g., by stimulating an internus or nucleus of the brain), Alzheimer's disease, Huntington's disease, dementia, Creutzfeldt-Jakob disease, epilepsy (e.g., by stimulating a left cervical vagus nerve or a trigeminal nerve), post-traumatic stress disorder (PTSD) (e.g., by stimulating a left cervical vagus nerve), or essential tremor, such as by stimulating a thalamus), neuralgia, depression, dystonia (e.g., by stimulating an internus or nucleus of the brain), phantom limb (e.g., by stimulating an amputated nerve, such an ending of an amputated nerve), dry eyes (e.g., by stimulating a lacrimal gland), arrhythmia (e.g., by stimulating the heart), a gastrointestinal disorder, such as obesity, gastroesophageal reflux, and/or gastroparesis, such as by stimulating a C1-C2 occipital nerve or deep brain stimulation (DBS) of the hypothalamus, an esophagus, a muscle near sphincter leading to the stomach, and/or a lower stomach, and/or stroke (e.g., by subdural stimulation of a motor cortex). Using one or more examples discussed herein, stimulation can be provided continuously, on demand (e.g., as demanded by a physician, patient, or other user), or periodically.

In providing the stimulation, an implantable device can be situated up to five centimeters or more below the surface of the skin. A midfield powering device is capable of delivering power to those depths in tissue. In one or more examples, an implantable device can be situated between about 2 centimeters and 4 centimeters, about 3 centimeters, between about 1 centimeter and five centimeters, less than 1 centimeter, about two centimeters, or other distance below the surface of the skin. The depth of implantation can depend on the use of the implanted device. For example, to treat depression, hypertension, epilepsy, and/or PTSD the implantable device can situated between about 2 centimeters and about four centimeters below the surface of the skin. In another example, to treat sleep apnea, arrhythmia (e.g., bradycardia), obesity, gastroesophageal reflux, and/or gastroparesis the implantable device can be situated at greater than about 3 centimeters below the surface of the skin. In yet another example, to treat Parkinson's, essential tremors, and/or dystonia the implantable device can be situated between about 1 centimeter and about 5 centimeters below the surface of the skin. Yet other examples include situating the implantable device between about 1 centimeter and about 2 centimeters below the surface of the skin, such as to treat fibromyalgia, stroke, and/or migraine, at about 2 centimeters to treat asthma, and at about one centimeter or less to treat dry eyes.

Although many embodiments included herein describe devices or methods for providing stimulation (e.g., electrostimulation), the embodiments may be adapted to provide other forms of modulation (e.g., denervation) in addition to or instead of stimulation. In addition, although many embodiments included herein refer to the use of electrodes to deliver therapy, other energy delivery members (e.g., ultrasound transducers or other ultrasound energy delivery members) or other therapeutic members or substances (e.g., fluid delivery devices or members to deliver chemicals, drugs, cryogenic fluid, hot fluid or steam, or other fluids) may be used or delivered in other embodiments.

FIG. 1 illustrates generally a schematic of an embodiment of a system 100 using wireless communication paths. The system 100 includes an example of an external source 102, such as a midfield transmitter source, sometimes referred to as a midfield coupler, located at or above an interface 105 between air 104 and a higher-index material 106, such as body tissue. The external source 102 can produce a source current (e.g., an in-plane source current). The source current (e.g., in-plane source current) can generate an electric field and a magnetic field. The magnetic field can include a non-negligible component that is parallel to the surface of the source 102 and/or to a surface of the higher-index material 106 (e.g., a surface of the higher-index material 106 that faces the external source 102). In accordance with several embodiments, the external source 102 may comprise structural features and functions described in connection with the midfield couplers and external sources included in WIPO Publication No. WO/2015/179225 published on Nov. 26, 2015 and titled "MIDFIELD COUPLER", which is incorporated herein by reference in its entirety.

The external source 102 can include at least a pair of outwardly facing electrodes 121 and 122. The electrodes 121 and 122 can be configured to contact a tissue surface, for example, at the interface 105. In one or more examples, the external source 102 is configured for use with a sleeve, pocket, or other garment or accessory that maintains the external source 102 adjacent to the higher-index material 106, and that optionally maintains the electrodes 121 and 122 in physical contact with a tissue surface. In one or more examples, the sleeve, pocket, or other garment or accessory can include or use a conductive fiber or fabric, and the electrodes 121 and 122 can be in physical contact with the tissue surface via the conductive fiber or fabric.

In one or more examples, more than two outwardly facing electrodes can be used and processor circuitry on-board or auxiliary to the source 102 can be configured to select an optimal pair or group of electrodes to use to sense farfield signal information (e.g., signal information corresponding to a delivered therapy signal or to a nearfield signal). In such embodiments, the electrodes can operate as antennas. In one or more examples, the source 102 includes three outwardly facing electrodes arranged as a triangle, or four outwardly facing electrodes arranged as a rectangle, and any two or more of the electrodes can be selected for sensing and/or can be electrically grouped or coupled together for sensing or diagnostics. In one or more examples, the processor circuitry can be configured to test multiple different electrode combination selections to identify an optimal configuration for sensing a farfield signal (an example of the processor circuitry is presented in FIG. 2A, among others).

FIG. 1 illustrates an embodiment of an implantable device 110, such as can include a multi-polar therapy delivery device configured to be implanted in the higher-index material 106 or in a blood vessel. In one or more examples, the implantable device 110 includes all or a portion of the circuitry 500 from FIG. 5, discussed in further detail below. In one or more examples, the implantable device 110 is implanted in tissue below the tissue-air interface 105. In FIG. 1, the implantable device 110 includes an elongate body and multiple electrodes E0, E1, E2, and E3 that are axially spaced apart along a portion of the elongate body. The implantable device 110 includes receiver and/or transmitter circuitry (not shown in FIG. 1, see e.g., FIGS. 2A, 2B, and 4, among others) that can enable communication between the implantable device 110 and the external source 102.

The various electrodes E0-E3 can be configured to deliver electrostimulation therapy to patient tissue, such as at or near a neural or muscle target. In one or more examples, at least one electrode can be selected for use as an anode and at least one other electrode can be selected for use as a cathode to define an electrostimulation vector. In one or more examples, electrode E1 is selected for use as an anode and electrode E2 is selected for use as a cathode. Together, the E1-E2 combination defines an electrostimulation vector V12. Various vectors can be configured independently to provide a neural electrostimulation therapy to the same or different tissue target, such as concurrently or at different times.

In one or more examples, the source 102 includes an antenna (see, e.g., FIG. 3) and the implantable device 110 includes an antenna 108 (e.g., and electric field-based or magnetic field-based antenna). The antennas can be configured (e.g., in length, width, shape, material, etc.) to transmit and receive signals at substantially the same frequency. The implantable device 110 can be configured to transmit power and/or data signals through the antenna 108 to the external source 102 and can receive power and/or data signals transmitted by the external source 102. The external source 102 and implantable device 110 can be used for transmission and/or reception of RF signals. A transmit/receive (T/R) switch can be used to switch each RF port of the external source 102 from a transmit (transmit data or power) mode to a receive (receive data) mode. A T/R switch can similarly be used to switch the implantable device 110 between transmit and receive modes. See FIG. 4, among others, for examples of T/R switches.

Figure 3:
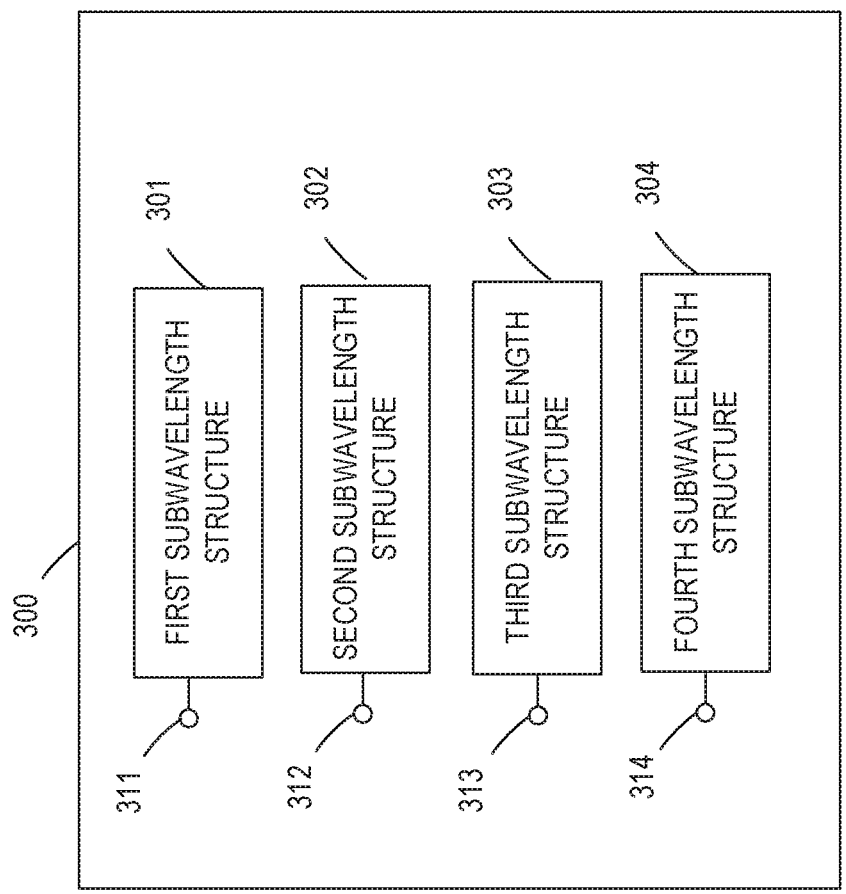
FIG. 3 illustrates generally a schematic view of an embodiment of a midfield antenna with multiple subwavelength structures.
Figure 4:
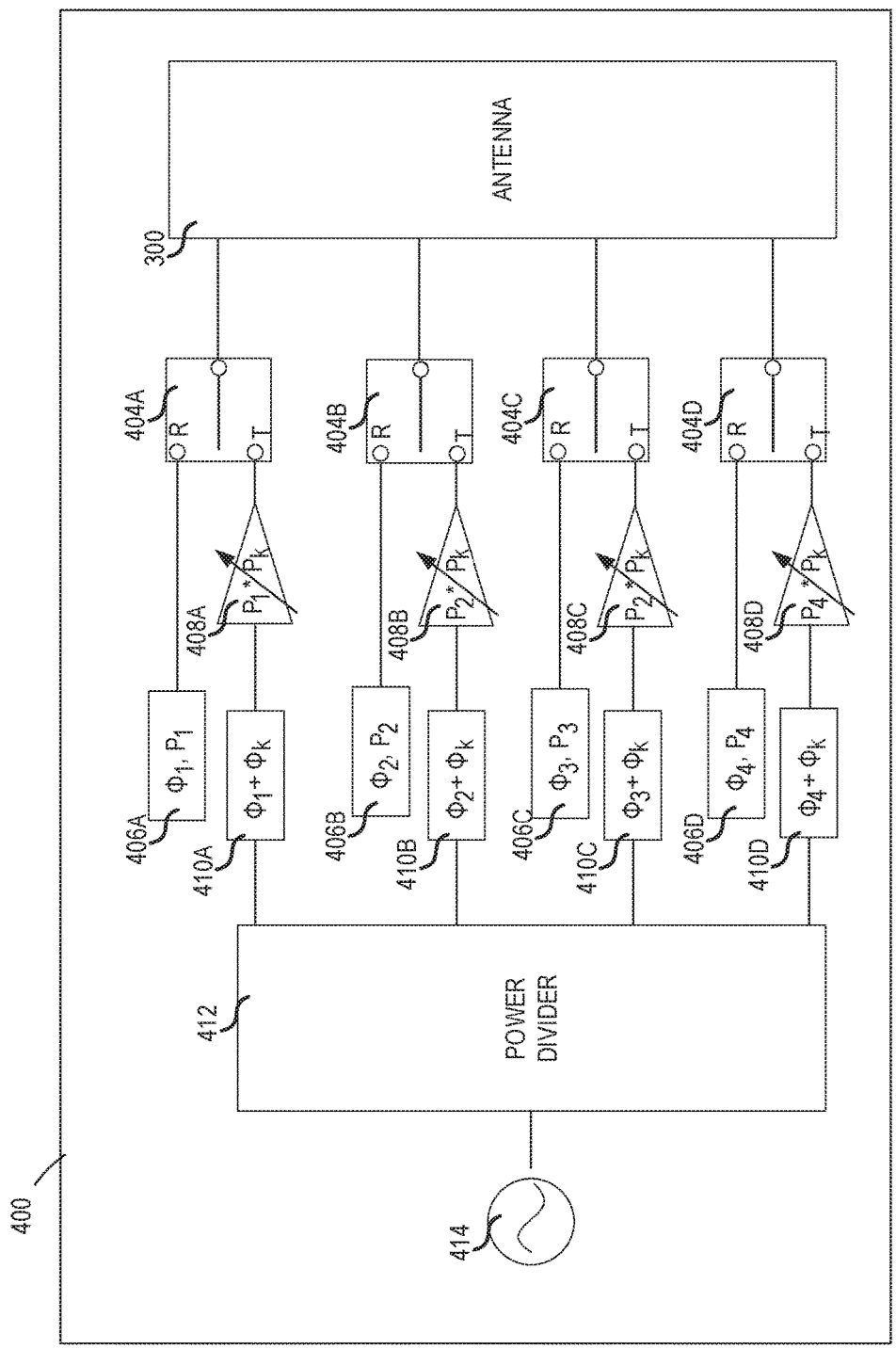
FIG. 4 illustrates generally a diagram of an embodiment of a phase-matching and/or amplitude-matching network for a midfield source device.

In one or more examples, a receive terminal on the external source 102 can be connected to one or more components that detect a phase and/or amplitude of a received signal from the implantable device 110. The phase and amplitude information can be used to program a phase of the transmit signal, such as to be substantially the same relative phase as a signal received from the implantable device 110. To help achieve this, the external source 102 can include or use a phase-matching and/or amplitude-matching network, such as shown in the embodiment of FIG. 4. The phase-matching and/or amplitude matching network can be configured for use with a midfield antenna that includes multiple ports, such as shown in the embodiment of FIG. 3.

Referring again to FIG. 1, in one or more examples, the implantable device 110 can be configured to receive a midfield signal 131 from the external source 102. The midfield signal 131 can include power and/or data signal components. In some embodiments, a power signal component can include one or more data components embedded therein. In one or more examples, the midfield signal 131 includes configuration data for use by the implantable device 110. The configuration data can define, among other things, therapy signal parameters, such as a therapy signal frequency, pulse width, amplitude, or other signal waveform parameters. In one or more examples, the implantable device 110 can be configured to deliver an electrostimulation therapy to a therapy target 190, such as can include a neural target (e.g., a nerve, or other tissue such as a vein, connective tissue, or other tissue that includes one or more neurons within or near the tissue), a muscle target, or other tissue target. An electrostimulation therapy delivered to the therapy target 190 can be provided using a portion of a power signal received from the external source 102. Examples of the therapy target 190 can include nerve tissue or neural targets, for example including nerve tissue or neural targets at or near cervical, thoracic, lumbar, or sacral regions of the spine, brain tissue, muscle tissue, abnormal tissue (e.g., tumor or cancerous tissue), targets corresponding to sympathetic or parasympathetic nerve systems, targets at or near peripheral nerve bundles or fibers, at or near other targets selected to treat incontinence, urinary urge, overactive bladder, fecal incontinence, constipation, pain, neuralgia, pelvic pain, movement disorders or other diseases or disorders, deep brain stimulation (DBS) therapy targets or any other condition, disease or disorder (such as those other conditions, diseases, or disorders identified herein).

Delivering the electrostimulation therapy can include using a portion of a power signal received via the midfield signal 131, and providing a current signal to an electrode or an electrode pair (e.g., two or more of E0-E3), coupled to the implantable device 110, to stimulate the therapy target 190. As a result of the current signal provided to the electrode(s), a nearfield signal 132 can be generated. An electric potential difference resulting from the nearfield signal 132 can be detected remotely from the therapy delivery location. Various factors can influence where and whether the potential difference can be detected, including, among other things, characteristics of the therapy signal, a type or arrangement of the therapy delivery electrodes, and characteristics of any surrounding biologic tissue. Such a remotely detected electric potential difference can be considered a farfield signal 133. The farfield signal 133 can represent an attenuated portion of the nearfield signal 132. That is, the nearfield signal 132 and the farfield signal 133 can originate from the same signal or field, such as with the nearfield signal 132 considered to be associated with a region at or near the implantable device 110 and the therapy target 190, and with the farfield signal 133 considered to be associated with other regions more distal from the implantable device 110 and the therapy target 190. In one or more examples, information about the implantable device 110, or about a previously-provided or future planned therapy provided by the implantable device 110, can be encoded in a therapy signal and detected and decoded by the external source 102 by way of the farfield signal 133.

In one or more examples, the device 110 can be configured to provide a series of electrostimulation pulses to a tissue target (e.g., neural target). For example, the device 110 can provide multiple electrostimulation pulses separated in time, such as using the same or different electrostimulation vectors, to provide a therapy. In one or more examples, a therapy comprising multiple signals can be provided to multiple different vectors in parallel, or can be provided in sequence such as to provide a series or sequence of electrostimulation pulses to the same neural target. Thus, even if one vector is more optimal than the others for eliciting a patient response, the therapy as a whole can be more effective than stimulating only the known-optimal vector because (1) the target may experience a rest period during periods of non-stimulation, and/or (2) stimulating the areas nearby and/or adjacent to the optimal target can elicit some patient benefit.

The system 100 can include a sensor 107 at or near the interface 105 between air 104 and the higher-index material 106. The sensor 107 can include, among other things, one or more electrodes, an optical sensor, an accelerometer, a temperature sensor, a force sensor, a pressure sensor, or a surface electromyography (EMG) device. The sensor 107 may comprise multiple sensors (e.g., two, three, four or more than four sensors). Depending on the type of sensor(s) used, the sensor 107 can be configured to monitor electrical, muscle, or other activity near the device 110 and/or near the source 102. For example, the sensor 107 can be configured to monitor muscle activity at a tissue surface. If muscle activity greater than a specified threshold activity level is detected, then a power level of the source 102 and/or of the device 110 can be adjusted. In one or more examples, the sensor 107 can be coupled to or integrated with the source 102, and in other examples, the sensor 107 can be separate from, and in data communication with (e.g., using a wired or wireless electrical coupling or connection), the source 102 and/or the device 110.

The system 100 can include a farfield sensor device 130 that can be separate from, or communicatively coupled with, one or more of the source 102 and the sensor 107. The farfield sensor device 130 can include two or more electrodes and can be configured to sense a farfield signal, such as the farfield signal 133 corresponding to a therapy delivered by the device 110. The farfield sensor device 130 can include at least one pair of outwardly facing electrodes 123 and 124 configured to contact a tissue surface, for example, at the interface 105. In one or more examples, three or more electrodes can be used, and processor circuitry on-board or auxiliary to the farfield sensor device 130 can select various combinations of two or more of the electrodes for use in sensing the farfield signal 133. In one or more examples, the farfield sensor device 130 can be configured for use with a sleeve, pocket, or other garment or accessory that maintains the farfield sensor device 130 adjacent to the higher-index material 106, and that optionally maintains the electrodes 123 and 124 in physical contact with a tissue surface. In one or more examples, the sleeve, pocket, or other garment or accessory can include or use a conductive fiber or fabric, and the electrodes 123 and 124 can be in physical contact with the tissue surface via the conductive fiber or fabric. An example of at least a portion of a farfield sensor device 130 is further described herein in connection with FIG. 2B.

In one or more examples, the external source 102 provides a midfield signal 131 including power and/or data signals to the implantable device 110. The midfield signal 131 includes a signal (e.g., an RF signal) having various or adjustable amplitude, frequency, phase, and/or other signal characteristics. The implantable device 110 can include an antenna, such as described below, that can receive the midfield signal 131 and, based on characteristics of receiver circuitry in the implantable device 110, can modulate the received signal at the antenna to thereby generate a backscatter signal. In one or more examples, the implantable device 110 can encode information in the backscatter signal 112, such as information about a characteristic of the implantable device 110 itself, about a received portion of the midfield signal 131, about a therapy provided by the implantable device 110, and/or other information. The backscatter signal 112 can be received by an antenna at the external source 102 and/or the farfield sensor device 130, or can be received by another device. In one or more examples, a biological signal can be sensed by a sensor of the implantable device 110, such as a glucose sensor, an electropotential (e.g., an electromyography sensor, electrocardiograph (ECG) sensor, resistance, or other electrical sensor), a light sensor, a temperature, a pressure sensor, an oxygen sensor, a motion sensor, or the like. A signal representative of the detected biological signal can be modulated onto the backscatter signal 112. Other sensors are discussed elsewhere herein, such as with regard to FIG. 81, among others. In such embodiments, the sensor 107 can include a corresponding monitor device, such as a glucose, temperature, ECG, EMG, oxygen, or other monitor, such as to receive, demodulate, interpret, and/or store data modulated onto the backscatter signal.

In one or more examples, the external source 102 and/or the implantable device 110 can include an optical transceiver configured to facilitate communication between the external source 102 and the implantable device 110. The external source 102 can include a light source, such as a photo laser diode or LED, or can include a photo detector, or can include both of a light source and a photo detector. The implantable device 110 can include a light source, such as a photo laser diode or LED, or can include a photo detector, or can include both of a light source and a photo detector. In an example, the external source 102 and/or implantable device 110 can include a window, such as made of quartz, glass, or other translucent material, adjacent to its light source or photo detector.

In an example, optical communications can be separate from or supplemental to an electromagnetic coupling between the external source 102 and the implantable device 110. Optical communication can be provided using light pulses modulated according to various protocols, such as using pulse position modulation (PPM). In an example, a light source and/or photo detector on-board the implantable device 110 can be powered by a power signal received at least in part via midfield coupling with the external source 102.

In an example, a light source at the external source 102 can send a communication signal through skin, into subcutaneous tissue, and through an optical window (e.g., quartz window) in the implantable device 110. The communication signal can be received at a photo detector on-board the implantable device 110. Various measurement information, therapy information, or other information from or about the implantable device can be encoded and transmitted from the implantable device 110 using a light source provided at the implantable device 110. The light signal emitted from the implantable device 110 can travel through the same optical window, subcutaneous tissue, and skin tissue, and can be received at photo detector on-board the external source 102. In an example, the light sources and/or photo detectors can be configured to emit and/or receive, respectively, electromagnetic waves in the visible or infrared ranges, such as in a range of about 670-910 nm wavelength (e.g., 670 nm-800 nm, 700 nm-760 nm, 670 nm-870 nm, 740 nm-850 nm, 800 nm-910 nm, overlapping ranges thereof, or any value within the recited ranges).

Figure 2A:
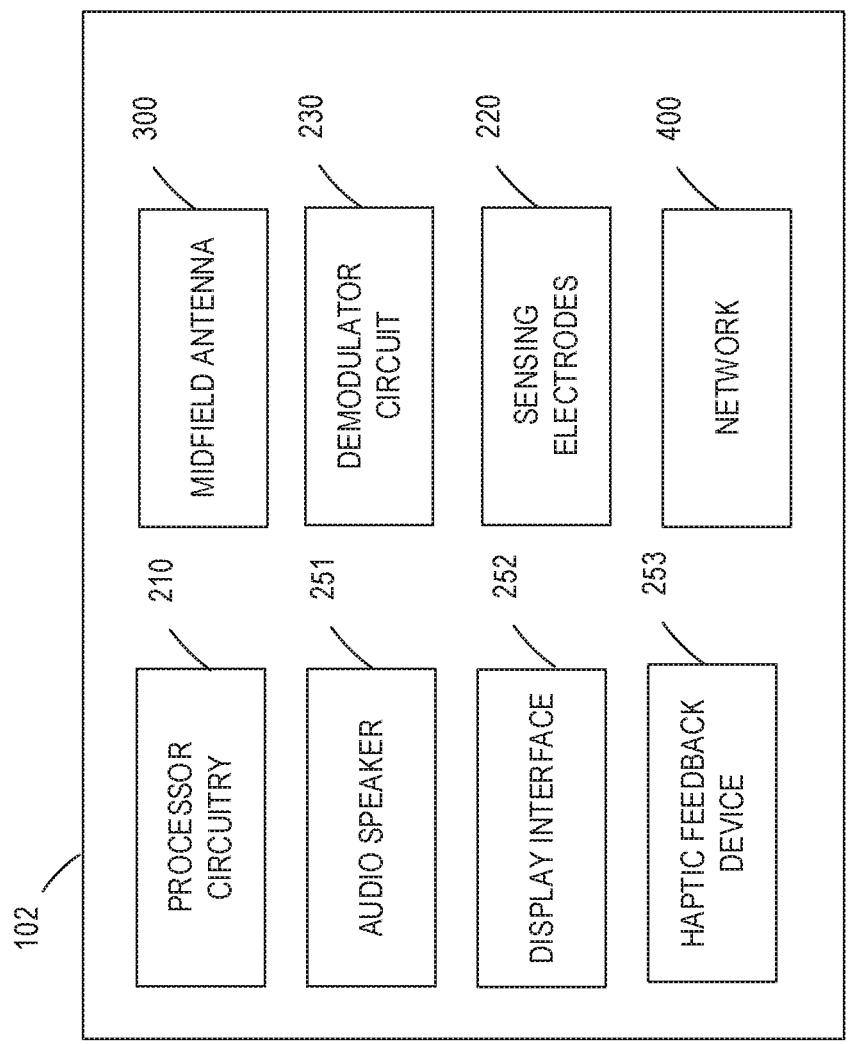
FIG. 2A illustrates generally a block diagram of an embodiment of a midfield source device.

FIG. 2A illustrates, by way of example, a block diagram of and embodiment of a midfield source device, such as the external source 102. The external source 102 can include various components, circuitry, or functional elements that are in data communication with one another. In the example of FIG. 2A, the external source 102 includes components, such as processor circuitry 210, one or more sensing electrodes 220 (e.g., including the electrodes 121 and 122), a demodulator circuitry 230, a phase-matching or amplitude-matching network 400, a midfield antenna 300, and/or one or more feedback devices, such as can include or use an audio speaker 251, a display interface 252, and/or a haptic feedback device 253. The midfield antenna 300 is further described below in the embodiment of FIG. 3, and the network 400 is further described below in the embodiment of FIG. 4. The processor circuitry 210 can be configured to coordinate the various functions and activities of the components, circuitry, and/or functional elements of the external source 102.

The midfield antenna 300 can be configured to provide a midfield excitation signal, such as can include RF signals having a non-negligible H-field component that is substantially parallel to an external tissue surface. In one or more examples, the RF signals can be adapted or selected to manipulate an evanescent field at or near a tissue surface, such as to transmit a power and/or data signal to respective different target devices (e.g., the implantable device 110, or any one or more other implantable devices discussed herein) implanted in tissue. The midfield antenna 300 can be further configured to receive backscatter or other wireless signal information that can be demodulated by the demodulator circuitry 230. The demodulated signals can be interpreted by the processor circuitry 210. The midfield antenna 300 can include a dipole antenna, a loop antenna, a coil antenna, a slot or strip antenna, or other antenna. The antenna 300 can be shaped and sized to receive signals in a range of between about 400 MHz and about 4 GHz (e.g., between 400 MHz and 1 GHz, between 400 MHz and 3 GHz, between 500 MHz and 2 GHz, between 1 GHz and 3 GHz, between 500 MHz and 1.5 GHz, between 1 GHz and 2 GHz, between 2 GHz and 3 GHz, overlapping ranges thereof, or any value within the recited ranges). For embodiments incorporating a dipole antenna, the midfield antenna 300 may comprise a straight dipole with two substantially straight conductors, a folded dipole, a short dipole, a cage dipole, a bow-tie dipole or batwing dipole.

The demodulator circuitry 230 can be coupled to the sensing electrodes 220. In one or more examples, the sensing electrodes 220 can be configured to receive the farfield signal 133, such as based on a therapy provided by the implantable device 110, such as can be delivered to the therapy target 190. The therapy can include an embedded or intermittent data signal component that can be extracted from the farfield signal 133 by the demodulator circuitry 230. For example, the data signal component can include an amplitude-modulated or phase-modulated signal component that can be discerned from background noise or other signals and processed by the demodulator circuitry 230 to yield an information signal that can be interpreted by the processor circuitry 210. Based on the content of the information signal, the processor circuitry 210 can instruct one of the feedback devices to alert a patient, caregiver, or other system or individual. For example, in response to the information signal indicating successful delivery of a specified therapy, the processor circuitry 210 can instruct the audio speaker 251 to provide audible feedback to a patient, can instruct the display interface 252 to provide visual or graphical information to a patient, and/or can instruct the haptic feedback device 253 to provide a haptic stimulus to a patient. In one or more examples, the haptic feedback device 253 includes a transducer configured to vibrate or to provide another mechanical signal.

Figure 2B:
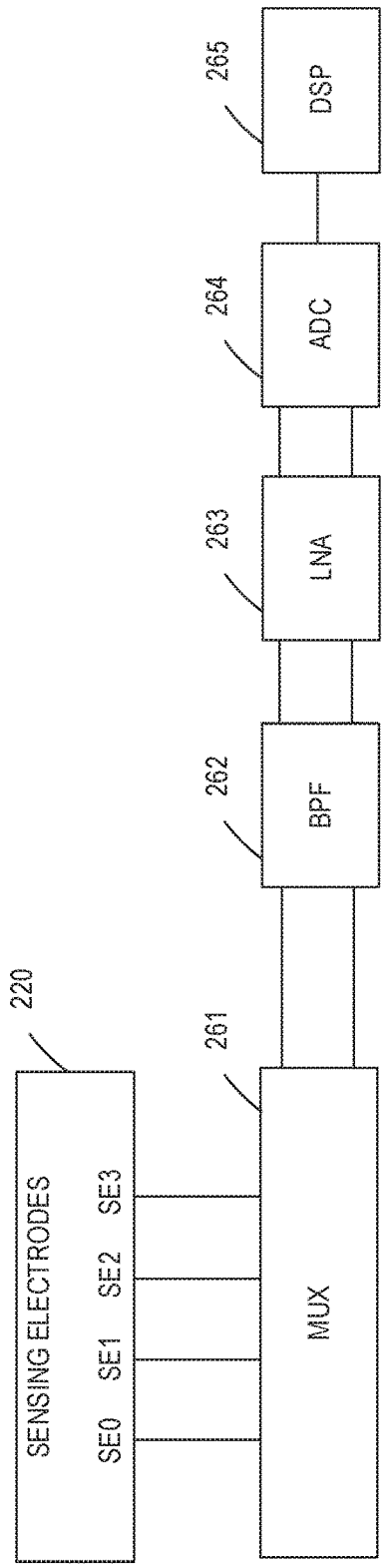
FIG. 2B illustrates generally a block diagram of an embodiment of a portion of a system configured to receive a signal.

FIG. 2B illustrates generally a block diagram of a portion of a system configured to receive a farfield signal. The system can include the sensing electrodes 220, such as can include the electrodes 121 and 122 of the source 102, or the electrodes 123 and 124 of the farfield sensor device 130. In the example of FIG. 2B, there are at least four sensing electrodes represented collectively as the sensing electrodes 220, and individually as SE0, SE1, SE2, and SE3, however, other numbers of sensing electrodes 220 may also be used. The sensing electrodes can be communicatively coupled to multiplexer circuitry 261. The multiplexer circuitry 261 can select pairs of the electrodes, or electrode groups, for use in sensing farfield signal information. In one or more examples, the multiplexer circuitry 261 selects an electrode pair or grouping based on a detected highest signal to noise ratio of a received signal, or based on another relative indicator of signal quality, such as amplitude, frequency content, and/or other signal characteristic.

Sensed electrical signals from the multiplexer circuitry 261 can undergo various processing to extract information from the signals. For example, analog signals from the multiplexer circuitry 261 can be filtered by a band pass filter 262. The band pass filter 262 can be centered on a known or expected modulation frequency of a sensed signal of interest. A band pass filtered signal can then be amplified by a low-noise amplifier 263. The amplified signal can be converted to a digital signal by an analog-to-digital converter circuitry (ADC) 264. The digital signal can be further processed by various digital signal processors 265, as further described herein, such as to retrieve or extract an information signal communicated by the implantable device 110.

FIG. 3 illustrates generally a schematic view of an embodiment of a midfield antenna 300 with multiple subwavelength structures 301, 302, 303, and 304. The midfield antenna 300 can include a midfield plate structure with a planar surface. The one or more subwavelength structures 301-304 can be formed in the plate structure. In the example of FIG. 3, the antenna 300 includes a first subwavelength structure 301, a second subwavelength structure 302, a third subwavelength structure 303, and a fourth subwavelength structure 304. Fewer or additional subwavelength structures can be used. The subwavelength structures can be excited individually or selectively by one or more RF ports (e.g., first through fourth RF ports 311, 312, 313, and 314) respectively coupled thereto. A "subwavelength structure" can include a hardware structure with dimensions defined relative to a wavelength of a field that is rendered and/or received by the external source 102. For example, for a given $\lambda_0$ corresponding to a signal wavelength in air, a source structure that includes one or more dimensions less than $\lambda_0$ can be considered to be a subwavelength structure. Various designs or configurations of subwavelength structures can be used. Some examples of a subwavelength structure can include a slot in a planar structure, or a strip or patch of a conductive sheet of substantially planar material.

FIG. 4 illustrates generally the phase-matching or amplitude-matching network 400. In an example, the network 400 can include the antenna 300, and the antenna 300 can be electrically coupled to a plurality of switches 404A, 404B, 404C, and 404D, for example, via the first through fourth RF ports 311, 312, 313, and 314 illustrated in FIG. 3. The switches 404A-D are each electrically coupled to a respective phase and/or amplitude detector 406A, 406B, 406C, and 406D, and a respective variable gain amplifier 408A, 408B, 408C, and 408D. Each amplifier 408A-D is electrically coupled to a respective phase shifter 410A, 410B, 410C, and 410D, and each phase shifter 410A-D is electrically coupled to a common power divider 412 that receives an RF input signal 414 to be transmitted using the external source 102.

In one or more examples, the switches 404A-D can be configured to select either a receive line ("R") or a transmit line ("T"). A number of switches 404A-D of the network 400 can be equal to a number of ports of the midfield source 402. In the example of the network 400, the midfield source 402 includes four ports (e.g., corresponding to the four subwavelength structures in the antenna 300 of the example of FIG. 3), however any number of ports (and switches), such as one, two, three, four, five, six, seven, eight or more, can be used.

The phase and/or amplitude detectors 406A-D are configured to detect a phase ($\Psi_1$, $\Psi_2$, $\Psi_3$, $\Psi_4$) and/or power (P1, P2, P3, P4) of a signal received at each respective port of the midfield source 402. In one or more examples, the phase and/or amplitude detectors 406A-D can be implemented in one or more modules (hardware modules that can include electric or electronic components arranged to perform an operation, such as determining a phase or amplitude of a signal), such as including a phase detector module and/or an amplitude detector module. The detectors 406A-D can include analog and/or digital components arranged to produce one or more signals representative of a phase and/or amplitude of a signal received at the external source 102.

The amplifiers 408A-D can receive respective inputs from the phase shifters 410A-D (e.g., Pk phase shifted by $\Psi_k$, $\Psi_1+\Psi_k$, $\Psi_2+\Psi_k$, $\Psi_3+\Psi_k$, or $\Psi_4+\Psi_k$). The output of the amplifier, O, is generally the output of the power divider, M when the RF signal 414 has an amplitude of 4*M (in the embodiment of FIG. 4), multiplied by the gain of the amplifier Pi*Pk. Pk can be set dynamically as the values for P1, P2, P3, and/or P4 change. $\Psi_k$ can be a constant. In one or more examples, the phase shifters 410A-D can dynamically or responsively configure the relative phases of the ports based on phase information received from the detectors 406A-D.

In one or more examples, a transmit power requirement from the midfield source 402 is Ptt. The RF signal provided to the power divider 412 has a power of 4*M. The output of the amplifier 408A is about M*P1*Pk. Thus, the power transmitted from the midfield coupler is M*(P1*Pk+P2*Pk+P3*Pk+P4*Pk)=Ptt. Solving for Pk yields Pk=Ptt/(M*(P1+P2+P3+P4)).

The amplitude of a signal at each RF port can be transmitted with the same relative (scaled) amplitude as the signal received at the respective port of the midfield coupler coupled thereto. The gain of the amplifiers 408A-D can be further refined to account for any losses between the transmission and reception of the signal from the midfield coupler. Consider a reception efficiency of η=Pir/Ptt, where Pir is the power received at the implanted receiver. An efficiency (e.g., a maximum efficiency), given a specified phase and amplitude tuning, can be estimated from an amplitude received at the external midfield source from the implantable source. This estimation can be given as η≈(P1+P2+P3+P4)/Pit, where Pit is an original power of a signal from the implanted source. Information about a magnitude of the power transmitted from the implantable device 110 can be communicated as a data signal to the external source 102. In one or more examples, an amplitude of a signal received at an amplifier 408A-D can be scaled according to the determined efficiency, such as to ensure that the implantable device receives power to perform one or more programmed operation(s). Given the estimated link efficiency, r, and an implant power (e.g., amplitude) requirement of Pir', Pk can be scaled as $Pk=Pir'/[\eta(P1+P2+P3+P4)]$, such as to help ensure that the implant receives adequate power to perform the programmed functions.

Control signals for the phase shifters 410A-D and the amplifiers 408A-D, such as the phase input and gain input, respectively, can be provided by processing circuitry that is not shown in FIG. 4. The circuitry is omitted to not overly complicate or obscure the view provided in FIG. 4. The same or different processing circuitry can be used to update a status of one or more of the switches 404A-D between receive and transmit configurations. See the processor circuitry 210 of FIG. 2A and its associated description for an example of processing circuitry.

Figure 5:
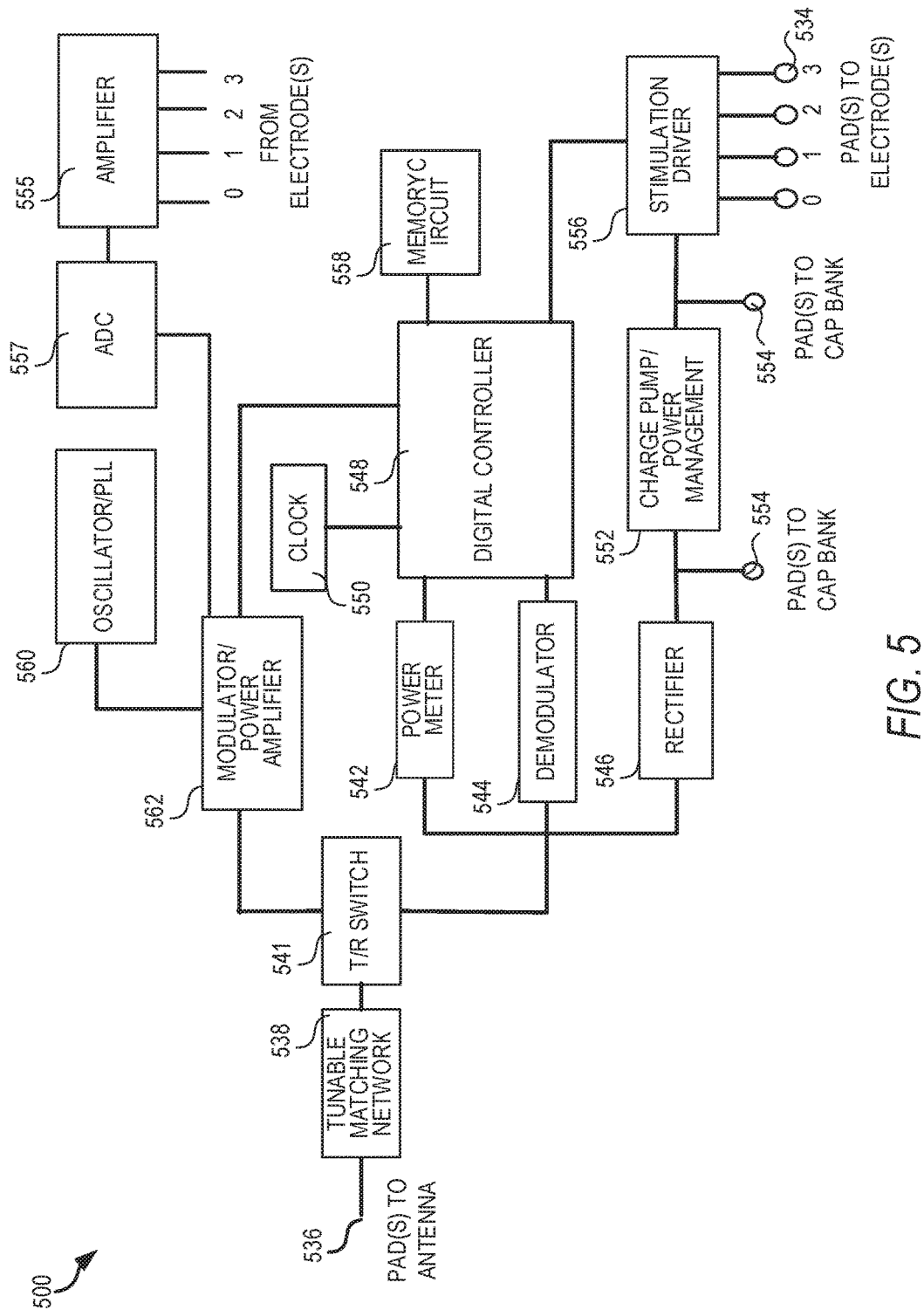
FIG. 5 illustrates generally a diagram of an embodiment of circuitry of an implantable device.

FIG. 5 illustrates generally a diagram of an embodiment of circuitry 500 of the implantable device 110, or target device, such as can include an elongate device and such as can optionally be deployed inside a blood vessel, according to one or more of the embodiments discussed herein. The circuitry 500 includes one or more pad(s) 536, such as can be electrically connected to the antenna 108. The circuitry 500 can include a tunable matching network 538 to set an impedance of the antenna 108 based on an input impedance of the circuitry 500. The impedance of the antenna 108 can change, for example, due to environmental changes. The tunable matching network 538 can adjust the input impedance of the circuitry 500 based on the varying impedance of the antenna 108. In one or more examples, the impedance of the tunable matching network 538 can be matched to the impedance of the antenna 108. In one or more examples, the impedance of the tunable matching network 538 can be set to cause a portion of a signal incident on the antenna 108 reflect back from the antenna 108, thus creating a backscatter signal.

A transmit-receive (T/R) switch 541 can be used to switch the circuitry 500 from a receive mode (e.g., in which power and/or data signals can be received) to a transmit mode (e.g., in which signals can be transmitted to another device, implanted or external). An active transmitter can operate at an Industrial, Scientific, and Medical (ISM) band of 2.45 GHZ or 915 MHz, or the 402 MHz Medical Implant Communication Service (MICS) band for transferring data from the implant. Alternatively, data can be transmitted using a Surface Acoustic Wave (SAW) device that backscatters incident radio frequency (RF) energy to the external device.

The circuitry 500 can include a power meter 542 for detecting an amount of received power at the implanted device. A signal that indicates power from the power meter 542 can be used by a digital controller 548 to determine whether received power is adequate (e.g., above a specified threshold) for the circuitry to perform some specified function. A relative value of a signal produced by the power meter 542 can be used to indicate to a user or machine whether an external device (e.g., the source 102) used to power the circuitry 500 is in a suitable location for transferring power and/or data to the target device.

In one or more examples, the circuitry 500 can include a demodulator 544 for demodulating received data signals. Demodulation can include extracting an original information-bearing signal from a modulated carrier signal. In one or more examples, the circuitry 500 can include a rectifier 546 for rectifying a received AC power signal.

Circuitry (e.g., state logic, Boolean logic, or the like) can be integrated into the digital controller 548. The digital controller 548 can be configured to control various functions of the receiver device, such as based on the input(s) from one or more of the power meter 542, demodulator 544, and/or the clock 550. In one or more examples, the digital controller 548 can control which electrode(s) (e.g., E0-E3) are configured as a current sink (anode) and which electrode(s) are configured as a current source (cathode). In one or more examples, the digital controller 548 can control a magnitude of a stimulation pulse produced through the electrode(s).

A charge pump 552 can be used to increase the rectified voltage to a higher voltage level, such as can be suitable for stimulation of the nervous system. The charge pump 552 can use one or more discrete components to store charge for increasing the rectified voltage. In one or more examples, the discrete components include one or more capacitors, such as can be coupled to pad(s) 554. In one or more examples, these capacitors can be used for charge balancing during stimulation, such as to help avoid tissue damage.

A stimulation driver circuitry 556 can provide programmable stimulation through various outputs 534, such as to an electrode array. The stimulation driver circuitry 556 can include an impedance measurement circuitry, such as can be used to test for correct positioning of the electrode(s) of the array. The stimulation driver circuitry 556 can be programmed by the digital controller to make an electrode a current source, a current sink, or a shorted signal path. The stimulation driver circuitry 556 can be a voltage or a current driver. The stimulation driver circuitry 556 can include or use a therapy delivery circuitry that is configured to provide electrostimulation signal pulses to one or more electrodes, such as using at least a portion of a received midfield power signal from the external source 102. In one or more examples, the stimulation driver circuitry 556 can provide pulses at frequencies up to about 100 kHz. Pulses at frequencies around 100 kHz can be useful for nerve blocking.

The circuitry 500 can further include a memory circuitry 558, such as can include a non-volatile memory circuitry. The memory circuitry 558 can include storage of a device identification, neural recordings, and/or programming parameters, among other implant related data.

The circuitry 500 can include an amplifier 555 and analog digital converter (ADC) 557 to receive signals from the electrode(s). The electrode(s) can sense electricity from nerve signals within the body. The nerve signals can be amplified by the amplifier 555. These amplified signals can be converted to digital signals by the ADC 557. These digital signals can be communicated to an external device. The amplifier 555, in one or more examples, can be a transimpedance amplifier.

The digital controller 548 can provide data to a modulator/power amplifier 562. The modulator/power amplifier 562 modulates the data onto a carrier wave. The power amplifier 562 increases the magnitude of the modulated waveform to be transmitted.

The modulator/power amplifier 562 can be driven by an oscillator/phase locked loop (PLL) 560. The PLL disciplines the oscillator so that it remains more precise. The oscillator can optionally use a different clock from the clock 550. The oscillator can be configured to generate an RF signal used to transmit data to an external device. A typical frequency range for the oscillator is about 10 kHz to about 2600 MHz (e.g., from 10 kHz to 1000 MHz, from 500 kHz to 1500 kHz, from 10 kHz to 100 kHz, from 50 kHz to 200 kHz, from 100 kHz to 500 kHz, from 100 kHz to 1000 kHz, from 500 kHz to 2 MHz, from 1 MHz to 2 MHz, from 1 MHz to 10 MHz, from 100 MHz to 1000 MHz, from 500 MHz to 2500 MHz, overlapping ranges thereof, or any value within the recited ranges). Other frequencies can be used, such as can be dependent on the application. The clock 550 is used for timing of the digital controller 548. A typical frequency of the clock 550 is between about one kilohertz and about one megahertz (e.g., between 1 kHz and 100 kHz, between 10 kHz and 150 kHz, between 100 kHz and 500 kHz, between 400 kHz and 800 kHz, between 500 kHz and 1 MHz, between 750 kHz and 1 MHz, overlapping ranges thereof, or any value within the recited ranges). Other frequencies can be used depending on the application. A faster clock generally uses more power than a slower clock.

A return path for a signal sensed from a nerve is optional. Such a path can include the amplifier 555, the ADC 557, the oscillator/PLL 560, and the modulator/power amplifier 562. Each of these items and connections thereto can optionally be removed.

In one or more examples, the digital controller 548, the amplifier 555, and/or the stimulation driver circuitry 556, among other components of the circuitry 500, can comprise portions of a state machine device. The state machine device can be configured to wirelessly receive power and data signals via the pad(s) 536 and, in response, release or provide an electrostimulation signal via one or more of the outputs 534. In one or more examples, such a state machine device needs not retain information about available electrostimulation settings or vectors, and instead the state machine device can carry out or provide electrostimulation events after, and/or in response to, receipt of instructions from the source 102.

For example, the state machine device can be configured to receive an instruction to deliver a neural electrostimulation therapy signal, such as at a specified time or having some specified signal characteristic (e.g., amplitude, duration, etc.), and the state machine device can respond by initiating or delivering the therapy signal at the specified time and/or with the specified signal characteristic(s). At a subsequent time, the device can receive a subsequent instruction to terminate the therapy, to change a signal characteristic, or to perform some other task. Thus, the device can optionally be configured to be substantially passive, or can be configured to be responsive to received instructions (e.g., contemporaneously received instructions).

A. Circuitry Housing Assemblies

This section describes embodiments and/or features of therapy devices, guiding mechanisms for situating an implantable device (e.g., the therapy device) within tissue, and/or affixing mechanisms for helping ensure the implantable device does not appreciably move when situated within the tissue. One or more examples regard therapy devices for treatment of incontinence (e.g., urinary incontinence, fecal incontinence), overactive bladder, pain or other conditions or symptoms, such as those described elsewhere herein.

An advantage of an implantable device discussed in this section (and others) can include one or more of: (i) a configurable implantable device that can be altered in shape and/or electrode configuration to help target a site for electrostimulation within a body; (ii) an implantable device that can be implanted and then affixed at a target location (such as an S3 foramen); (iii) an implantable device with improved signal reception efficiency (e.g., using (1) a dielectric material surrounding an antenna, the dielectric material including a dielectric constant that is between a dielectric constant of human tissue and that of air, or (2) multiple antennas in the implantable device, such as to include a primary antenna inductively coupled to a secondary antenna), (iv) a thin, discreet implantable device that can be implanted in narrow areas or thin tissue, such as between skin and bone; (v) an implantable device that can provide an electrostimulation pattern that an elongated tubular implantable device is not able to provide (e.g., due to the location of the electrodes and shape of the implantable device); and/or (vi) a network of implantable devices that can provide a local or wide area stimulation individually or in combination, among others.

In accordance with several embodiments, a system includes an implantable device comprising an elongated member having a distal portion and a proximal portion. The device includes a plurality of electrodes, a circuitry housing, circuitry within the circuitry housing adapted to provide electrical energy to the plurality of electrodes, an antenna housing, and an antenna (e.g., a helical antenna) in the antenna housing. The plurality of electrodes is situated or located along the distal portion of the elongated member. The circuitry housing is attached to the proximal portion of the elongated member. The circuitry is hermetically sealed or encased within the circuitry housing. The antenna housing is attached to the circuitry housing at a proximal end of the circuitry housing opposite to an end of the circuitry housing attached to the elongated member.

The system may optionally comprise an external midfield power source adapted to provide a power or electrical signal or energy to the implantable device. The implantable device may be adapted to communicate information (e.g., data signals) to an antenna of the external source via the antenna. One, more than one or all the electrodes may optionally be located at a proximal portion or central portion of the elongated member instead of the distal portion. The circuitry housing may optionally be attached to a distal portion or central portion of the elongated member. The antenna housing may not be attached to the circuitry housing or may not be attached to the proximal end of the circuitry housing. The antenna housing may optionally include a dielectric material with a dielectric constant between that of human tissue and air, such as a ceramic material. The ceramic material may optionally cover the antenna. The elongated member may optionally be flexible and/or cylindrical. The electrodes may optionally be cylindrically-shaped and positioned around a circumference of the elongated member.

The elongated member may optionally include a channel extending through the elongated member from a proximal end of the member to the distal portion of the elongated member and a memory metal wire situated in the channel, the memory metal wire pre-shaped in an orientation to provide curvature to the elongated member. The memory metal may optionally be shaped to conform to a shape of an S3 foramen and generally match a curve of a sacral nerve. The antenna may be a primary antenna and the device may further include a secondary antenna in a housing attached to the antenna housing, the secondary antenna shaped and positioned to provide a near field coupling with the primary antenna. The device may optionally include one or more sutures attached at one or more of: (1) a proximal portion of the antenna housing; (2) a proximal portion of the circuitry housing; and (3) an attachment structure attached to a proximal end of the antenna housing. The antenna may optionally be coupled to a conductive loop of the circuitry situated in a proximal portion of the circuitry housing. There may be a ceramic material between the antenna and the conductive loop.

There is an ongoing desire to reduce a displacement volume of implantable sensor and/or stimulator devices, such as including neurostimulation devices. Additional miniaturization can allow for an easier less invasive implant procedure, reduce a surface area of the implantable device which can in turn reduce a probability of post-implant infection, and provide patient comfort in a chronic ambulatory patient setting. In some examples, a miniaturized device can be injected using a catheter or cannula, further reducing invasiveness of an implant procedure.

In an example, a configuration of an implantable neurostimulation device is different from a conventional lead implanted with a pulse generator. The implantable stimulation device can include a lead-less design and can be powered from a remote source (e.g., a midfield source located distal to the implantable device).

In an example, a method of making an implantable stimulation device can include forming electrical connections at both ends of a circuitry housing, such as can be a hermetically sealed circuitry housing. The method can include forming electrical connections between a feedthrough assembly and pads of a circuit board. In an example, the feedthrough assembly includes a cap-like structure inside of which electrical and/or electronic components can be provided. A surface of the pads of the circuit board can be generally perpendicular to a surface of an end of feedthroughs of the feedthrough assembly.

The method can be useful in, for example, forming a hermetic circuitry housing, such as can be part of an implantable stimulation device or other device that can be exposed to liquid or other environmental elements that can adversely affect electrical and/or electronic components.

Various traditional assembly techniques can be difficult to apply to miniature devices such as implantable or injectable stimulator devices. For example, wirebonding can be difficult since connections to the substrate may be on a surface that is generally perpendicular to a feedthrough. In some examples, wirebonds can be compressed when the circuitry housing is sealed. Using thin wires that can be compressed to make connections between the substrate and the board, however, can increase parasitic capacitance and/or inductance of the RF feedthrough and may detune an RF receiving structure. Further, manufacturing yield may be limited through such compression and/or thin wires. The compression can break a bond between a wire and a pad or can break the wire itself. The thickness of the wire can affect how likely the wire is to break, for example because a thin wire can be more likely to break, when compressed, than a thicker wire.

Figure 6:
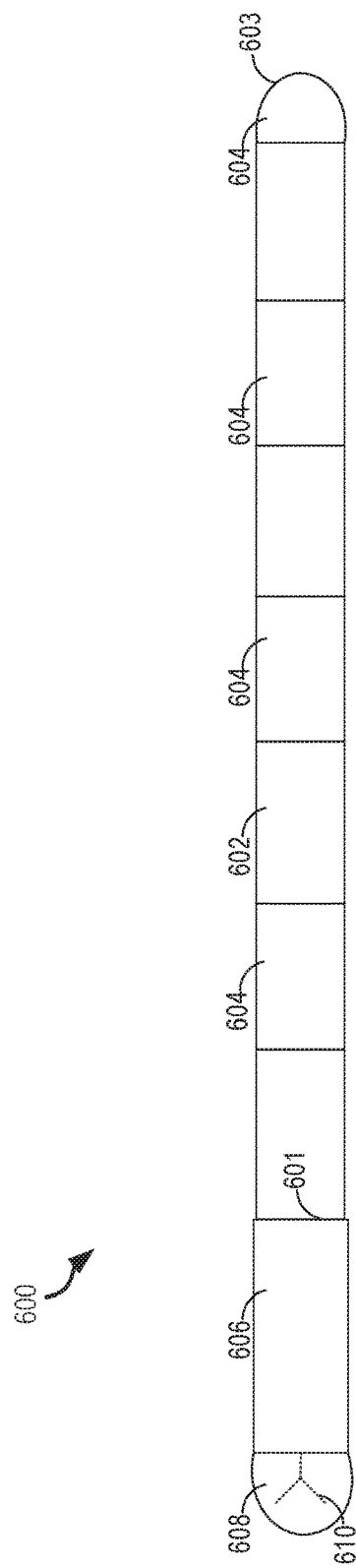
FIG. 6 illustrates generally a diagram of an embodiment of a first implantable device.

FIG. 6 illustrates generally a diagram of an embodiment of a first implantable device 600. The device 600 includes a body portion 602, multiple electrodes 604, a circuitry housing 606, and an antenna housing 608. The antenna housing 608 encapsulates an antenna 610. The implantable device 600 can be configured to sense electrical (or other) activity information from a patient, or to deliver an electrostimulation therapy to the patient such as using one or more of the electrodes 604.

The body portion 602 can be made of a flexible or rigid material. In one or more examples, the body portion 602 can include a bio-compatible material. The body portion 602 can include, among other materials, platinum, iridium, titanium, ceramic, zirconia, alumina, glass, polyurethane, silicone, epoxy, and/or a combination thereof.

The body portion 602 includes one or more electrodes 604 thereon or at least partially therein. The electrodes 604, as illustrated in the example of FIG. 6, are ring electrodes. In the example of FIG. 6, the electrodes 604 are substantially evenly distributed along the body portion, that is, a substantially equal space is provided between adjacent electrodes. Other electrode configurations can additionally or alternatively be used. Some examples of other electrode configurations are illustrated herein at, e.g., FIGS. 30A-40.

The body portion 602 can include, or can be coupled to, a circuitry housing 606. In an example, the circuitry housing 606 is coupled to the body portion 602 at a first end 601 of the body portion 602. In the example of FIG. 6, the first end 601 of the body portion 602 is opposite a second end 603 of the body portion 602.

The circuitry housing 606 can provide a hermetic seal for electric and/or electronic components 712 (see, e.g., FIG. 7) and/or interconnects housed therein. The electrodes 604 can be respectively electrically connected to circuitry in the circuitry housing 606 using one or more feedthroughs and one or more conductors, such as is illustrated and described herein. That is, the circuitry housing 606 can provide a hermetic enclosure for the electronic components 712 (e.g., electric and/or electronic components provided inside or encapsulated by the circuitry housing 606).

In an example, the antenna housing 608 is attached to the circuitry housing 606 at a first side end 711 (see, e.g., FIG. 7) of the circuitry housing 606. An antenna 610 can be provided inside the antenna housing 608. In an example, the antenna 610 is used for receiving at and/or transmitting from the device 1200 power and/or data signals. The first side end 711 is opposite a second side end 713 of the circuitry housing 606. In an example, the second side end 713 is an end to which an electrode assembly, such as including the electrodes 604, or other assembly, can be electrically connected.

The antenna housing 608 can be coupled to the circuitry housing 606 in various ways or using various connective means. For example, the antenna housing 608 can be brazed (e.g., using gold or other conductive or non-conductive material) to the circuitry housing 606. The antenna housing 608 can include an epoxy, tecothane, or other substantially radio frequency (RF) transparent (e.g., at a frequency used to communicate to/from the device 1200) and protective material.

In one or more examples, the antenna housing 608 can include a ceramic material such as zirconia or alumina. The dielectric constant of zirconia is similar to a dielectric constant of typical body muscle tissue. Using a material with a dielectric constant similar to that of muscle tissue can help stabilize the circuit impedance of the antenna 610 and can decrease a change in impedance when the antenna 610 is surrounded by different tissue types.

A power transfer efficiency such as from an external transmitter to the device 1200 can be influenced by the selection of antenna or housing materials. For example, a power transfer efficiency of the device 1200 can be increased when the antenna 610 is surrounded or encapsulated by a lower permittivity tissue, such as when the antenna housing 608 comprises a ceramic material. In an example, the antenna 610 can be composed as a single ceramic structure with the feedthrough.

Figure 7:
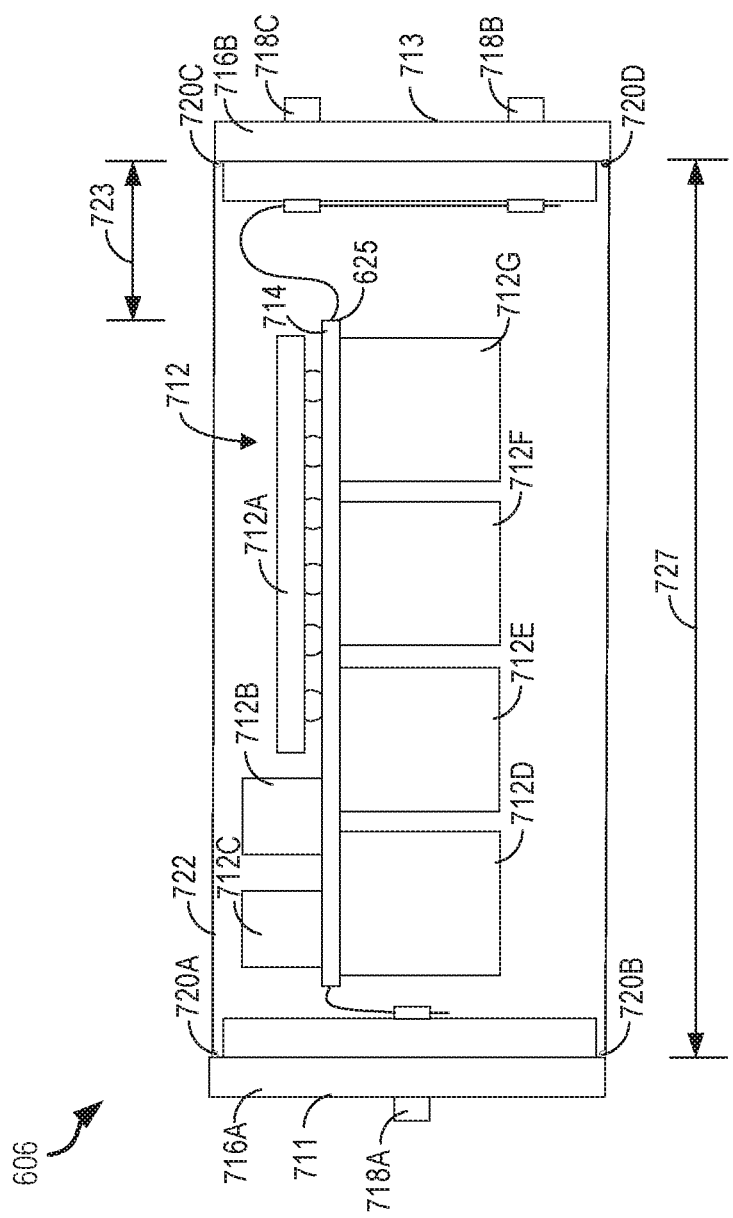
FIG. 7 illustrates generally a schematic view of an embodiment of a circuitry housing.

FIG. 7 illustrates generally a schematic view of an embodiment of the circuitry housing 606. The circuitry housing 606 as illustrated includes various electric and/or electronic components 712A, 712B, 712C, 712D, 712E, 712F, and 712G, such as can be electrically connected to a circuit board 714. The components 712A-G and the circuit board 714 are situated within an enclosure 722. In an example, the enclosure 722 comprises a portion of the circuitry housing 606.

One or more of the components 712A-G can include one or more transistors, resistors, capacitors, inductors, diodes, central processing units (CPUs), field programmable gate arrays (FPGAs), Boolean logic gates, multiplexers, switches, regulators, amplifiers, power sources, charge pumps, oscillators, phase locked loops (PLLs), modulators, demodulators, radios (receive and/or transmit radios), and/or antennas (e.g., a helical shaped antenna, a coil antenna, a loop antenna, or a patch antenna, among others), or the like. The components 712A-G in the circuitry housing 606 can be arranged or configured to form, among other things, stimulation therapy generation circuitry configured to provide stimulation therapy signals, such as can be delivered to a body using the electrodes 604, receiver circuitry configured to receive power and/or data from a remote device, transmitter circuitry configured to provide data to a remote device, and/or electrode selection circuitry such as configured to select which of the electrodes 604 is configured as one or more anodes or cathodes.

The enclosure 722 can include a platinum and iridium alloy (e.g., 90/10, 80/20, 95/15, or the like), pure platinum, titanium (e.g., commercially pure, 6Al/4V or another alloy), stainless steel, or a ceramic material (such as zirconia or alumina, for example), or other hermetic, biocompatible material. The circuitry housing 606 and/or the enclosure 722 can provide an airtight space for the circuitry therein. A thickness of a sidewall of the enclosure 722 can be about tens of micrometers, such as can be about ten, twenty, thirty, forty, fifty, sixty, seventy, eighty, ninety, one hundred, one hundred ten, etc. micrometers, or some thickness in between. An outer diameter of the enclosure 722 can be on the order of less than ten millimeters, such as can be about one, one and a half, two, two and a half, three, three and a half, etc. millimeters or some outer diameter in between. A length of the enclosure can be on the order of millimeters, such as can include two, three, four, five, six, seven, eight, nine, ten, eleven, twelve, thirteen, etc. millimeters, or some length in between. If a metallic material is used for the enclosure 722, the enclosure 722 can be used as part of the electrode array, effectively increasing the number of selectable electrodes 604 for stimulation.

Rather than being hermetic, the enclosure 722 can be backfilled to prevent ingress of moisture therein. The backfill material can include a non-conductive, waterproof material, such as epoxy, parylene, tecothane, or other material or combination of materials.

In the example of FIG. 7, the circuitry housing 606 can include a first end cap 716A and a second end cap 716B. In an example, the caps 716A and 716B are situated on or at least partially in the enclosure 722. The caps 716A and 716B can be provided to cover openings such as on substantially opposite sides of the enclosure 722. The cap 716A forms a portion of the first side end 711 of the circuitry housing 606 and the cap 716B forms a portion of the second side end 713 of the circuitry housing 606. Each of the caps 716A-B includes one or more conductive feedthroughs. In the example of FIG. 7, the first end cap 716A includes a first feedthrough 718A, and the second end cap 716B includes second and third feedthroughs 718B, and 718C. The conductive feedthroughs 718A-C provide an electrical path to a conductor connected thereto.

Figure 8:
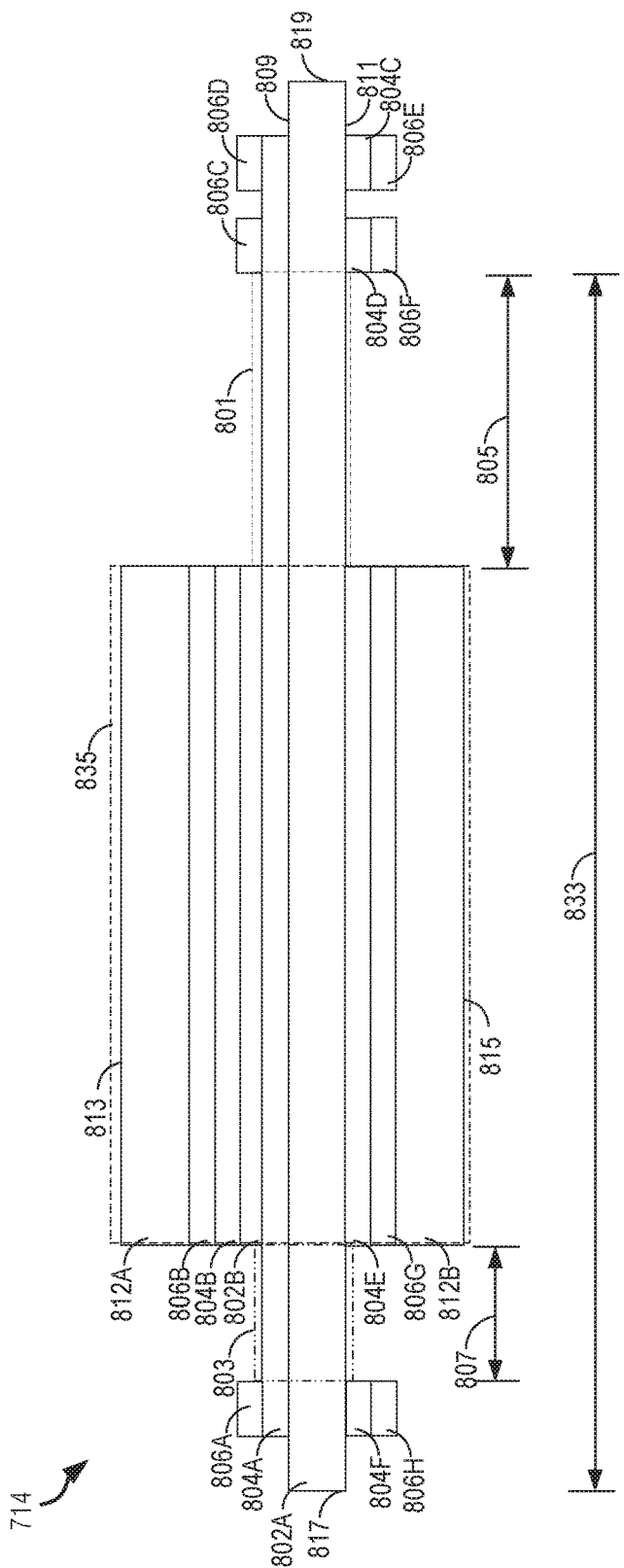
FIG. 8 illustrates generally a cross-section diagram of an embodiment of a circuit board.

FIG. 8 illustrates generally a cross-section diagram of an embodiment of the circuit board 714. FIGS. 9 and 10 illustrate generally top view diagrams of respective embodiments of the circuit board 714. The circuit board 714 as illustrated includes materials stacked to form a layered circuit board with one or more portions or materials that are flexible. Referring again to FIG. 8, the illustrated portions or structures of the circuit board 714 shown enclosed by dashed lines 801 and 803 can include a flexible material. Portions or structures illustrated outside of the dashed lines 801 and 803 can be flexible or rigid.

In the example of FIG. 8, the circuit board 714 includes dielectric material 802 and 812 (e.g., comprising one or more materials having the same or different dielectric or permittivity characteristics) provided in dielectric material regions 802A, 802B, 812A, and 812B, and conductive material 804 and 806 (e.g., comprising one or more materials having the same or different conductivity characteristics) provided in conductive material regions 804A-804F and 806A-806H. The dielectric regions can include the same or different dielectric materials, and the conductive material regions can include the same or different conductive materials.

In an example, the dielectric material regions 802A and 802B include polyimide, nylon, polyether ether ketone (PEEK), a combination thereof, or other flexible dielectric material. The dielectric material can include a solder mask and/or stiffener such as a polymer, epoxy, or other dielectric solder mask and/or stiffener material. In an example, the dielectric regions 812A and 812B include a stiffener material. In an example, a solder mask is used to enhance stiffness or rigidity for select portions of the circuit assembly.

In an example, the conductive material regions 804A, 804B, 804C, 804D, 804E, and 804F, comprise a first conductive material, and the conductive material regions 806A, 806B, 806C, 806D, 806E, 806F, 806G, and 806H, comprise a second conductive material. In one or more examples, the first conductive material can be rolled and/or annealed. The first conductive material can include copper, silver, nickel, gold, titanium, platinum, aluminum, steel, a combination thereof, or other conductive material. The second conductive material can include a solderable material (e.g., a material with an ability to form a bond with molten solder), such as can include one or more of the materials discussed with regard to the first conductive material. In an example, the second conductive material can include a plating that includes a material that has a relatively low rate of oxidation, such as can include silver, gold, nickel, and/or tin. In other examples, the conductive material regions 804A-804F and 806A-806H comprise the same type of material. The various conductive material regions can be used to provide portions of mating conductors such as can be used to connect the circuit board 714 to one or more other devices or components.

In an example, the first dielectric material 802A forms a base layer or bottom layer on which the remaining materials can be stacked or deposited to form the circuit board 714. Different materials can be stacked or deposited on different areas of the circuit board 714. For example, first materials can be stacked on a first surface 809 of the first dielectric material 802A and second materials can be stacked on an opposite second surface 811 of the first dielectric material 802A.

In an example, the first conductive material 804A is coupled with the first surface 809 of the first dielectric material 802A. The first conductive material 804A can be coupled with one or more of the first dielectric material at 802B and/or with the second conductive material at 806A, 806C, and/or 806D. The first conductive material 804A can be provided between the first dielectric material (e.g., at 802A and 802B) and the second conductive material (e.g., at 806A, 806C, and 806D). In an example, the first conductive material 802B extends into and through one or more flexible portions of the circuit board 714, such as at one or both of the areas inside of dashed lines 801 and 803.

In an example, a flexibility or rigidity of one or more portions of the circuit board 714 can be changed by selectively cutting or etching the circuit board 714. For example, the flexible portions shown enclosed by dashed lines 801 and 803 can be made more flexible by cutting various features into the board structures (e.g., into the first dielectric material 802A, the first conductive material 804A, etc). For example, laser cutting can be used to remove a partial layer of the materials or substrates forming the circuit board 714. In an example, cutting can include forming through-holes in the circuit board 714 to remove materials altogether. In an example, a laser cut feature includes one or more narrow openings or grooves that extend partially across the board, transversely to the length of the circuit board 714 (the length direction is indicated in FIG. 8 by 833). Such cut features can control rigidity characteristics and curvature of the circuit board 714.

Referring now to the examples of FIG. 8 and FIG. 9 together, the second conductive material at 806A, 806C, 806D, 806I, 806J, and 806K can be coupled with the first conductive material at 804A. The second conductive material at 806A, 806C, 806D, 806I, 806J, and 806K can be provided at or around respective openings or through-holes, such as illustrated at 920A, 920B, 920C, 920D, 920E, and 920F in FIG. 9. The openings 920A-F extend from a surface of the second conductive material 806A, 806C, 806D, 806I, 806J, and 806K to a respective opposite surface of the second conductive material 806H, 806F, and 8056E, respectively (some of which are obscured in the illustrated views). In an example, the openings 920A-F extend through the second conductive material 806A, 806C, 806D, 806I, 806J, and 806K, the first conductive material 804A, 804C, 804D, and 804F, and the first dielectric material 802A.

In an example, the first dielectric material 802B is coupled with the first conductive material 804A and the first conductive material 804B. The first dielectric material 802B can be provided on the first conductive material 804A. The first dielectric material 802B can be provided between the first conductive material at 804A and the first conductive material at 804B. The first dielectric material 802B can be provided between the second conductive material at 806A and the second conductive material at 806C, and with an unoccupied portion of the layer corresponding to the flexible portions of the circuit board 714 (e.g., corresponding to the areas in FIG. 8 enclosed by dashed lines 801 and 803).

The first conductive material 804B can be coupled with the first dielectric material 802B and the second conductive material 806B. The first conductive material 804B can be provided on the first dielectric material 802B. The first conductive material 804B can be provided between the first dielectric material 802B and the second conductive material 806B. The first conductive material 804B can be provided between the second conductive material 806A and the second conductive material 806C, such as with an open space corresponding to the flexible portions of the circuit board 714 (e.g., corresponding to the areas in FIG. 8 enclosed by dashed lines 801 and 803). Various couplings and/or interfaces between or among the dielectric material regions 802A, 802B, 812A, and 812B, and conductive material regions 804A-804F and 806A-806H can be provided as illustrated in FIG. 8 or otherwise.

The flexible portions of the circuit board 714 can have different dimensions. For example, a first flexible portion of the circuit board 714 indicated by the dashed line 801 can have a first length 805, and a second flexible portion of the circuit board 714 indicated by the dashed line 803 can have a different second length 807. In the example of FIG. 8, the second length 807 is less than the first length 805.

In an example, the second conductive material 806A, 806H, and 806K can be connected to the antenna 610. The length of the flexible portion near a first end 817 of the circuit board 714 affects a parasitic inductance and/or capacitance that affects the antenna 610. Thus, the second length 807 can be selected to reduce such parasitic capacitances and/or inductances. In an example, the first length 805 can be greater than a distance 723 (see FIG. 7). The distance 723 is illustrated as extending from an end 625 (see FIG. 7) of the dielectric material 802B to an end of the enclosure 722. The first length 805 can be selected such that the openings 920C-F (see FIG. 9) are outside the enclosure 722 when the openings 920A-B correspond to respective feedthroughs 718A (other feedthrough obscured in the view of FIG. 7) and the cap 716A is situated on, or at least partially in, the enclosure 722.

The circuit board 714 can have a board length that extends from its first end 817 to an opposite second end 819. In an example, a length (indicated by 833) of the circuit board 714 from its first end 817 to a distal end of the flexible portion indicated by the dashed lines 801 can be greater than a length of the enclosure 722 (e.g., indicated by 727 in FIG. 7). This length or distance relationship can allow the portion of the circuit board 714 on which the openings 920C-F (see FIG. 9) or pads 1102 (see FIG. 10) reside to turn or flex away from the central portion of the circuit board 714 such that the openings 920C-F or pads 1102 can be coupled to the cap 716A. A portion of the circuit board 714 between the first flexible portion and the second flexible portion, such as indicated by the dashed lines 835, can be flexible or rigid. As explained herein, rigidity characteristics of one or more portions of the circuit board 714 can be provided by solder, solder mask, electric and/or electronic components, one or more of the conductive materials 804 and 806 and/or one or more of the dielectric materials 802A, 802B and 812A, 812B, among other materials or techniques.

In an example, an embodiment of circuit board can have two rigid portions coupled by a flexible portion. For example, an elongated circuit board assembly can include, in order along its lengthwise direction, a proximal portion (e.g., corresponding to one or more of 802A, 804A, 804F, 806A, and/or 806H, near the proximal first end 817 of the board in the example of FIG. 8), a flexible portion (e.g., corresponding to one of the regions 801 and 803 in the example of FIG. 8), and a distal portion (e.g., corresponding to one or more of 804C, 804D, 806C, 806C, 806E, and/or 806F, near the distal second end 819 of the board in the example of FIG. 8). A hermetic enclosure can be configured to enclose the elongated circuit board assembly. In an example, the proximal and distal portions can be asymmetrical and can have different length characteristics.

FIGS. 9 and 10 illustrate respective embodiments of circuit boards 714A and 714B, such as can be embodiments of the circuit board 714. The circuit board 714A is similar to the circuit board 714B, however the circuit board 714B includes pads 1102, such as can optionally include solder bumps, instead of vias or throughholes, such as can be formed using e.g., the second conductive material 806A-K and the openings 920A-F. In an example, the circuit board 714A can be coupled or soldered to pins of the feedthroughs 718A-C.

Figure 18:
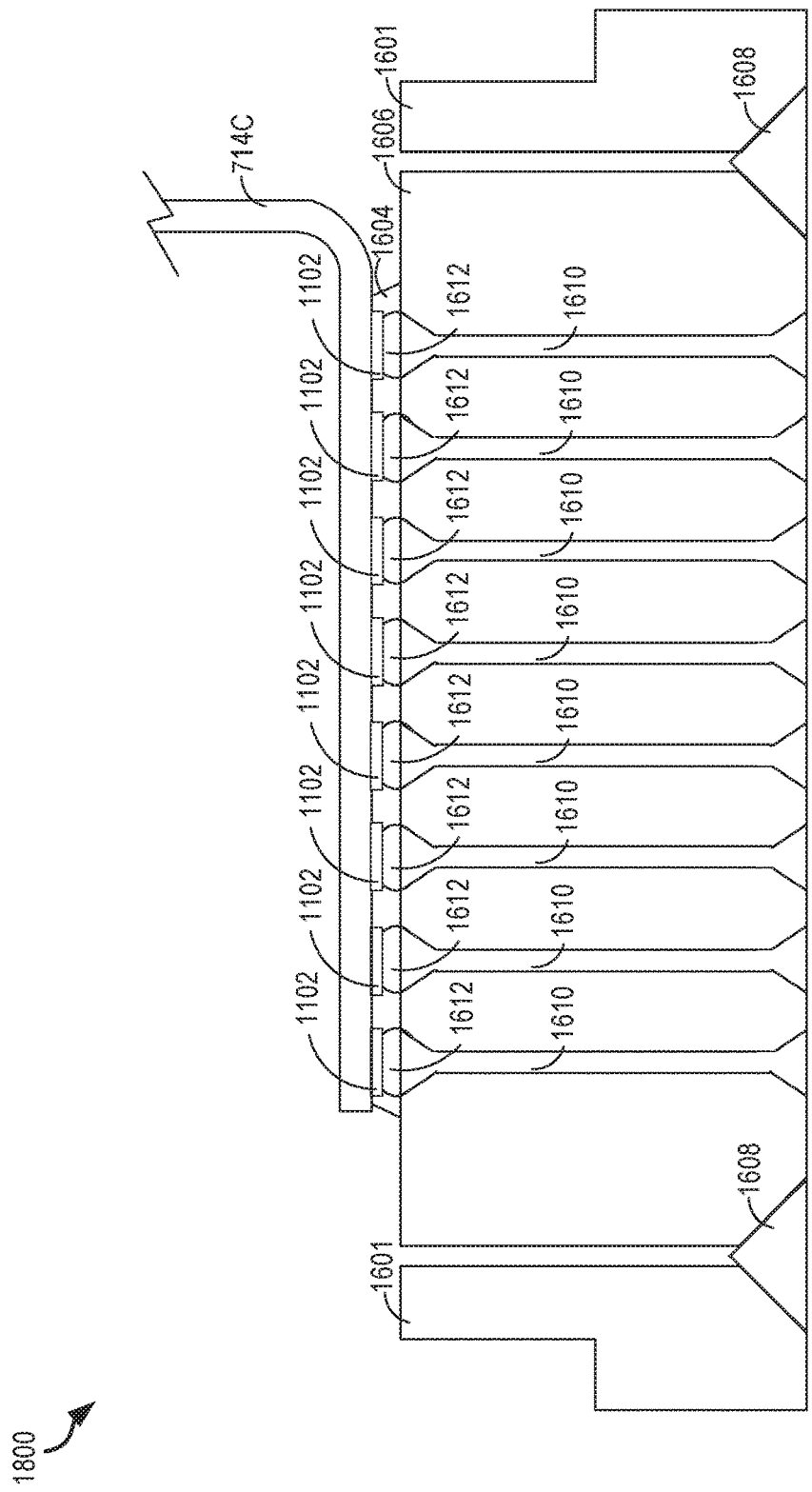
FIG. 18 illustrates generally an example of a cross-section view of an assembly that includes the end cap from FIG. 16 and a circuit board.

In an example, the circuit board 714B can be coupled to other components using a solder reflow technique, for example to couple the circuit board 714B to one or more pins (see, e.g., pins 1110 in the examples of FIGS. 16-18). While the example of the circuit board 714A includes vias and no pads, and the example of the circuit board 714B includes pads and no vias, other examples can include a combination of pads and/or vias and the caps 716A-B can be configured to accommodate such pads and/or vias. For example, the first end cap 716A can include one or more feedthroughs 718A while the second end cap 716B can include pads, or one cap can include feedthroughs 718A and pads 1102.

FIGS. 11-15 and 7 illustrate operations of an embodiment of a method that includes electrically connecting and enclosing the circuit board 714 in the circuitry housing 606. FIG. 11 illustrates an embodiment of a device 1100 that includes the electrical and/or electronic components 712A-G coupled to the circuit board 714. The circuit board 714 and components 712A-G are discussed generally above.

FIG. 12 illustrates an embodiment of a device 1200 that includes the device 1100 and the first end cap 716A. In an example, the device 1200 includes the second conductive material 806A, 806K, and/or 806H electrically connected to respective feedthroughs of the first end cap 716A, such as can include the feedthrough 718A.

FIG. 13 illustrates an embodiment of a device 1300 that includes the device 1200 and the enclosure 722. In the example of FIG. 13, the circuit board 714 and its components are provided inside of the enclosure 722. The first end cap 716A can be aligned with a first opening in the enclosure 722, and the cap can include one or more portions that extend at least partially inside of the enclosure 722. In the example of FIG. 13, a flexible distal portion of the circuit board 714 extends beyond an end 1331 of the enclosure 722, the end 1331 being opposite to the first opening in the enclosure 722. Electrical couplings provided on the extension portion of the circuit board 714, such as including the flexible distal portion, can be used to electrically couple the circuit board 714 (or one or more components thereon) with the second end cap 716B. That is, having the extension portion of the circuit board 714 can help facilitate making electrical connections because the connection task can be performed at least partially outside of the housing or enclosure 722.

FIG. 14 illustrates an embodiment of a device 1400 that includes the device 1300 and the second end cap 716B. In the example of FIG. 14, the circuit board 714, or one or more of the components coupled to the circuit 714, is electrically coupled to one or more of the feedthroughs 718B and 718C, and the feedthroughs 718B and 718C are coupled to the second end cap 716B. In an example, the second conductive material at 806C-D and/or 806I-J can be soldered or otherwise electrically coupled to respective locations on the feedthroughs 718B and 718C.

Figure 15:
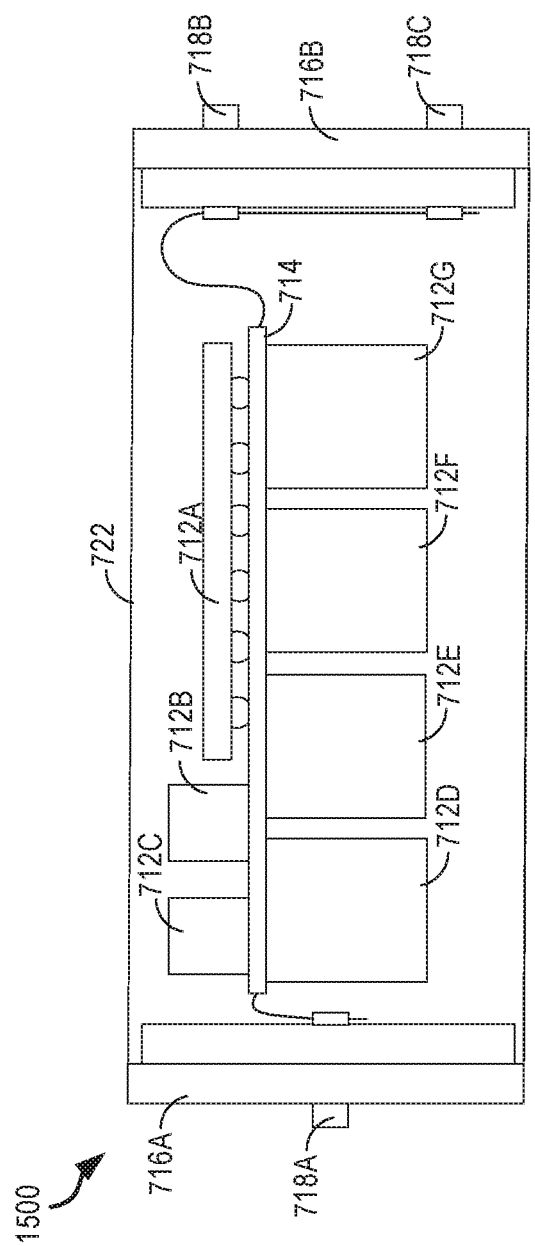
FIG. 15 illustrates generally an embodiment of a device that includes a circuit board coupled to first and second end caps and sealed inside an enclosure.

FIG. 15 illustrates an embodiment of a device 1500 that includes the device 1400 and the second end cap 716B installed is situated on the end 1331 of the enclosure 722. The first and second end caps 716A and 716B are provided or installed on opposite ends of the enclosure 722. The second end cap 716B can include one or more portions that extend at least partially inside of the enclosure 722.

Referring again to FIG. 7, the device 1500 is illustrated with the first and second end caps 716A and 716B coupled to the enclosure 722. The caps can be coupled to the enclosure 722 using various attachment processes, such as including brazing, welding, or other process. The example of FIG. 7 illustrates weld/braze marks 720A-720D that indicate that the first and second end caps 716A and 716B are affixed to the enclosure 722. Variations on the example method illustrated in FIGS. 7 and 11-15 can similarly be performed. For example, the first end cap 716A can be welded, brazed, bonded, or otherwise attached to the enclosure 722 before the circuit board 714 is coupled to the second end cap 716B.

FIG. 16 illustrates generally an example of a top view of an end cap 1600. In an example, the end cap 1600 corresponds to embodiments of the first and/or second end cap 716A and 716B. The example end cap 1600 includes a first dielectric material 1606, a connective material 1608, a flange material 1601, and a plurality of pins 1110. The dielectric material 1606 can include alumina, zirconia, sapphire, ruby, a combination thereof, or the like. The dielectric material 1606 can be substantive non-electrically conductive and securable to the flange material 1601. The flange material 1601 can include a metallic material, such as can include a platinum iridium alloy (e.g., 90/10, 95/15, 80/20, or the like), pure platinum, 6AL/4V titanium, 3Al/2.5V titanium, pure titanium, niobium, a combination thereof, or the like. In an example, the flange material 1601 can surround the dielectric material 1606. In the example of FIG. 16 that includes a circular profile, the dielectric material 1606 is concentric with the flange material 1601. In an example, the pins 1610 are hollow and conductive, and can comprise the same or similar materials as discussed above for the first and second conductive materials, such as at 804A-F and/or 806A-K.

The top view of FIG. 16 shows a first surface 1103 of the dielectric material 1606. The pins 1610 can extend from the first surface 1603 to an opposite second surface 1605 of the dielectric material 1606. In an example, each of the pins 1610 can be brazed welded, or otherwise hermetically sealed within the dielectric material 1606.

FIG. 17 illustrates generally an example of a cross-section view of the end cap 1600. The cross-section view shows the first and opposite second surfaces 1603 and 1605 of the end cap 1600. The cross-section view also shows the multiple pins 1610 that extend from the first surface 1603 to the second surface 1605, such as through the dielectric material 1606. In the example of FIG. 17, end portions of each of the pins 1610 includes a conductive adhesive 1612 provided at the second surface 1605. The conductive adhesive 1112 can include a solder, conductive paste, or other conductive material that can be used to electrically couple the pins 1610 of the end cap 1600 to another component. In an example, the conductive adhesive 1612 comprises solder bumps.

Referring now to FIGS. 6 and 17, the body portion 602 can be coupled to the circuitry housing 606 using the end cap 1600. In an example, the coupling can use conductive material coupled to the pins 1610 and can additionally or alternatively include welding or brazing the body portion 602 to the end cap 1600. In an example, the pins 1610 comprise hollow portions or receptacles that are configured to receive conductive members from the body portion 602.

FIG. 18 illustrates generally an example of a cross-section view of an assembly 1800 that includes the end cap 1600 and a circuit board 714C. The circuit board 714C can have the same or similar construction to one of the circuit boards 714, 174A, and/or 714B discussed herein. In an example, the circuit board 714C is similar to the circuit board 714B shown in FIG. 10, however with the circuit board 714C including additional pads 1102 than are illustrated in the example of the circuit board 714B. In the example of FIG. 18, the assembly 1800 includes the end cap 1600 electrically coupled to the circuit board 714C. For example, the conductive adhesive 1612 can be reflowed to adhere to the pads 1102.

In an example, an epoxy or other underfill material 1604 can be provided between the dielectric material 1606 and the circuit board 714C, such as to provide additional mechanical support and connectivity between the circuit board 714C and the dielectric material 1106, such as additional to any such connectivity provided by the electrical connections formed between the pads 1102 and the conductive adhesive 1612, and/or as insulation from shorts between the electrical connections.

A circuitry housing for an implantable device, such as the circuitry housing 606 as previously discussed, can include electric or electronic components for providing stimulation to a patient in which the implantable device is implanted. Also, as previously discussed, the circuitry housing can include one or more plates and/or feedthroughs (e.g., comprising a portion of one or more end caps), such as to seal the circuitry housing and/or provide electrical signals from within the circuitry housing to outside of the circuitry housing. The plates and/or feedthroughs can be made small, such as to help reduce or minimize a volume of the implantable device assembly. The present inventors have recognized, among other things, that a problem to be solved includes miniaturizing the plates and/or feedthroughs. The present inventors have recognized that a problem includes forming a feedthrough or plate that is less than about 3 millimeters in diameter. A solution to the problem can include selecting appropriate materials and assembly processes, as described herein.

By reducing a diameter of the end caps of the circuitry housing, the implantable device can require a smaller opening in the patient than is required for larger, previous implantable devices. A sheath (a lumen through which the implantable device is inserted into a patient) can be made with a smaller diameter as well. The implantable device may be sufficiently small to allow an implant procedure that does not use a sheath. In one or more examples, a body portion of an implantable device that includes electrodes (e.g., ring electrodes) situated thereon can be replaced or augmented with one or more electrodes on the cap. Such a configuration can further reduce an overall length of the implantable device, reduce a displacement volume of the implantable device, reduce a risk of infection, and/or reduce costs associated with making and/or installing the implantable device.

FIG. 19 illustrates generally an example of a top view of a dual-port cap 1900. FIG. 20 illustrates generally a cross-section view of the dual-port cap 1900. The dual-port cap 1900 is similar to the end cap 1600, with the cap 1900 including feedthroughs 718D and 718E instead of pins 1610. The cap 1900 is considered a "dual-port" cap because it includes a pair of feedthroughs or electrical ports. The feedthroughs 718D and 718E can extend or protrude away from the opposite side surfaces of the dual-port cap 1900, such as illustrated in FIG. 20. That is, portions of the feedthroughs 718D and 718E can include extension portions that extend way from the first and/or opposite second sides 1903 and 1905 of the cap.

In the example, the dual-port cap 1900 includes the flange material 1601, the dielectric material 1606, welded or brazed connective material 1608, and another connective material 1906 such as can be welded or brazed material around the feedthroughs 718D and 718E. The connective material 1906 can include gold, ruthenium, platinum, rhodium, palladium, silver, osmium, iridium, platinum, a combination thereof, or other noble material, or like material. The connective material 1906 can form a bond and/or seal a gap between the feedthroughs 718D and 718E and the dielectric material 1606. The feedthroughs 718D and 718E can include a conductive material, such as discussed previously regarding the feedthroughs 718A-C, and/or can include platinum, iridium, or a combination thereof, such as can include about eighty to a about one hundred percent platinum and the remainder being iridium. The dielectric material 1606, as previously discussed, can include a ceramic, such as can include alumina and/or zirconia. The flange material 1601, in one or more examples, can include a same or similar material as that of the feedthroughs 718D and 718E.

A diameter 1902 of the feedthroughs 718D and 718E can be less than one millimeter to e.g., several millimeters, such as can include about tenths of a millimeter, half a millimeter, one millimeter, one and a half millimeters, two millimeters, etc. or some diameter in between. A diameter 1904 of the dual-port cap 1900 can be between about 5 and about 9 French (e.g., about 1.67 millimeter and about 3 millimeters), such as can be about 7 French or less than about 3 millimeters and greater than about 1.5 millimeters.

FIG. 20 illustrates generally an example that includes a cross-section view of the dual-port cap 1900. In the example, the flange material 1601 can extend or protrude past a second surface 1605 of the dielectric material 1606. The flange material 1601 can be generally flush with the dielectric material 1606 at a first surface 1603. The feedthroughs 718D and 718E extend or protrude past the second surface 1605 and the first surface 1603. Welded or brazed connective materials 1608 and 1906 can be used to mechanically connect the flange material 1601 to the dielectric material 1606, and to mechanically connect the feedthroughs 718D and 718E to the dielectric material 1606, respectively. In an example, the welded or brazed materials discussed herein, such as the welded or brazed materials connective 1608 or 1906, can provide a hermetic seal, such that substantially no foreign matter can travel through the cap 1900 and into the enclosure 722. The feedthroughs 718D and 718E can be electrically connected to an antenna at or near one end thereof and to the circuit board 714 at or near the other, opposite end.

Figure 21:
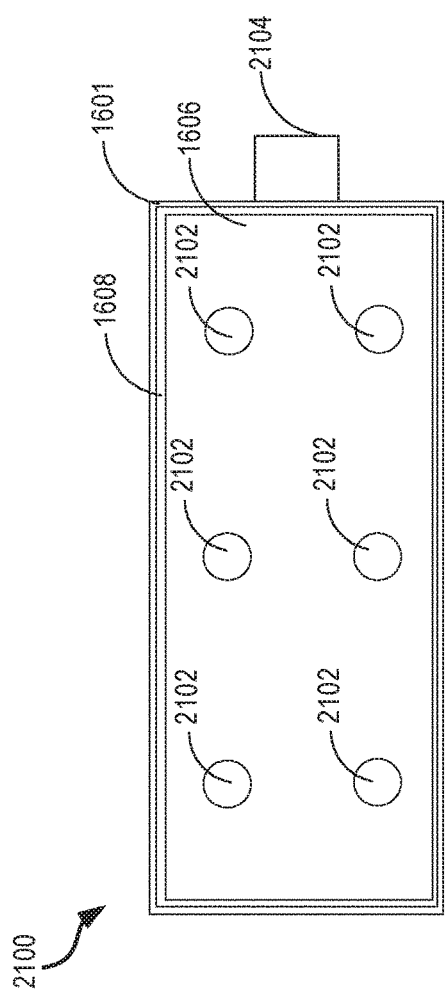
FIG. 21 illustrates generally an example of a top view of a multiple-port cap.

FIG. 21 illustrates generally an example of a top view of a multiple-port cap 2100. The cap 2100 can be used in place of one or more of the other caps discussed herein. In the example of FIG. 21, the multiple-port cap 2100 has a rectangular profile. The cap 2100 includes components similar to other caps discussed herein, with the shapes of some of the components being different than those previously illustrated or discussed herein. In an example, the cap 2100 includes electrode caps 2102 and a push rod assembly 2104.

The electrode caps 2102 can include one or more conductive materials, such as can be similarly used in the feedthroughs 718A-G, the connective material 1608 and/or 1906, the pins 1610, or other conductive material. The push rod assembly 2104 can provide a location at which to attach a push rod that can be used to situate the cap 2100 (and the circuitry attached thereto, see FIG. 23) within a patient, such as during an implant procedure. The push rod assembly 2104 can include an attachment mechanism (not shown), such as a threaded hole, a detent, or the like, to which the push rod can be attached.

Figure 22:
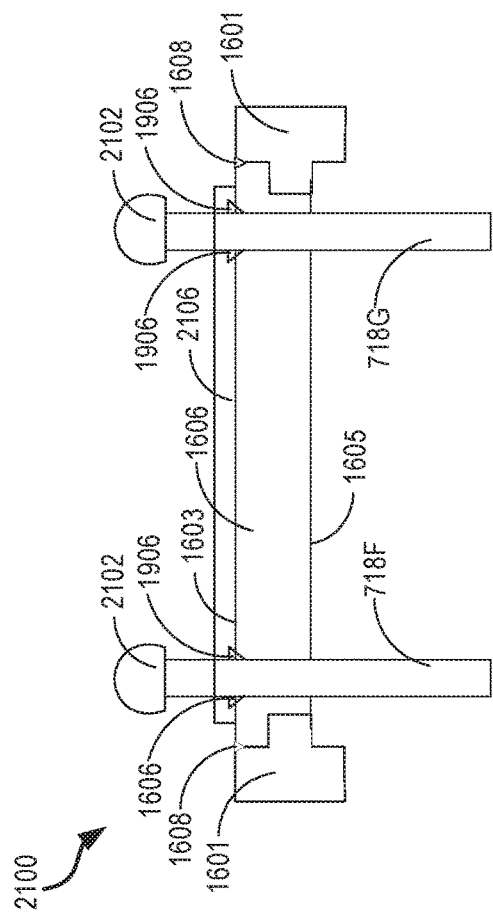
FIG. 22 illustrates generally an example that includes a cross-section view of the multiple-port cap from FIG. 21.

FIG. 22 illustrates generally an example that includes a cross-section view of the multiple-port cap 2100. The flange material 1601 of the cap 2100 is illustrated as including a stepped profile. The dielectric material 1606 can include a matching (e.g., mirroring) stepped profile, such that a step of the dielectric material 1606 mates with a step of the flange material 1601. Similarly to the other embodiments illustrated, the connective material 1608 and 1906 can mechanically connect the flange material 1601 to the dielectric material 1606, and can mechanically connect the feedthroughs to the dielectric material 1606, respectively.

In an example, the electrode caps 2102 can be pressed on or cast as part of the feedthroughs 718F and/or 718G. A distance from a tip of each of the electrode caps 2102 to the first surface 1603 can be different or the same for different feedthroughs. The cap 2100 as illustrated includes six feedthroughs and corresponding electrode caps 2102. The cap 2100 can include fewer or more feedthroughs and electrode caps, such as can include one, two, three, four, five, or more electrode caps and corresponding feedthroughs.

In an example, the cap 2100 can include an optional dielectric coating 2106, such as illustrated in FIG. 22. The dielectric coating 2106 can help prevent shunting of magnetic and/or electric fields provided through the electrode caps 2102. The dielectric coating 2106 can include Parylene, other conformal coating, or other dielectric material that can be situated on the surface 1603.

Figure 23:
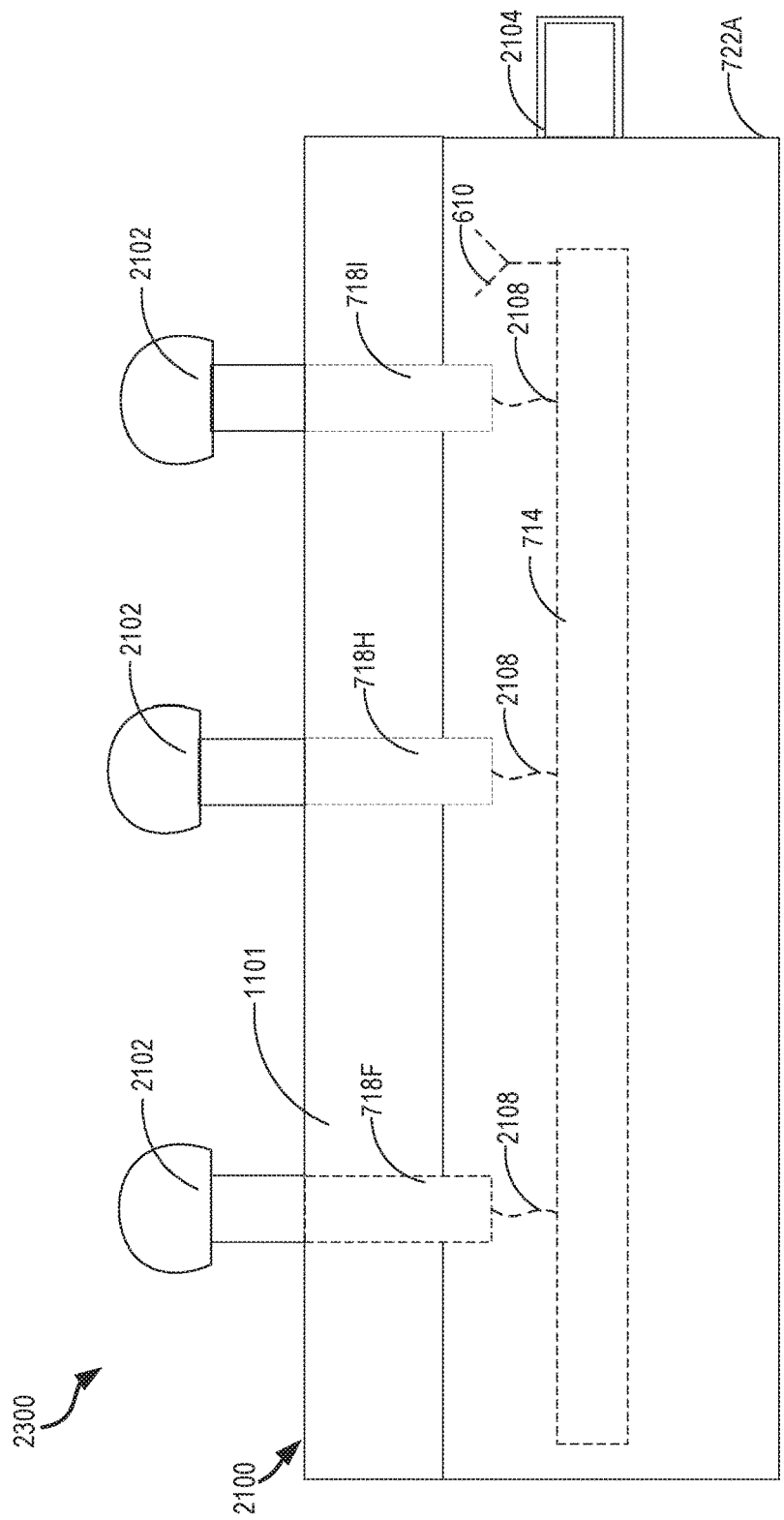
FIG. 23 illustrates generally an example that includes a side view of the multiple-port cap from FIG. 21.

FIG. 23 illustrates generally an example of a side view of an embodiment of a device 2300 that includes the multiple-port cap 2100. The device 2300 includes an enclosure 722A with the cap 2100 situated on and attached to the enclosure 722A, such as to seal the enclosure 722A from moisture or other material intrusion. The circuit board 714 (and associated electric and/or electronic components attached thereto) and the antenna 610 are illustrated as being inside of the enclosure 722A (indicated by the dashed lines). Feedthroughs 718F, 718H, and 718I are electrically connected to the circuit board 714, such as through wire bonds 2108.

Figure 24:
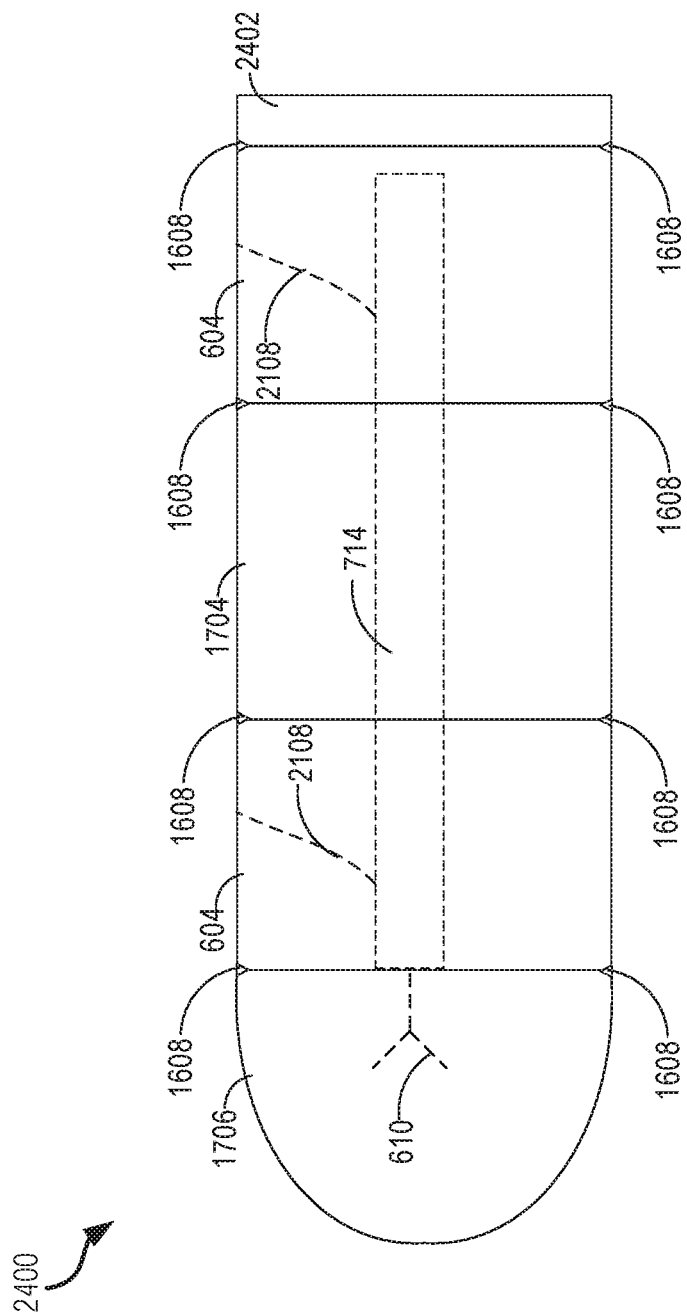
FIG. 24 illustrates generally an example of a side view of an embodiment of an implantable device.

FIG. 24 illustrates generally an example of a side view of an embodiment of an implantable device 2400. The implantable device 2400 can include a dielectric end cap 2406, electrodes 604, a dielectric section 2404, an electrode end cap 2402, welded or brazed material connective material 1608, the circuit board 714, the antenna 610, and electrical connection(s) 2108. The dielectric end cap 2406 can be made of alumina, zirconia, other ceramic material, or the like. The dielectric section 2404 can be made of the same or a different material as the dielectric end cap 2406.

In an example, the electrode end cap 2402 can be made of a conductive material, such as can include a same or similar material as the feedthroughs discussed herein. The dielectric section 2404 can be welded or brazed to the electrodes 604 such as at opposite sides of the dielectric section 2404. Welded or brazed connective material 1608 can be provided at or around a perimeter of the electrodes 604, such as to hermetically seal the circuit board 714 from matter external to the device 2400. In one or more examples, the antenna 610 is provided inside the end cap 2406 and a cap, such as the cap 716 or 2100, can be used to electrically connect the antenna 610 to the circuit board 714. One or more of the embodiments discussed herein can include a hermetically sealed enclosure, such as to include a measured Helium leak rate less than $10^{-9}$ cubic centimeters (cc)-atmosphere (atm)/second (sec) after assembly.

B. Elongated Implantable Assemblies

As similarly discussed elsewhere herein, using an external wireless power transmitter to power an implantable device can be difficult, especially when the implantable device is deeply implanted. Embodiments discussed herein can help overcome such a difficulty, for example using an implantable device with an extended length characteristic. In some embodiments, a distance between a wireless power transmitter (e.g., external to the patient body) and an antenna of an implanted device is less than an implantation depth of electrodes on the implantable device. Some embodiments can include an elongated portion, such as between circuitry housings, that can extend a length of an implantable device.

The present inventors have recognized a need to increase an operating depth for devices that provide neuro stimulation pulses to tissue. Embodiments can allow an implantable device (e.g., an implantable neuro stimulation device) to: (a) deliver therapy pulses to deep nerves (e.g., nerves at the center of a torso or deep within a head, e.g., at a depth greater than ten centimeters); and/or (b) deliver therapy pulses deep within vascular structures requiring stimulation originating from locations deeper than currently available using other wireless technologies. In an example, some structures internal to the body may be within about 10 cm of a surface of the skin, but may nonetheless not be reachable using earlier techniques. This can be because an implant path may not be linear or electrodes of the device may not be able to reach the structure due to bends or other obstacles in the implant path.

The present inventors have recognized that a solution to this implantation depth problem, among other problems, can include an implantable device that is configured to function at various depths by separating proximal circuitry (e.g., circuitry situated in a proximal circuitry housing and generally including communication and/or power transceiver circuitry) into at least two portions, and providing an elongated (e.g., flexible, rigid, or semi-rigid) portion between the two circuitry portions. A more proximal portion of the circuitry (e.g., relative to the other circuitry portion) can include power reception and/or signal conditioning circuitry. A more distal portion of the circuitry (e.g., more distal relative to another circuitry portion) can include stimulation wave production circuitry. The more proximal housing is designated in the following discussion as the first circuitry housing, and the more distal housing is designated as the second circuitry housing.

Electrically sensitive radio frequency (RF) receiving and/or backscatter transmitting circuitry components can be provided or packaged in the proximal first circuitry housing. In an example, a received RF power signal may be rectified to direct current (DC) in the first circuitry housing, such as for use by circuitry disposed in the same or other portions of the assembly. Backscatter transmitting circuitry can optionally be provided. In an example, the first circuitry housing can be maintained within a sufficiently minimal distance to be powered by an external power transmitter, such as a midfield powering device, near field communication, or the like, such as including a midfield powering device described hereinabove.

Figure 25:
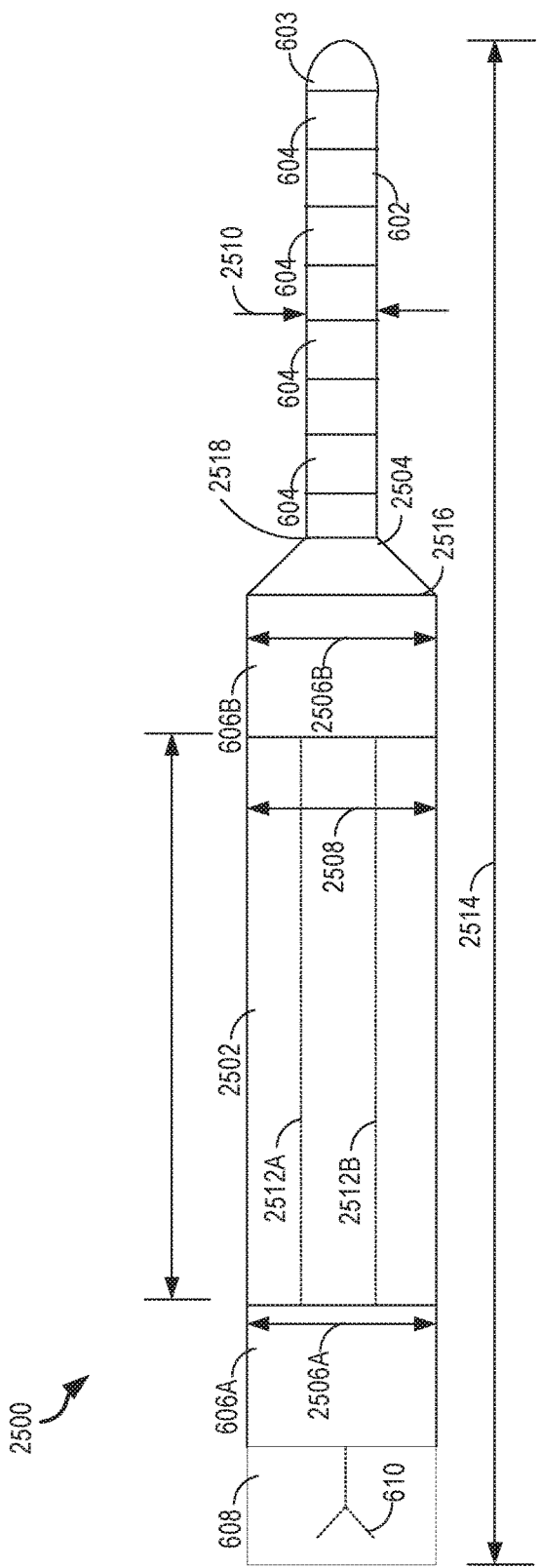
FIG. 25 illustrates generally an example of an elongated implantable device.

FIG. 25 illustrates generally an example of an elongated implantable device 2500. The implantable device 2500 can include an elongated portion 2502, a first circuitry housing 606A, a second circuitry housing 606B, and a connector 2504. In the example of FIG. 25, the connector 2504 is frustoconical, however, other shapes or configurations can similarly be used. The second circuitry housing 606B is optional and the elongated portion 2502 can connect directly to the frustoconical connector 2504. In an example, the first circuitry housing 606A includes communication circuitry, such as for receiving wireless power signals and/or communicating data to or from an external device. Various circuitry in the second circuitry housing 606B can include an application specific integrated circuit (ASIC), large-footprint capacitors, resistors, and/or other components configured to generate therapy signals or pulses, and can electrically connect to the electrodes 604.

The elongated portion 2502 separates the first and second circuitry housings 606A and 606B. The elongated portion 2502 can optionally include conductive material 2512A and 2512B (e.g., one or more conductors) extending therethrough or thereon. In an example, the conductive material 2512A and 2512B can electrically connect a conductive feedthrough of the first circuitry housing 606A to a conductive feedthrough of the circuitry housing 606B. In an example, the conductive material 2512A and 2512B is configured to carry the OUTPUT+ and/or OUTPUT− signals, respectively (see, e.g., FIGS. 27 and 28).

The conductive material 2512A and 2512B can include copper, gold, platinum, iridium, nickel, aluminum, silver, a combination or alloy thereof, or the like. The elongated portion 2502 and/or a coating on the conductive material 2512A and 2512B can electrically insulate the conductive material 2512A and 2512B from a surrounding environment, such as can include body tissue when the device is implanted in a patient body. The coating can include a dielectric, such as an epoxy and/or other dielectric material. The elongated portion 2502 can include a dielectric material, such as a biocompatible material. The dielectric material can include Tecothane, Med 4719, or the like.

In an example, the elongated portion 2502 can be formed from or coated with a material that enhances or increases friction with respect to an expected material within which the device is configured to be implanted (e.g., body tissue). In an example, the materials include silicone. Additionally, or alternatively, a rough surface finish can be applied to a surface, or a portion of the surface, of the elongated portion 2502. A friction-increasing material and/or surface finish can increase friction of the implant relative to the biological tissue in which the implantable device can be implanted. Increasing friction can help the implantable device maintain its position within the tissue. In one or more examples, other small-scale features, such as protrusions (e.g., bumps, fins, barbs, or the like) can be added to increase friction in one direction. Increasing friction can help improve chronic fixation so that the implantable device is less likely to move (e.g., in an axial or other direction) while implanted.

A dimension 2506A (e.g., a width, cross-sectional area, or diameter) of the first circuitry housing 606A can be about the same as a corresponding dimension 2506B (e.g., a width) of the circuitry housing 606B. The elongated portion 2502 can include a first dimension 2508 (e.g., a width) that is about the same as the dimensions 2506A and 2506B of the first and second circuitry housings 606A and 606B, respectively. A second dimension 2510 (e.g., width) of a distal portion of the implantable device 2500 can be less than the dimensions 2506A and 2506B and 2508.

In an example, the distal portion of the implantable device 2500 includes the body portion 602, one or more electrodes 604, and other components coupled to a distal side of a frustoconical connector 2504. A proximal portion of the implantable device 2500 includes the first and second circuitry housings 606A and 606B, the elongated portion 2502, the antenna 610, and other components on a proximal side of the frustoconical connector 2504. The dimensions 2506A and 2506B, 2508, and 2510 as illustrated are generally perpendicular to a length dimension 2514 of the components of the device 2500.

The frustoconical connector 2504 includes a proximal side 2516 coupled to the proximal portion of the implantable device 2500. The frustoconical connector 2504 includes a distal side 2518 coupled to the distal portion of the implantable device 2500. The distal side 2518 is opposite the proximal side 2516. A width or diameter dimension of the distal side 2518 can be about the same as the corresponding dimension 2510 for the body portion 602. A width or diameter dimension of the proximal side 2516 can be about the same as the corresponding dimension 2506A and/or 2506B.

In one or more examples, a length 2514 of the device 2500 can be between about fifty millimeters to about hundreds of millimeters. In one or more examples, the elongated portion 2502 can be between about ten millimeters to about hundreds of millimeters. For example, the elongated portion 2502 can be between about ten millimeters and about one hundred millimeters. In one or more examples, the dimension 2510 can be about one millimeter (mm) to about one and one third mm. In one or more examples, the dimensions 2506A and 2506B can be between about one and a half millimeters and about two and a half millimeters. In one or more examples, the dimensions 2506A and 2506B can be between about one and two-thirds millimeters and about two and one-third millimeters. In one or more examples, the dimension 2508 can be between about one millimeter and about two and a half millimeters. In one or more examples, the dimension 2508 can be between about one millimeter and about two and one-third millimeters.

Figure 26:
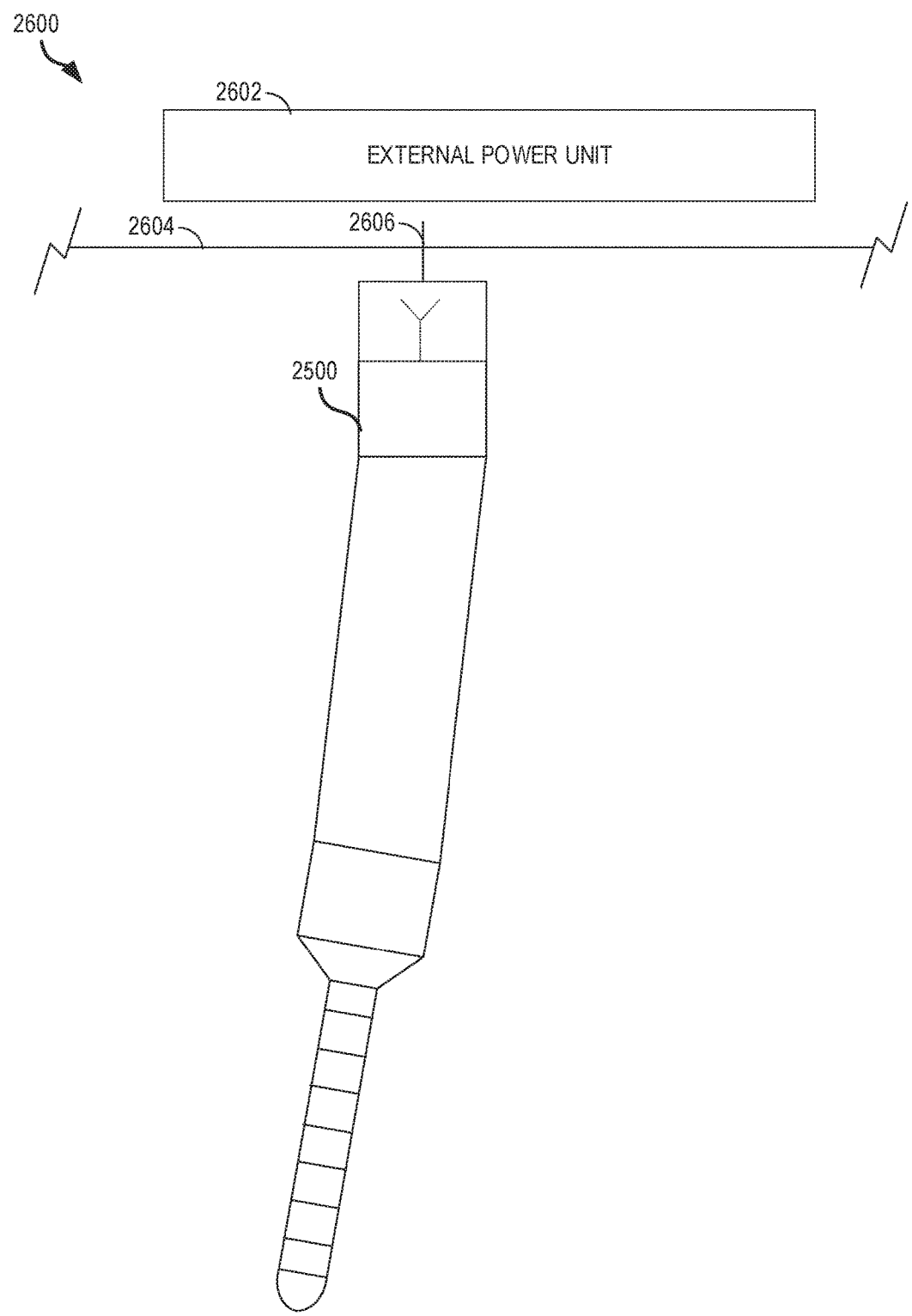
FIG. 26 illustrates generally an example of a system that includes the implantable device from FIG. 25 implanted within tissue.

FIG. 26 illustrates generally an example of a system 2600 that includes the implantable device 2500 implanted within tissue 2604. The system 2600 as illustrated includes the implantable device 2500, tissue 2604, an external power unit 2602, and a wire 2606 (e.g., a push rod, suture, or other component to implant or remove the implantable device 2500). In an example, the external power unit 2602 includes the external source 102.

The elongated portion 2502 of the device 2500 allows the electrodes 604 of the implantable device 2500 to reach deep within the tissue 2604 and allows the antenna to be sufficiently close to the tissue surface and the external power unit 2602. The device 2500 is illustrated with the elongated portion bent, such as to illustrate that the elongated portion can stretch (e.g., a portion is stretchable and/or can be elongated) and/or flex (e.g., can be rotated about one or more axes along the device's length).

In one or more examples, the external power unit 2602 can include a midfield power device, such as the external source 102 described herein. While the circuitry illustrated in FIGS. 27 and 28 is generally configured for midfield powering embodiments, the two-part proximal assembly package (e.g., a device that includes the first and second circuitry housings 606A and 606B with the elongated portion 2502 therebetween) can be applied to other wireless embodiments, including inductive nearfield, far-field, capacitively coupled, and/or ultrasonically powered implantable devices.

Figure 27:
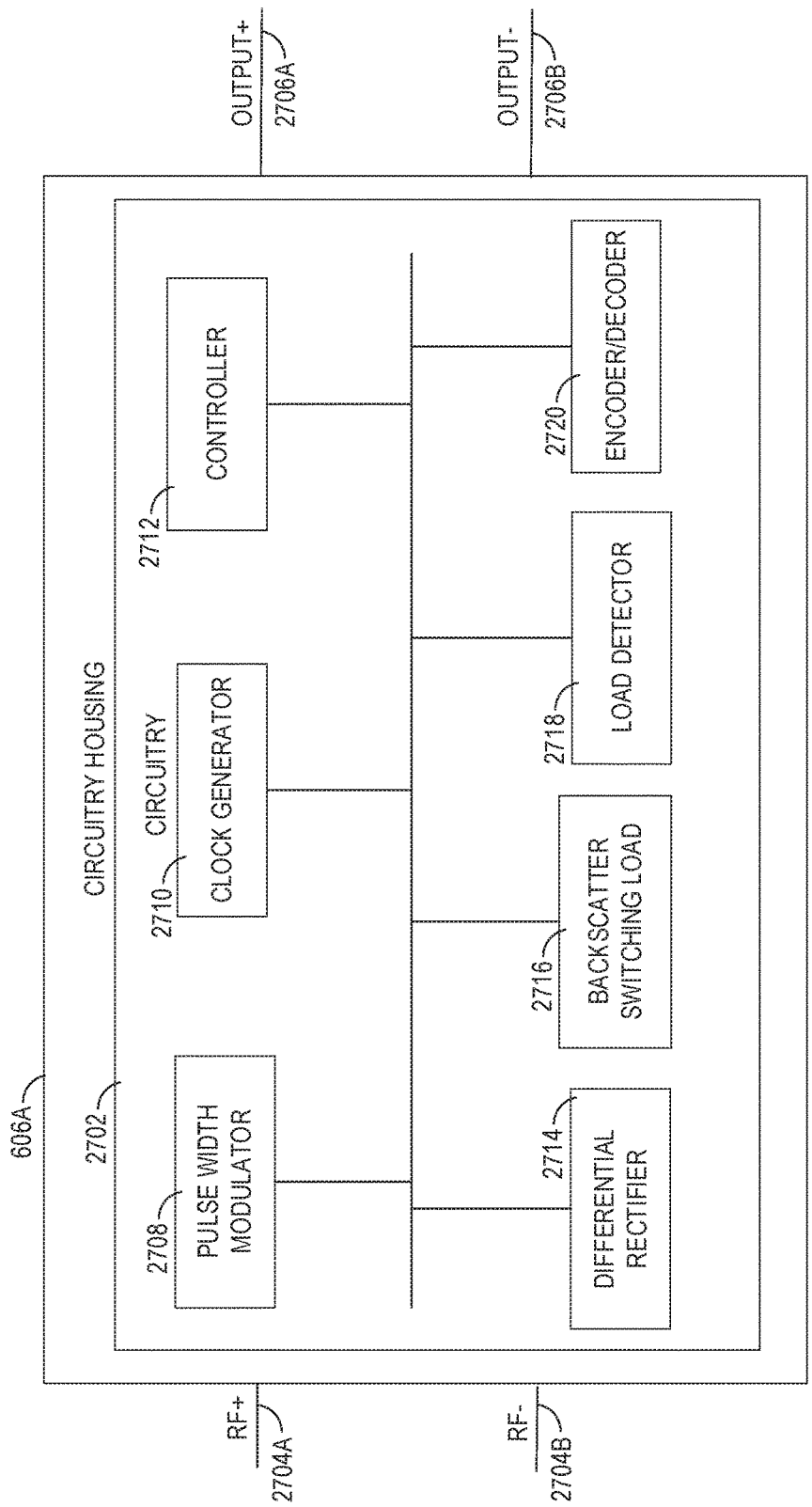
FIG. 27 illustrates generally a schematic example of first circuitry such as can be provided in a circuitry housing.
Figure 28:
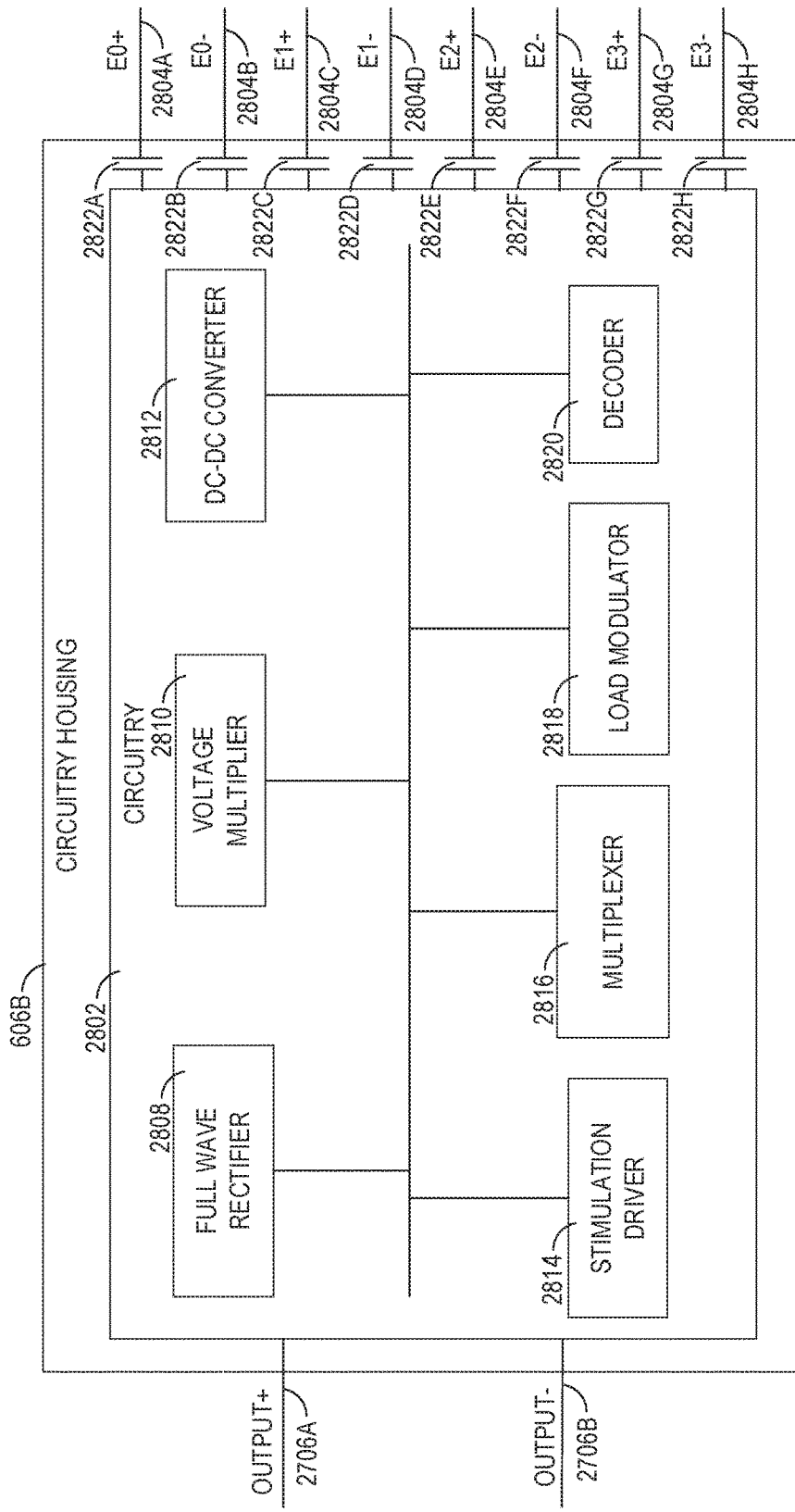
FIG. 28 illustrates generally a schematic example of second circuitry such as can be provided in a circuitry housing.

FIG. 27 illustrates generally a schematic example of first circuitry such as can be provided in the first circuitry housing 606A. The first circuitry housing 606A can be electrically connected to differential radio frequency (RF) lines 2704A and 2704B. The differential RF lines 2704A and 2704B can be electrically connected to respective connections from the antenna 610. In an example, the differential RF lines 2704A and 2704B can be electrically connected to respective feedthrough conductors 718 of the first circuitry housing 606A.

Circuitry 2702 within the first circuitry housing 606A can operate on the differential RF lines 2704A and 2704B to produce a differential RF output on the plus 2706A and minus 2706B lines. The output waveform may be a sinusoidal or square waveform. The output plus 2706A and output minus 2706B lines can be electrically coupled to electrical conductors on another feedthrough of the first circuitry housing 606A. The RF plus line 2704A and RF minus line 2704B can be coupled to feedthroughs that are provided on a first side of the first circuitry housing 606A, such as opposite to feedthroughs on an opposite side of the first circuitry housing 606A to which the output plus 2706A and output minus 2706B lines are connected. The output plus 2706A and output minus 2706B lines can provide a signal that is between about one and ten volts, peak-to-peak, for example. The signals provided on the output plus 2706A and output minus 2706B lines can be charge balanced, such as by one or more components of the circuitry 2702.

At least a portion of circuitry of the implantable device 2500 can be housed within the first circuitry housing 606A. The portion as illustrated is circuitry 2702. The circuitry 2702 can include, among other things, a pulse width modulator 2708, a clock generator 2710, a controller 2712, a differential rectifier 2714, backscatter switching load circuitry 2716, a load detector 2718, and an encoder/decoder circuit 2720. The circuitry 2702 can include other electrical and/or electronic components, such as resistors, transistors, inductors, capacitors, diodes, multiplexers, amplifiers, or the like. These other components can help condition the electrical signals, such as to help ensure that the signals include sufficient voltage, current, or power, such as to help ensure that the current, voltage, or power remain within specified operating ranges of the circuitry 2702.

The pulse width modulator 2708 (sometimes referred to as a pulse duration modulator) encodes a message into a pulse signal. The pulse width modulator 2708 controls power supplied to other components of the circuitry 2702 or 2802. An average value of power (voltage and current) fed to a load can be controlled by altering an amount of time the pulse is high, low, and/or at a ground or reference level potential, that is, by adjusting a duty cycle of the signal.

The clock generator 2710 is a circuit that produces a clock signal. In an example, the controller 2712 and other clocked components can use the clock signal to time its operations. The clock signal produced by the clock generator 2710 can include a square wave, or other wave with a rising edge and/or a falling edge. Basic circuitry included in a clock generator generally includes a resonator and an amplifier. The clock signal generated by the clock generator 2710 can be within a Megahertz range, but other ranges can similarly be used or provided by the circuit.

The controller 2712 provides control signals that configure other circuitry to perform operations in accord with the control signals. For example, the controller 2712 can configure a duty cycle provided by the pulse width modulator 2708, or can configure whether the backscatter switching load provides a signal to the antenna 610 for transmitting to the external power unit 2602, or the like.

The differential rectifier 2714 receives an alternating current (AC) signal and produces a DC signal. A capacitor can be coupled to an output of the differential rectifier 2714, such as to help smooth the output. The connections between and/or circuitry of the first and second circuitry housings 606A and 606B can help transfer energy from one of the housings to the other such as without exposing any non-hermetically encased signal processing circuitry to a non-charge balanced signal.

The backscatter switching load circuitry 2716 can switch between a receive mode and a transmit mode. The backscatter switching load circuitry 2716 can receive power from the external power unit 2602 (in receive mode). The backscatter switching load circuitry 2716 can transmit reflected power from the external power unit 2602 back to the antenna 610, such as to transmit the reflected power to the external power unit 2602. The reflected power can encode data communications from the implantable device 2500 to the external power unit 2602. In an example, the encoded data includes information about a power transfer efficiency between the device 2500 and the external power unit 2602.

The load detector 2718 detects whether and/or how much power is drawn by circuitry 2702, circuitry 2802 (see FIG. 28), or other components of the device 2500. The controller 2712 can use an output of the load detector 2718 to adjust a PWM duty cycle or other parameter of the circuitry 2702.

The encoder/decoder circuit 2720 can be configured to convert data from one format to another format. The encoder/decoder circuit 2720 receives a rectified wave and determines whether configuration data or other data is embedded in the rectified wave. The encoder/decoder circuit 2720 can receive a backscatter signal, such as from the backscatter switching load circuitry 2716 and encode the signal with data to be transmitted to the external power unit 2602.

FIG. 28 illustrates generally a schematic example of second circuitry such as can be provided in the circuitry housing 606B. Although particular examples or types of circuitry are discussed as being in a particular one of the first and second circuitry housings 606A and 606B, the various circuits can optionally be provided in either location depending on various design constraints and optimizations.

In the example of FIG. 28, the second circuitry housing 606B is electrically connected to the output plus 2706A and the output minus 2706B lines from the first circuitry housing 606A (see, e.g., FIG. 27). The output plus 2706A and output minus 2706B lines can be electrically connected to respective connections from within the first circuitry housing 606A. In an example, the output plus 2706A and output minus 2706B lines can be electrically connected to respective feedthrough conductors 718 of proximal sides the second circuitry housing 606B.

A portion of circuitry of the implantable device 2500 can be housed within the second circuitry housing 606B. The portion as illustrated in FIG. 28 includes various circuitry 2802. The circuitry 2802 includes a full wave rectifier 2808, a voltage multiplier 2810, a DC-DC converter 2812, a stimulation driver 2814, a multiplexer 2816, a load modulator 2818, and a decoder 2820. The circuitry 2802 can include other electrical and/or electronic components, such as resistors, transistors, inductors, capacitors, diodes, multiplexers, amplifiers, or the like. These other components can help condition various electrical signals, such as to help ensure that the signals include sufficient voltage, current, or power, such as to ensure that the current, voltage, or power remain within specified operating ranges of the circuitry 2802. The second circuitry housing 606B can further include or provide a housing for capacitors 2822A, 2822B, 2822C, 2822D, 2822E, 2822F, 2822G, and 2822H. In an example, the capacitors 2822A-2822H can help remove undesired high frequency components from stimulation signals, such as can be present on electrode conductor lines 2804A, 2804B, 2804C, 2804D, 2804E, 2804F, 2804G, and/or 2804H, respectively. In an example, the capacitors 2822A-2822H can block direct current voltages on respective electrode lines 2804A-2804H, respectively.

A full wave rectifier can convert a wave signal, such as a sine wave signal, to a signal that includes one of positive or negative components (and ground). In an example, the full wave rectifier 2808 converts a wave that is positive, negative, or both, to a wave that includes only one of positive or negative components.

The voltage multiplier 2810 includes electrical circuitry that converts an AC power signal from a low voltage to a higher DC voltage. The DC-DC converter 2812 includes circuitry that converts a DC voltage signal to a different voltage.

The stimulation driver 2814 includes circuitry that configures other circuitry 2802 to provide stimulus to the tissue 2604. The stimulation driver 2814 can provide signals to the multiplexer 2816, and the multiplexer 2816 can in turn select which of lines 2804A, 2804B, 2804C, 2804D, 2804E, 2804F, 2804G, and 2804H to use to provide stimulation and/or to use for electrical signal sensing. In an example, a control signal input to the multiplexer 2816 indicates which electrode(s) 604 provide a cathode and which electrode(s) 604 provide an anode for signals provided by the stimulation driver 2814.

The load modulator 2818 can vary a frequency of a signal provided as a stimulus. In an example, the load modulator 2818 can adjust a duty cycle of the signal provided as stimulus.

The decoder 2820 can be configured to convert data signals. In an example, the decoder 2820 is configured to change a format of data provided on the output plus 2706A and output minus 2706B lines from the circuitry 2702 to a format compatible with another component, such as a component provided in the first and/or second circuitry housings 606A and 606B, and/or the external power unit 2602.

Figure 29:
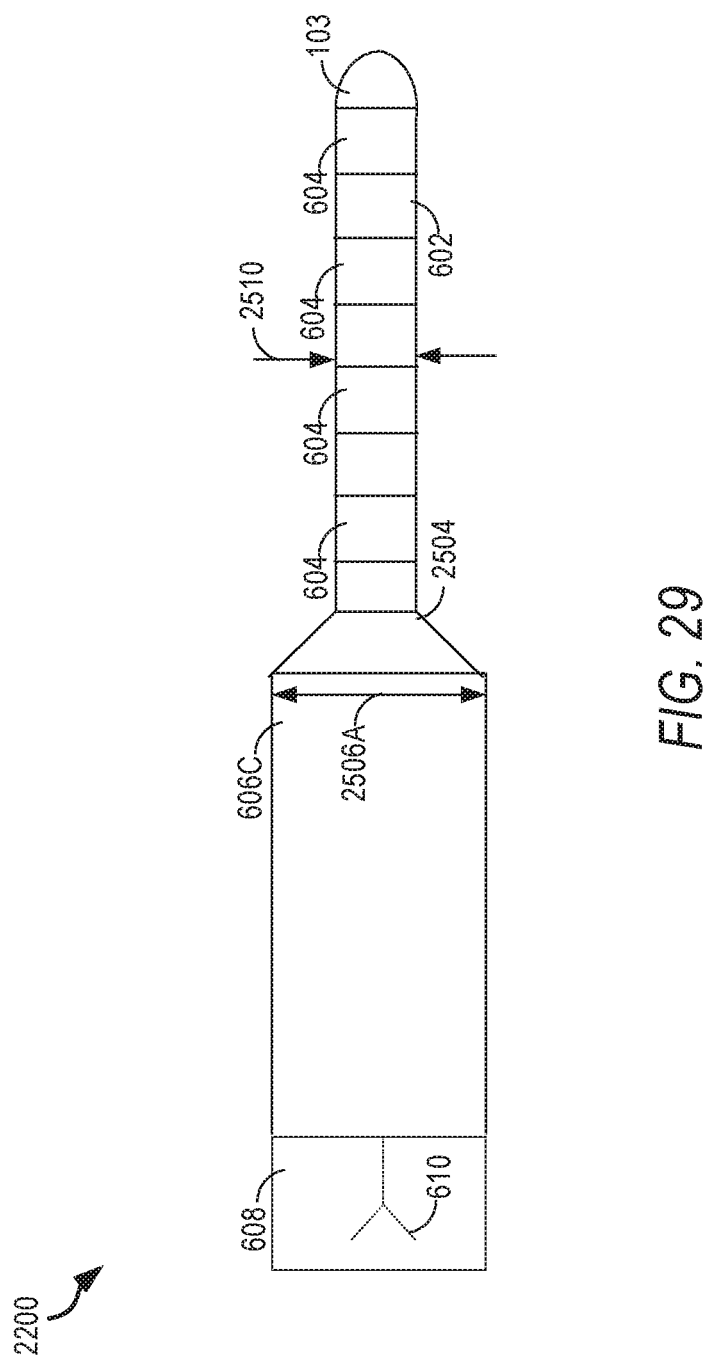
FIG. 29 illustrates generally an example of an elongated implantable device.

FIG. 29 illustrates generally an example of an elongated implantable device 2900. The device 2900 is similar to the device 2500 described above in the example of FIG. 25, however the device 2900 includes a single circuitry housing 606C. That is, the device 2900 does not include the elongated portion 2502 from the example of FIG. 25. Instead, the device 2900 includes the various implantable device circuitry (see, e.g., circuitry 2702 of FIG. 27 and circuitry 2802 of FIG. 28) in the single circuitry housing 606C.

In the example of FIG. 29, the device 2900 includes the frustoconical connector 2504, such as connected between the body portion 602 and the single circuitry housing 606C. Differently dimensioned embodiments of the frustoconical connector 2504 can be used to provide differently dimensioned devices, such as with respect to the circuitry housings and/or distal lead sections (e.g., the body portion 602 and electrodes 604) of the devices. In an example, the frustoconical connector 2504 is configured to aid implant procedures, such as by helping to gradually widen an incision as the device is inserted, which in turn can help to reduce patient discomfort.

C. Injectable and/or Nerve-Wrapping Implantable Assemblies

Various embodiments described herein include electrode systems deployable inside of a patient body, such as at a neural target for electrostimulation therapy delivery. In an example, an implantable electrode system can include an elongated assembly body configured to house electrostimulation circuitry or sense circuitry, and an electrode assembly coupled to the electrostimulation circuitry or sense circuitry and configured to provide electrostimulation to, or sense electrical signal activity from, the neural target inside of the patient body. In an example, the electrode assembly includes multiple elongate members that extend away from the assembly body in a predominately longitudinal direction. The electrode assembly can have a retracted first configuration when the electrode assembly is inside of a deployment sheath or cannula, and an expanded second configuration when the electrode assembly is outside of the cannula. In an example, an electrode assembly can include a further expanded third configuration in which the electrode assembly receives or encloses a neural target. A neural target can include a nerve, or other tissue such as a vein, connective tissue, or other tissue that includes one or more neurons within or near the tissue.

In an example, an electrode having a cuff configuration can be used to surround all or a portion of a nerve, such as to provide an electrostimulation therapy to the nerve using the electrode. Such a cuff electrode can be positioned near, or attached to, the nerve using various techniques. For example, a cuff electrode can be tied around a nerve using sutures. Such tying can require two-handed manipulation and can be tedious and difficult for a clinician to install.

In an example, a cuff electrode can have a helical shape. Such a helical cuff electrode can be wrapped around a nerve to install it. Relative to a tied cuff electrode, a relatively long length or section of a nerve segment is used with a helical cuff electrode because of the way the nerve is wrapped by the helical structure. Accordingly, a relatively long length of nerve must be dissected to provide access for the electrode, which can potentially cause nerve damage if installation is improper.

Implantation of tied or helical cuff electrodes is typically performed using two-handed installation techniques and open surgery. Although some suturing can be performed laparoscopically, such a procedure can be tedious, difficult, and invasive. Furthermore, cuff electrodes can be too large to insert by injection or using laparoscopic tools, and accordingly other surgical openings can be required.

Cuff electrodes can be manufactured in different sizes, and the clinician or installer can select an appropriately sized electrode at the time of implant, such as based on intra-operative measurement of a destination nerve. This adds time and complexity to an installation operation.

In addition to addressing the problems above, there is an ongoing desire to reduce a displacement volume of implantable neural stimulation, or neuro stimulation, devices. Miniaturization of such devices can allow for an easier and less invasive implant procedure, reduce a surface area of the implantable device which can in turn reduce a probability of a post-implant infection, and can help ensure long-term patient comfort.

In an example, solutions to the various problems associated with traditional cuff electrodes can be addressed using injectable nerve-wrapping electrodes. In an example, such a nerve-wrapping electrode can be leadless, and can be wirelessly coupled with one or more other devices using midfield wireless communication techniques, such as to transfer power or data. Midfield powering technology, including transmitters, transceivers, implantable devices, circuitry, and other details are discussed generally herein at FIGS. 1-5.

In an example, a nerve-wrapping electrode can address the various problems described above, among others, by including or using one or more of an improved attachment mechanism that responds to a force applied in at least one direction, includes electrodes that are expandable and retractable, and can be installable in a patient body at a target location using an injectable sheath or cannula. In an example, various portions of the nerve-wrapping electrode can be elastic or flexible to conform to a variety of body structures or target location physiologies.

In an example, a folded, deformable, or conformable electrode assembly can be pushed through a sheath and then deployed at a target location in a body at or near a nerve site.

The electrode assembly, or an electrode itself, can have an elastic or spring quality that causes the electrode assembly, or causes another portion of the assembly appurtenant to one or more electrodes, to expand when it is deployed outside of the installation sheath. In other examples, the electrode assembly and/or electrode itself need not splay or flex to accommodate a neural target such as when the target is sufficiently narrow or the electrode(s) are sufficiently open to receive the target.

In an example, a non-deployed electrode can have a length characteristic that is related to its diameter when the electrode is deployed. For example, a longer electrode can have a larger deployed diameter than a shorter electrode. In this manner, a deployed electrode structure can have a relatively larger diameter in some respects than the diameter of a sheath used to deploy the electrode structure.

In an example, a nerve can be disposed at or around an artery or tendon. In such cases, a large diameter cuff can be used to sufficiently surround the nerve and its surrounding tissue. Using the deployable nerve-wrapping electrode, the large diameter can be attained without using open surgery to install a large traditional cuff or helical electrode.

In an example, a nerve-wrapping electrode remains flexible, or expandable and retractable, such as after installation. Therefore, the nerve-wrapping electrode may not constrict a pulsating artery. In some examples, however, if a nerve-wrapping electrode is too loose or too easily expanded, then the electrode may not provide optimal surface area contact with the target tissue, and therefore it may use more or variable power to elicit the same response from a target.

In an example, two or more electrodes can be delivered concurrently using the same sheath, according to various embodiments described herein. For example, the two or more electrodes can be arranged in parallel such that they are provided in a side-by-side manner about a target nerve. The electrodes can be placed in a variety of configurations to stimulate across the target transversely or axially. In an example, the multiple electrodes can be used for electrical blocking or electrical activity sensing and recording. In an example, the electrodes, or portions of the same electrode, can be aligned such that distal portions of the electrodes are, or can be made to be, touching. In other examples, the electrodes can be offset from one another such that their distal portions do not touch in compressed or in uncompressed configurations.

In an example, the nerve-wrapping electrode can be integrated with a power transfer system (e.g., a wireless power transfer system) and electronics, or it can be lead-based.

In an example, the nerve-wrapping electrode can be a part of an electrode deployment system that includes a joint configured to arrange the electrode's drive assembly parallel to the nerve.

These and other features of the various implantable devices and electrode configurations are discussed herein with reference to various figures. Various combinations of the embodiments shown are also contemplated by the present inventors.

In an example, the circuitry housing 606 (see, e.g., FIG. 6, or other embodiments of the circuitry housing discussed herein) can include electric or electronic components for providing stimulation to the patient in which the implantable device is implanted. Also, as previously discussed, the circuitry housing can include one or more feedthroughs such as to seal the circuitry housing 606 and/or provide electrical signals from within the circuitry housing 606 to other circuitry external to the housing. The feedthroughs can have a minimal surface area to help reduce a volume of the implantable device. Miniaturizing the feedthroughs, however, can be quite challenging. For example, problems can be realized in forming a plate with feedthroughs where the plate includes a diameter that is less than 3 millimeters. The materials and process used in creating the feedthroughs and/or housing assemblies can be important in creating such a miniaturized cap, such as described herein.

By reducing the diameter of the feedthroughs and housing end caps, the implantable device can require or use a relatively smaller opening in a patient than for previous implantable devices. A cannula or sheath (e.g., including a lumen through which the implantable device is inserted into a patient) can be made with a smaller diameter as well. In some examples, the implantable device can be sufficiently small to allow an implant procedure without a cannula. In one or more examples, a body portion 602 that includes electrodes (e.g., ring electrodes) situated thereon can be replaced with respective electrodes on or in the circuitry housing 606 and/or on one or more end caps for the housing. Such a configuration can reduce an overall length of the implantable device, reduce displacement volume of the implantable device, reduce risk of implant infection, and/or reduce a cost of manufacture for the implantable device.

In an example, one or more electrodes can extend from the circuitry housing 606 and/or from the body portion 602 of the implantable device 600. Although reference is made in this and other discussions herein to the implantable device 600, other embodiments of the implantable device, such as discussed elsewhere herein, can similarly be used. The electrodes can extend away from the body portion 602 substantially in the direction of the longitudinal axis of the body portion 602 (such as rather than transversely to the body portion 602). The longitudinally-extending electrodes can thus be used without impeding the device from traveling or sliding through a cannula for delivery to a neural target.

FIGS. 30A and 30B illustrate generally different views of an example 3000 of an implantable electrode assembly 3001 inside of a cannula 3010. The implantable electrode assembly 3001 includes a body portion 3002 and an electrode portion 3003. The electrode portion 3003 includes one or more discrete electrodes that extend in the direction of a longitudinal axis of the cannula 3010 away from the body portion 3002 of the implantable electrode assembly 3001.

In an example, the electrode portion 3003 includes multiple electrodes. At least one of the electrodes can be flexible. In an example, the electrode portion 3003 is configured to receive and retain a neural target (e.g., a nerve, or a nerve bundle) or other biological tissue target. FIG. 30B illustrates generally a perspective view of the example 3000, including the electrode portion 3003 inside of the cannula 3010.

In an example, the electrode portion 3003 is compressed inside of the cannula. When the electrode portion 3003 is compressed, extension members of the electrode portion 3003 are elongated and can be held in the compressed configuration such as by the inner side walls of the cannula 3010.

Figure 30C:
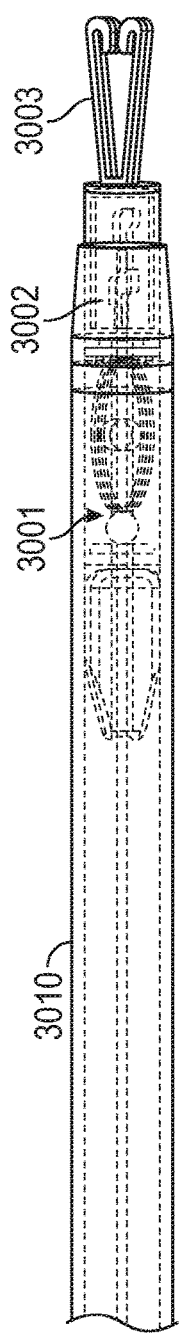
FIG. 30C illustrates generally an example of an implantable electrode assembly partially outside of a cannula.

FIG. 30C illustrates generally an example of the implantable electrode assembly 3001 partially outside of the cannula 3010. In the example of FIG. 30C, the electrode portion 3003 is uncompressed, or extended. When the electrode portion 3003 exits the cannula, a retention force (such as provided by the side walls of the cannula 3010) acting on the extension members of the electrode portion 3003 is removed, and the extension members can expand or recoil away from each other. That is, the extension members can extend transversely away from the longitudinal axis of the cannula 3010 when the electrode portion 3003 is unencumbered by the walls of the cannula 3010.

Figure 30D:
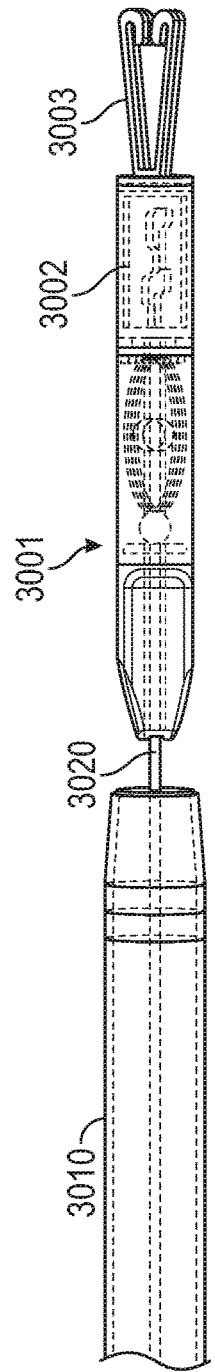
FIG. 30D illustrates generally an example of an implantable electrode assembly deployed from a cannula and coupled to a push rod.

FIG. 30D illustrates generally an example of the implantable electrode assembly 3001 deployed from the cannula 3010 and coupled to a push rod 3020. In an example, a proximal end of the implantable electrode assembly 3001 is configured to receive the push rod 3020, and the push rod 3020 urges the implantable electrode assembly 3001 down a lumen of the cannula 3010.

Figure 30E:
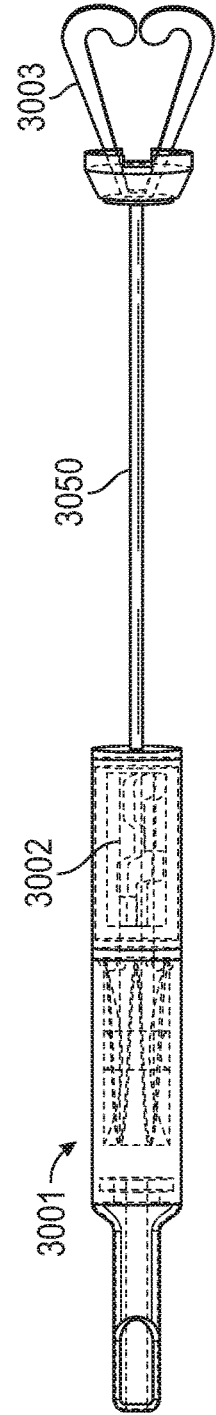
FIG. 30E illustrates generally an example of an implantable electrode assembly including an intermediate lead.

FIG. 30E illustrates generally an example of the implantable electrode assembly 3001 including an intermediate lead 3050. In the example of FIG. 30E, the electrode portion 3003 can be coupled to the body portion 3002 by way of an intermediate lead 3050 that includes electrical conductors that couple drive circuitry in the body portion 3002 with one or more discrete electrodes in the electrode portion 3003. In an example, the body portion 3002 can include, use, or be configured similarly to the circuitry housing 606 (such as including one or more of the first circuitry housing 606A, the second circuitry housing 606B, the single circuitry housing 606C, etc.).

FIG. 31A illustrates generally a first example 3110 of the implantable electrode assembly 3001 approaching a first neural target 3115. In the example of FIG. 31A, the electrode portion 3003 is shown in a first extended configuration (e.g., outside of a delivery cannula) wherein at least some part(s) of the extension members of the electrode portion 3003 are spaced apart by a greater distance relative to a compressed configuration. In the example of FIG. 31A, a first force acts in a first direction 3101 on the implantable electrode assembly 3001, such as by the push rod 3020.

FIG. 31B illustrates generally a second example 3120 of the implantable electrode assembly 3001 with nerve-wrapping electrodes flexing away from the first neural target 3115. In FIG. 31B, the implantable electrode assembly 3001 is adjacent to, and the outer distal edge of the electrode portion 3003 impinges on, the first neural target 3115. In response to the first force continuing to act in the first direction 3101, the extension members of the electrode portion 3003 can be driven or pushed apart such that the first neural target 3115 can be engaged, received, or accepted between the extension members. That is, a second force can act in a second direction 3102 when the electrode portion 3003 is driven against the first neural target 3115.

FIG. 31C illustrates generally a third example 3130 of the implantable electrode assembly 3001 with nerve-wrapping electrodes provided about the first neural target 3115. In the example of FIG. 31C, the electrode portion 3003 grasps and retains the first neural target 3115. A spring force or retention force acts in a third direction 3103 (e.g., substantially oppositely to the second direction 3102) to push or retract the extension members of the electrode portion 3003 back together, or toward one another, such as toward the first extended configuration shown in FIG. 31A.

FIGS. 32A, 32B, and 32C illustrate generally examples of using a different flexible electrode configuration to receive and retain a second neural target 3215. The second neural target 3215 can be the same or different neural target than the first neural target 3115. The example of FIG. 32A illustrates generally an example 3210 of an implantable electrode assembly with a hook-shaped nerve-wrapping electrode assembly 3253 adjacent to the second neural target 3215.

FIG. 32B illustrates an example 3220 with the implantable electrode assembly with the hook-shaped nerve-wrapping electrode assembly 3253 flexing away from the neural target 3215 to provide access to a neural target retention region 3260 that is encircled or enclosed at least in part by the electrode assembly 3253. That is, a distal or end portion of the hook-shaped nerve-wrapping electrode assembly 3253 can flex, stretch, or otherwise extend to expose the retention region 3260 to thereby receive the second neural target 3215 therein. FIG. 32C illustrates generally an example 3230 of the electrode assembly with hook-shaped nerve-wrapping electrode assembly 3253 provided about the second neural target 3215, that is, with the second neural target 3215 seated in the nerve retention region 3260.

Figure 33A:
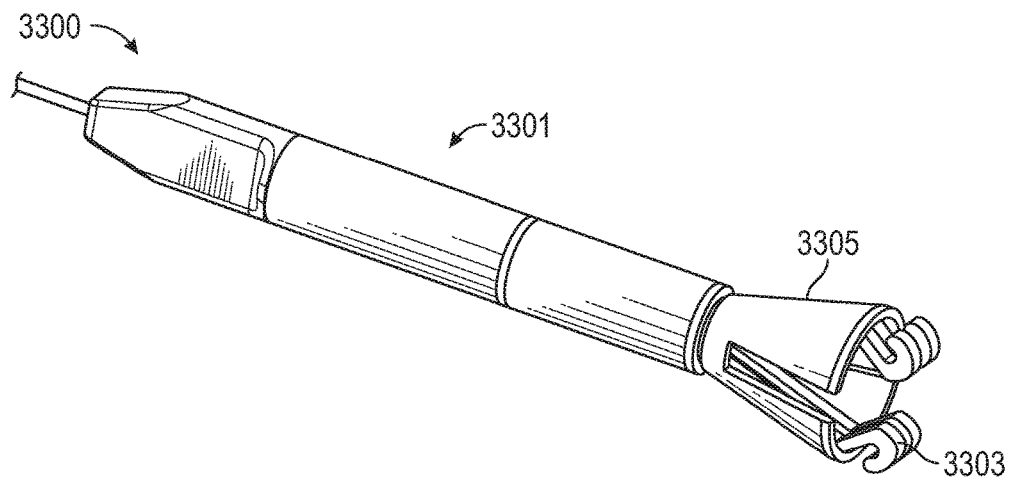
FIGS. 33A and 33B illustrate generally side and perspective views, respectively, of a second implantable electrode assembly.
Figure 33B:
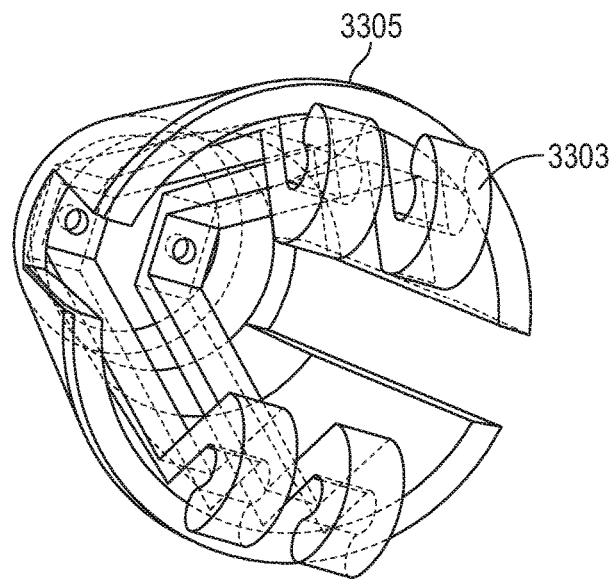

FIGS. 33A and 33B illustrate generally side and perspective views, respectively, of a second implantable electrode assembly 3301. The second implantable electrode assembly 3301 includes a distal portion having second nerve-wrapping electrodes 3303 and an electrode insulator member 3305. In an example, the second nerve-wrapping electrodes 3303 includes one or more discrete electrodes that extend in the direction of a longitudinal axis of the second implantable electrode assembly 3301. At least one of the electrodes can be flexible, and the electrodes can be configured to receive and retain a neural target (e.g., a nerve, or a nerve bundle) or other biological tissue target.

The electrode insulator member 3305 is configured to electrically isolate the electrodes from surrounding, non-targeted tissue at or near an implantation site. In an example, the electrode insulator member 3305 is made at least in part from silicone or from another non-conductive and biocompatible material. In an example, the electrode insulator member 3305 is flexible and can be conformable to a shape or extension configuration of the electrodes that it surrounds. In an example, the electrode insulator member 3305 includes a slit through which a neural target is configured to reside when the second implantable electrode assembly 3301 is installed about the target. The electrode insulator member 3305 can be used with any electrode embodiment discussed herein, or the member can be unused. In an example, the electrode insulator member 3305 can help prevent damage to, or signal interference from, nearby tissue.

Figure 34:
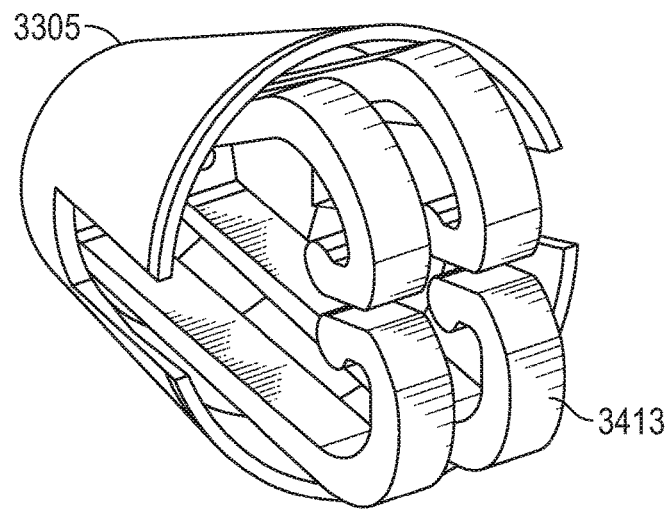
FIG. 34 illustrates generally an example that includes nerve-wrapping electrodes and an electrode insulator member.

FIG. 34 illustrates generally an example of another embodiment of nerve-wrapping electrodes 3413 and the electrode insulator member 3305. In the example of FIG. 34, the nerve-wrapping electrodes 3413 include an inwardly-facing hook-shaped distal portion that can be helpful for retaining a target tissue when the assembly is installed in a patient. The examples of FIGS. 33A and 33B include the nerve-wrapping electrodes 3303 which can include an outwardly-facing hook-shaped distal portion that can include a gap or spacing to help facilitate coupling with a tissue target, such as a larger-diameter neural target.

Figure 35A:
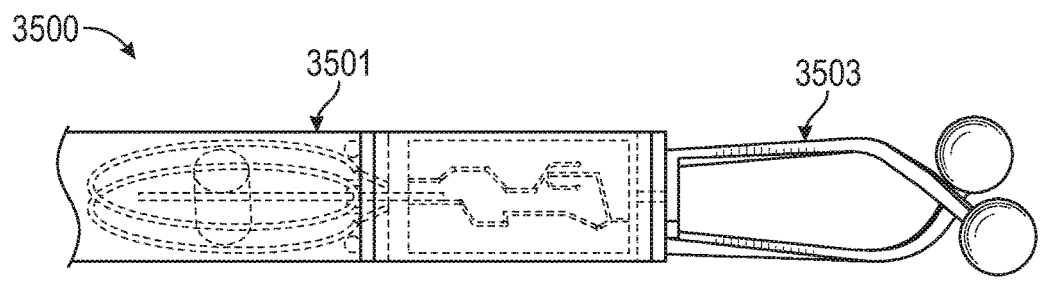
FIGS. 35A and 35B illustrate generally side and perspective views, respectively, of a third implantable electrode assembly.
Figure 35B:
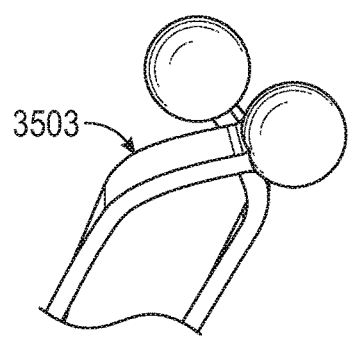

FIGS. 35A and 35B illustrate generally side and perspective views, respectively, of a third implantable electrode assembly 3501. The third implantable electrode assembly includes a third embodiment of nerve-wrapping electrodes 3503. The third embodiment of nerve-wrapping electrodes 3503 can include a pair of flexible, elongate conductors, and each conductor can extend away from a body portion of the assembly 3501 in a longitudinal direction of the body portion. In an example, each conductor terminates, at its distal end, in a bulbous end portion. The conductors can be flexible and can include a turned or bent portion. In an example, each of the conductors turns or bends toward a longitudinal axis of the body, and/or toward the other one of the conductors. In an example, the conductors turn or extend substantially along a helical path, and the third implantable electrode assembly 3501 is configured for installation by turning or twisting the assembly about a neural target to seat the neural target between the conductors.

Figure 36:
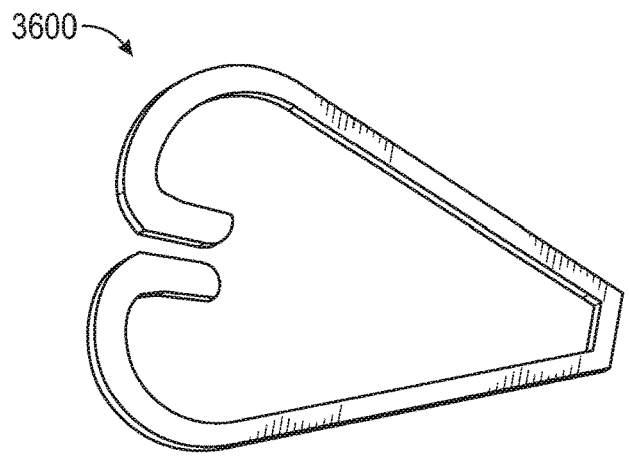
FIG. 36 illustrates generally an example of an implantable electrode.

Various other implantable electrode assembly configurations can similarly be used or applied, such as using the same or similar cannula-based delivery system as described above in the examples of FIGS. 30A-35B, and such as using the cannula 3010. For example, FIG. 36 illustrates generally a fourth implantable electrode 3600. The fourth implantable electrode 3600 can be used together with a body portion (e.g., the body portion 3002) of an implantable assembly. The example of the fourth implantable electrode 3600 includes a pair of hook-shaped electrode members. The members can be adjacent or offset from one another, and in some examples one or more of the members can be flexible or configured to move relative to one another, such as to facilitate reception of a neural target between the members.

Figure 37:
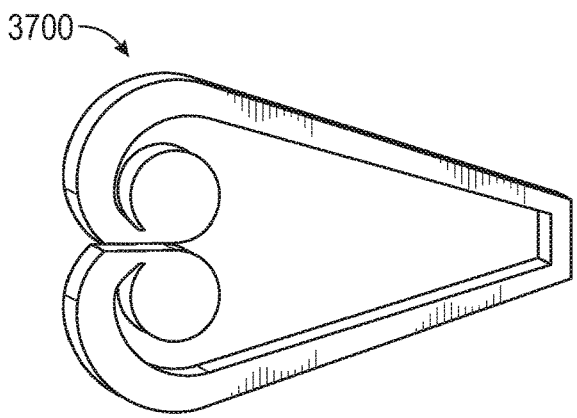
FIG. 37 illustrates generally an example of an implantable electrode.

FIG. 37 illustrates generally a fifth implantable electrode 3700. The fifth implantable electrode 3700 can be used together with a body portion (e.g., the body portion 3002) of an implantable assembly. The example of the fifth implantable electrode 3700 includes a pair of hook-shaped electrode members with bulbous end features. The members can be adjacent or offset from one another, and in some examples one or more of the members can be flexible or configured to move relative to one another, such as to facilitate reception of a neural target between the members.

Figure 38:
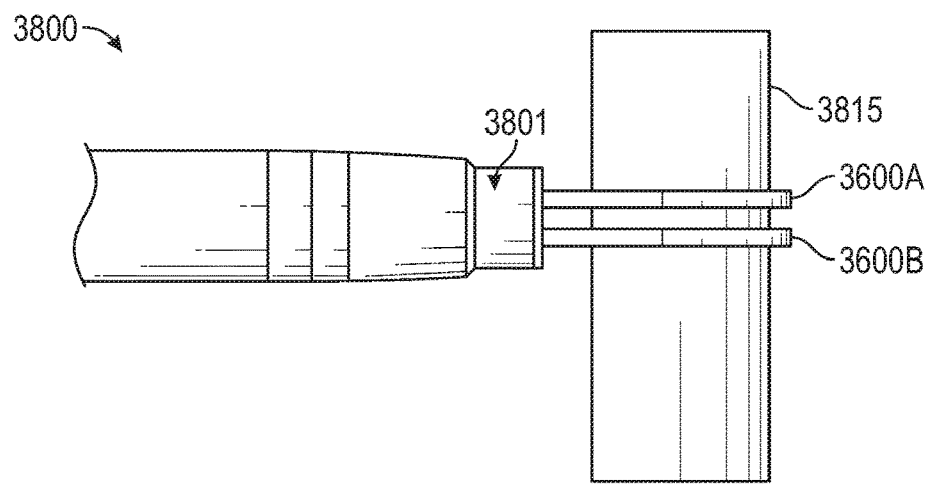
FIG. 38 illustrates generally an example of an implantable electrode assembly configured to deliver an electrostimulation axially to a neural target.

FIG. 38 illustrates generally an example 3800 of an implantable electrode assembly 3801 configured to deliver an electrostimulation axially to a neural target 3815. In the example 3800, the implantable electrode assembly 3801 includes first and second electrodes 3600A and 3600B that are axially spaced apart along a longitudinal axis of the neural target 3815. In an example, the first and second electrodes 3600A and 3600B include respective instances of the fourth implantable electrode 3600 discussed above, such as coupled to a cannula-delivered body portion 3002 of an implantable device. The first and second electrodes 3600A and 3600B can be separately or individually addressable by drive circuitry (see, e.g., the stimulation driver 2814 in the example of FIG. 28) in a housing of the implantable electrode assembly 3801. In an example, one of the first and second electrodes 3600A and 3600B is configured as an anode and the other is configured as a cathode for use in providing an electrostimulation therapy to the neural target 3815.

Figure 39:
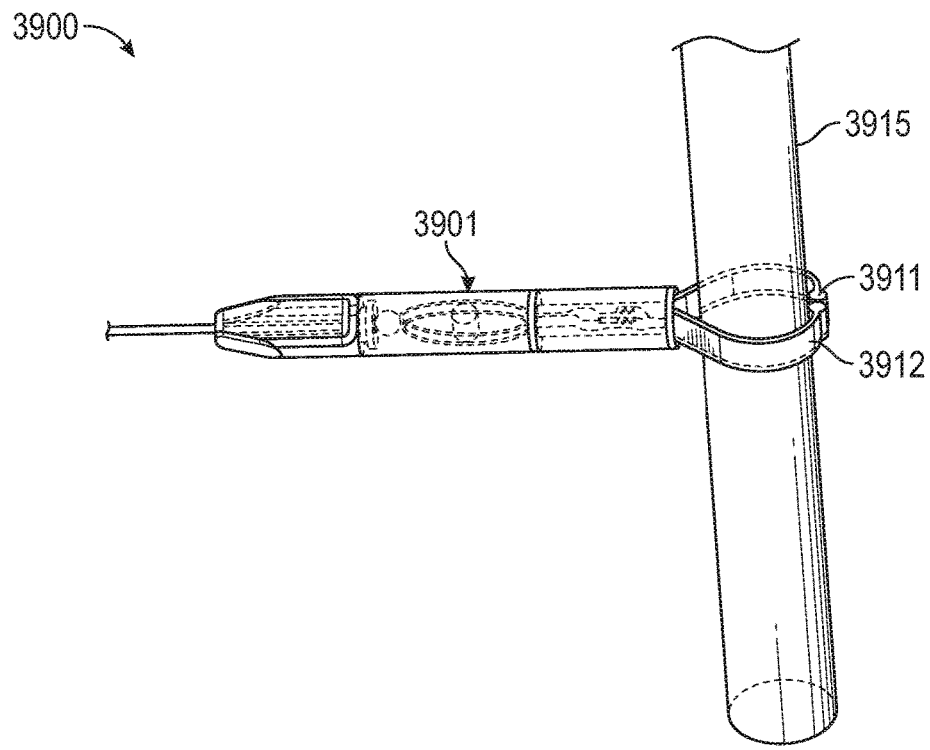
FIG. 39 illustrates generally an example of an implantable electrode assembly configured to deliver an electrostimulation transversely to a neural target.

FIG. 39 illustrates generally an example 3900 of an implantable electrode assembly 3901 configured to deliver an electrostimulation transversely to a neural target 3915. In the example 3900, the implantable electrode assembly 3901 includes first and second electrodes 3911 and 3912 that are spaced apart from each other. In the illustrated installed configuration, the first and second electrodes 3911 and 3912 are provided adjacent to opposite sides of the neural target 3915. The first and second electrodes 3911 and 3912 can be separately or individually addressable by drive circuitry (see, e.g., the stimulation driver 2814 in the example of FIG. 28) in the housing of the implantable electrode assembly 3901. In an example, one of the first and second electrodes 3911 and 3912 is configured as an anode and the other electrode is configured as a cathode for use in providing an electrostimulation therapy to the neural target 3915.

Figure 40:
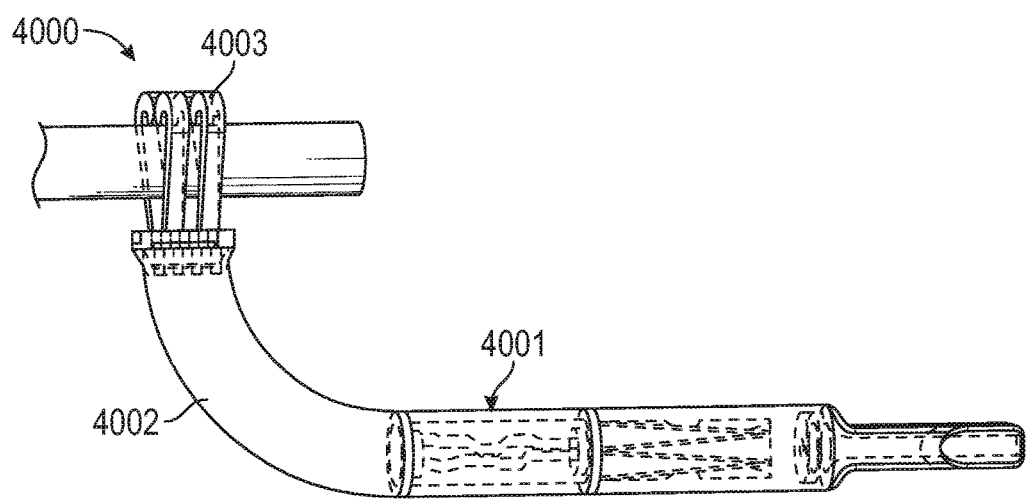
FIG. 40 illustrates generally an example of an implantable electrode assembly with a flexible body.

FIG. 40 illustrates generally an example 4000 of an implantable electrode assembly 4001 with a flexible body. That is, one or more portions of the electrode assembly 4001 can include a portion that can flex, bend, fold, turn, stretch, or otherwise conform to different positions. At least a body portion 4002 can thus be arranged or provided substantially parallel to a neural target 4015. In the example 4000, the implantable electrode assembly 4001 includes a distal electrode portion 4003, such as comprising one or more electrodes, that can be wrapped about the neural target 4015. In an example, the body portion 4002 of the implantable electrode assembly 4001 includes a can electrode or housing electrode configurable as an anode or cathode, and the distal electrode portion 4003 includes at least one electrode configurable as the other of an anode or cathode.

In an example, the electrode assembly 4001 includes a flexible joint in its body portion 4002 such that, after deployment of the distal electrode portion 4003 at or about the neural target 4015, at least a portion of the elongated body portion 4002 can be situated or provided substantially parallel to a longitudinal axis of the neural target. In the example of FIG. 40, the electrode portion 4003 includes two pairs of elongate members with respective conductive portions, and a first one of the pairs can be configured as an anode and a second one of the pairs can be configured as a cathode. In this example, the electrode assembly 4001 can be configured to deliver an electrostimulation therapy signal to the neural target 4015 when the pairs are coupled to the neural target 4015 and spaced apart along the neural target 4015 in an axial direction of the neural target 4015.

Figure 41:
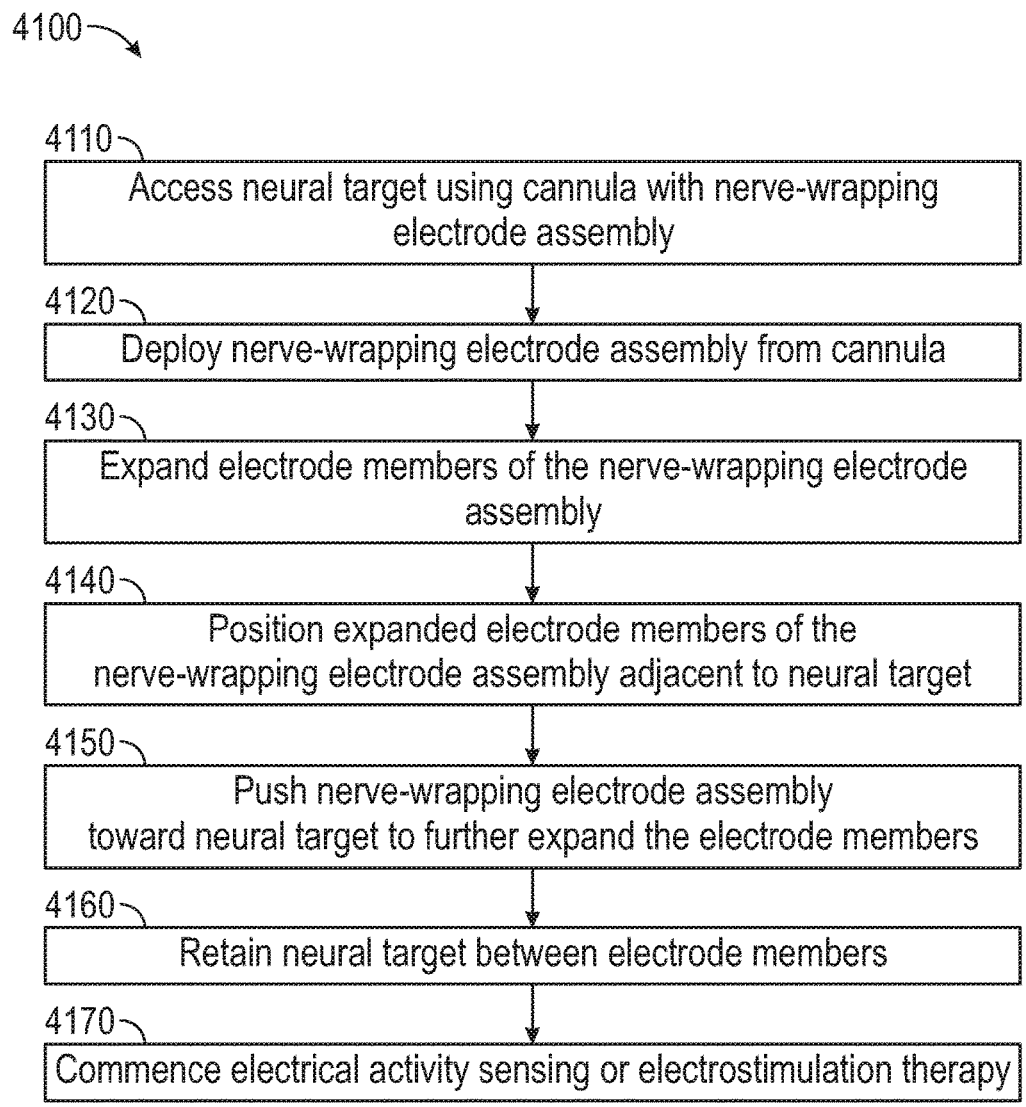
FIG. 41 illustrates generally an example of a method that includes accessing a neural target and providing an electrode about the neural target.

FIG. 41 illustrates generally an example of a method 4100 that includes accessing a neural target and providing an electrode about the neural target. At operation 4110, the example includes accessing a neural target inside of a patient body using a surgical apparatus, such as including using a cannula and a nerve-wrapping electrode assembly that can slide from a proximal end to a distal end of a lumen inside of the cannula. Operation 4110 can include using one or more of the electrode assemblies or embodiments as illustrated in the examples of FIGS. 30A-40.

At operation 4120, the nerve-wrapping electrode assembly can be deployed from the cannula. In an example, an electrode assembly can be deployed using a push rod to slide or force the nerve-wrapping electrode assembly outside of the cannula. For example, FIG. 30A illustrates generally an example that includes an implantable electrode assembly 3001 inside of a cannula 3010. FIGS. 30C and 30D illustrate the implantable electrode assembly 3001 partially and fully deployed from the cannula 3010, respectively. At operation 4130, the example includes expanding the electrode members of the of nerve-wrapping electrode assembly to an expanded second configuration. For example, as shown in FIG. 30E, when the electrode portion 3003 is deployed and unencumbered by the sidewalls of the cannula 3010, the electrode portion 3003 can include one or more members that can be extended or deployed away from one another, such as to provide a retention region for a neural target between the members.

At operation 4140, the example includes positioning a distal end of the electrode members of the nerve-wrapping electrode assembly adjacent to a neural target. In an example, the assembly can be provided substantially transverse to a longitudinal axis of the neural target (see, e.g., FIG. 31A). In an example, the assembly can be provided substantially parallel to a longitudinal axis of the neural target, such as for embodiments that require or use a twisting or turning motion to seat the neural target between different portions of one or more conductors.

At operation 4150, the example includes pushing the nerve-wrapping electrode assembly toward the neural target to thereby further expand the electrode members of the nerve-wrapping electrode assembly and receive the neural target between the electrode members. An illustration of operation 4150 can be found at FIG. 31B. At operation 4160, the method 4100 can include retaining the neural target between the electrode members (see, e.g., FIGS. 31C, 32C, and 38-40). At operation 4170, electrical activity sensing or electrostimulation therapy delivery can be performed using the electrode members.

D. Vascular Deployments

Solutions to the various problems discussed herein and associated with traditional electrodes and implant procedures can be addressed using miniature or injectable electrodes and electrode assemblies. In an example, such an electrode assembly can be leadless, and can be wirelessly coupled with one or more other devices using midfield wireless communication techniques, such as to transfer power or data. Midfield powering technology, including transmitters, transceivers, implantable devices, circuitry, and other details are discussed generally herein at FIGS. 1-5.

Various advantages come with midfield-powered devices. For example, a wirelessly-powered device does not require implantation of a relatively large, battery-powered pulse generator and the leads that are required to connect it electrically to the stimulation electrodes. This enables a simpler implant procedure at a lower cost and a much lower risk of chronic infection and other complications. A second advantage includes that the battery power source can be external to the patient and thus traditional design constraints (e.g., ultra-low power and ultra-high circuit efficiency requirements) can be less critical. Third, a midfield electrode device can be substantially smaller than traditional devices. Smaller devices can be better tolerated by and more comfortable to patients. In some examples, midfield devices can also be less costly to manufacture and implant or install inside of a patient.

In an example, a midfield device can be implanted or installed and configured to deliver electrostimulation to a renal nerve target. In an example, the midfield device can be implanted or installed at least partially in the vascular system of a patient. For example, the midfield device can be implanted or installed in an artery, vein, or other blood vessel. In an example, a midfield device can be implanted or installed in a jugular vein and configured to deliver electrostimulation to a vagal nerve target. Examples of various implantable device configurations are discussed below.

In an example, a midfield-based implantable device can be used to deliver electrostimulation therapy to renal targets. In recent years, there has been a significant amount of pre-clinical and clinical investigation into the denervation of the renal nerves to modulate blood pressure in the treatment hypertension. The size of the hypertension patient population is significant and there is a subset of that patient population that are refractory or non-responsive to conventional medical management including pharmaceuticals such as diuretics, ace inhibitors and other stronger pharmaceutical agents that are intended to lower blood pressure.

Although an acute procedure known as renal denervation showed promise in early clinical studies in reducing systolic and diastolic blood pressures in these refractory uncontrolled patients, the present inventors have recognized that a clinical need remains for a medical device that can treat patients with hypertension. In an example, an alternative to denervation can include providing electrostimulation to renal nerve targets, such as using neuromodulation techniques. In an example, such electrostimulation can be delivered through the large renal arteries with an implantable electrostimulator. Other, non-renal tissue areas can be similarly targeted.

The renal nerves are part of the sympathetic nervous system. In an example, neuromodulation (e.g., delivery of electrostimulation therapy) at the renal nerves can result in a similar effect that is achieved in the acute renal denervation procedure. In an example, such renal electrostimulation can be used in the treatment of uncontrolled hypertension. Other potential therapeutic benefits include the modulation of sympathetic-parasympathetic balance and modulation of the inflammatory response which is central in several serious diseases including heart failure and inflammatory bowel syndrome.

In an example, systems and methods according to the present disclosure can include or use a midfield-powered device that is implanted, installed, fixated, coupled, or otherwise disposed in a renal (or other) artery or other portion of a patient's vasculature. The device can be powered by an external powering unit that can be located at or near the kidney region where the stimulation device is implanted (see, e.g., discussion of FIGS. 1-5 regarding power transmission from an external unit to an implanted device).

In an example, a therapy signal delivered by the implanted midfield device can create an electrical field that emanates from the artery and travels through the artery wall to the renal nerve(s) (or other neural target) located nearby. In an example, the implanted midfield device can be implanted using tools that are substantially the same or similar to tools used in balloon catheter angioplasty, as discussed above. In an example, a proximal end of the device includes a fixation mechanism that is deployed at implant and is configured to minimally impede and not block blood flow through the artery. The fixation mechanism can have varied and different configurations, some of which are described herein.

Figure 42:
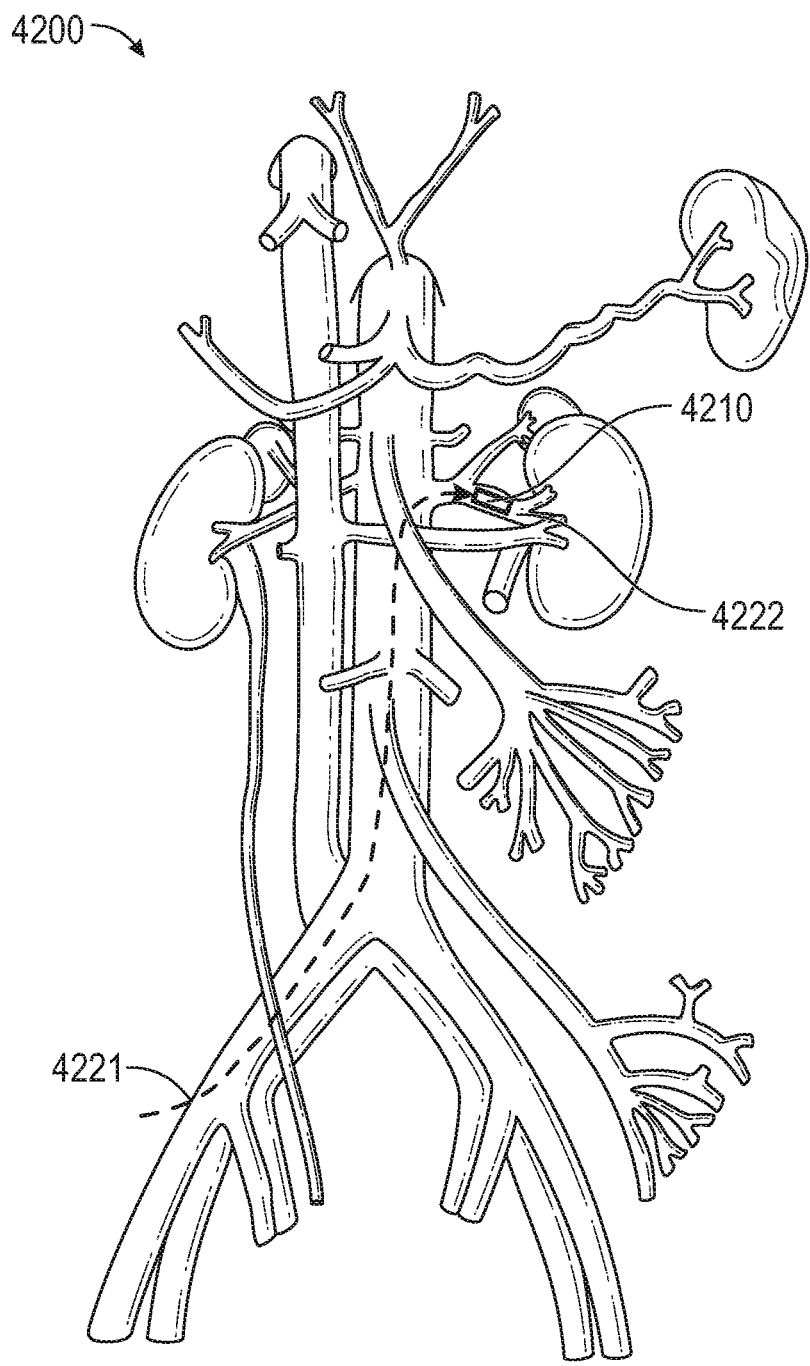
FIG. 42 illustrates generally an example of an implant location for a midfield device with respect to vasculature in the torso.

FIG. 42 illustrates generally an example 4200 of an implant location for a midfield device 4210 with respect to vasculature in the torso. In an example, an implant procedure can begin with an introduction of a delivery catheter or cannula through the Right Femoral Artery and to the Right External Iliac Artery 4221. The dashed line in FIG. 42 shows a path by which the midfield device 4210 can be introduced and located into position near or in the renal artery 4222. Other paths or destination locations can similarly be reached by the midfield device.

Figure 43:
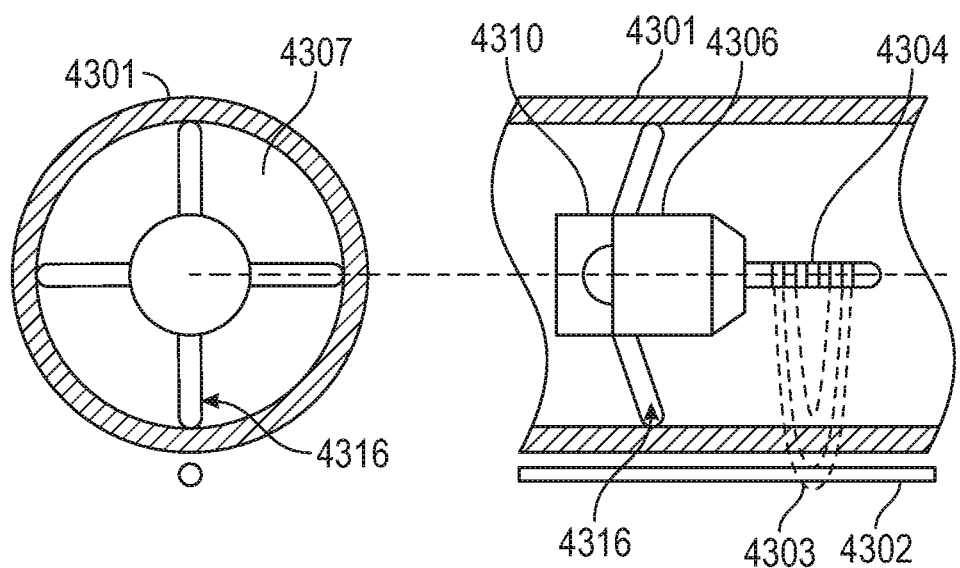
FIG. 43 illustrates generally an example that includes side and cross-section views of a midfield device configured for installation and fixation inside a blood vessel.

FIG. 43 illustrates generally an example that includes side and cross-section views of a midfield device 4310 configured for installation and fixation inside a blood vessel. Fixation of the device can be important to secure its chronic positioning for optimal nerve stimulation (e.g., at a renal target or elsewhere) and to allow substantially unrestricted blood flow through the vessel. In an example, the midfield device 4310 is 7 French (2.33 mm) or less at its largest diameter on the proximal end. Devices with other dimensions can similarly be used.

In an example, the implantable device does not block blood flow through the vessel when deployed because the vessel's inner diameter is larger than a cross-sectional area of the midfield device 4310 itself. The measured mean diameter of an artery can differ depending on the imaging method used. In an example, a representative diameter was found to be 5.04±0.74 mm using ultrasound, but 5.68+1.19 mm using angiography.

At right in the example of FIG. 43, the midfield device 4310 is deployed and affixed inside a first vessel having vessel wall 4301. The location of the midfield device 4310 can be near or adjacent to a renal nerve 4302 or other neural target. In an example, the midfield device 4310 includes a proximal housing assembly 4306 and a distal electrode assembly 4304. Drive circuitry (see, e.g., the stimulation driver 2814 in the example of FIG. 28), such as inside the proximal housing assembly 4306, can be used to provide electrical signals that drive the electrode assembly 4304 to provide an electrostimulation field 4303, and such field can be configured to influence or affect activity at the neural target.

In the example of FIG. 43, the midfield device 4310 includes various fixation features 4316. For example, the midfield device 4310 as shown can include multiple tines that extend away from the device's body portion, and the tines impinge on the inner surface of the vessel wall 4301 to locate and affix the device relative to the vessel, such as coaxially with the vessel. At least a portion of the midfield device 4310 is spaced apart from the vessel wall 4301 by the tines or fixation features 4316 such that one or more regions 4307 of unrestricted blood flow exist around the midfield device 4310. Although the example of FIG. 43 shows four discrete tines as the fixation features 4316, additional or fewer tines can be used as long as the number of tines is sufficient to affix the midfield device 4310 in a specified location relative to the vessel.

Figure 44:
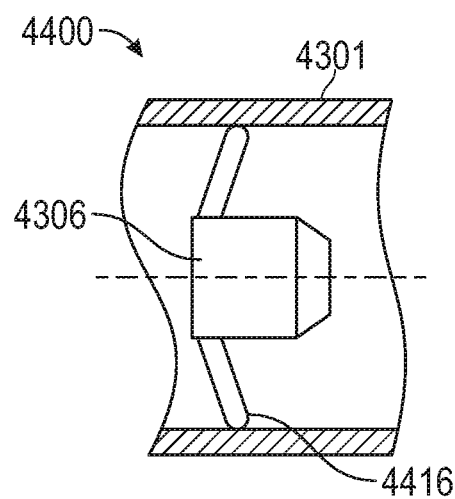
FIG. 44 illustrates generally a first example of a midfield device with multiple passive elements that project laterally away from the midfield device's housing assembly.

FIGS. 44-47 illustrate generally partial views of examples of different embodiments of the fixation features 4316 as applied to the midfield device 4310. FIG. 44 illustrates generally a first example 4400 of a midfield device with multiple passive elements 4416 that project laterally away from the midfield device's housing assembly 4306. The passive elements 4416 can comprise silicone or other non-reactive material, and can be configured to hold the implantable midfield device 4310 in position with respect to the vessel wall 4301. In an example, the passive elements 4416 provide a friction-fit with the vessel wall 4301 at a location where an inner diameter of the vessel becomes small enough, or tapers, to create an interference fit. In other words, an outer dimension of the passive elements 4416 can be about the same as the vessel inner cross-section dimension (e.g., at a location where the vessel tapers), while the body of the midfield device 4310 (e.g., comprising one or more electrodes) has a smaller outer dimension so as not to restrict blood flow around the device.

Figure 45:
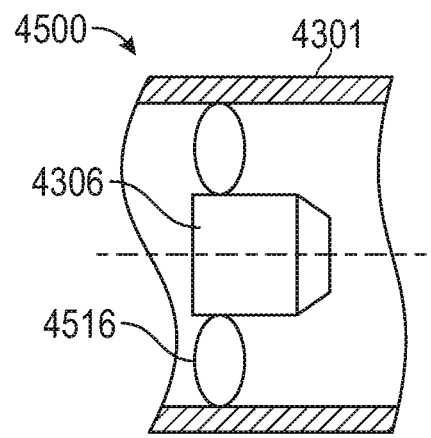
FIG. 45 illustrates generally a second example of a midfield device with multiple inflatable elements that project laterally away from the midfield device's housing assembly.

FIG. 45 illustrates generally a second example 4500 of a midfield device with multiple inflatable elements 4516 that project laterally away from the midfield device's housing assembly 4306. The inflatable elements 4516 can include one or more inflatable balloons (e.g., using gas or a liquid) that are configured to hold the implantable midfield device 4310 in position with respect to the vessel wall 4301, such as when inflated to an inner diameter of the vessel wall 4301 and thereby providing an interference fit. In an example, total occlusion of the vessel by, e.g., the inflatable elements 4516, can be acceptable under some circumstances. For example, occlusion of some small veins can be tolerated, or temporary occlusion can be permitted during placement procedures, such as for intraoperative testing.

Figure 46:
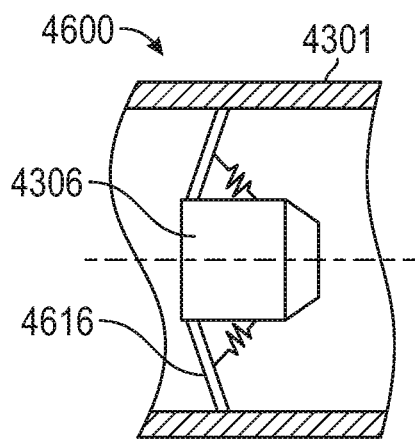
FIG. 46 illustrates generally a third example of a midfield device with multiple active elements that project laterally away from the midfield device's housing assembly.

FIG. 46 illustrates generally a third example 4600 of a midfield device with multiple active elements 4616 that project laterally away from the midfield device's housing assembly 4306. In an example, the active elements 4616 include one or more spring-loaded elements that can be deployed by the implanting clinician at the time of the implant procedure. In an example, the active elements 4616 can be retracted or constrained to a minimal diameter as the device is inserted or implanted. Once located in position, the clinician can deploy the active elements 4616 (e.g., using a mechanism on the cannula or push rod) and cause the active elements 4616 to expand to the inner diameter of the vessel wall 4301 thereby providing an interference fit and fixating the midfield device 4310 in a specified location.

Figure 47:
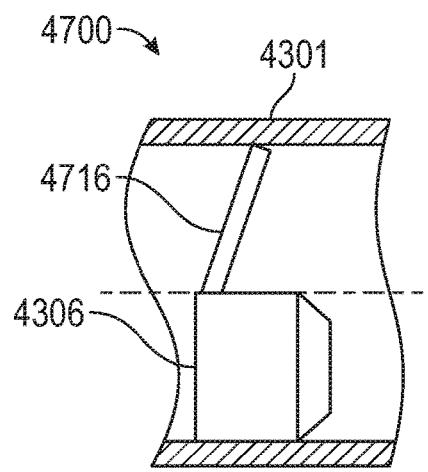
FIG. 47 illustrates generally a fourth example of a midfield device with a fixation element that projects laterally away from the midfield device's housing assembly.

FIG. 47 illustrates generally a fourth example 4700 of a midfield device with a fixation element 4716 that projects laterally away from the midfield device's housing assembly 4306. The fixation elements 4716 can be configured to hold the implantable midfield device 4310 in position against the vessel wall 4301. That is, while the examples of FIGS. 43-46 generally show fixation elements that are configured to locate the midfield device 4310 centrally or coaxially with respect to the vessel, the fourth example 4700 is configured to be offset from the center or axis of the vessel. That is, the fourth example 4700 includes a fixation element 4716 that biases the midfield device's housing assembly 4306 toward one side of the blood vessel. Similar to the other embodiments, however, the fourth example 4700 has a smaller outer dimension than the vessel wall 4301 so as not to restrict blood flow around the device.

Figure 48:
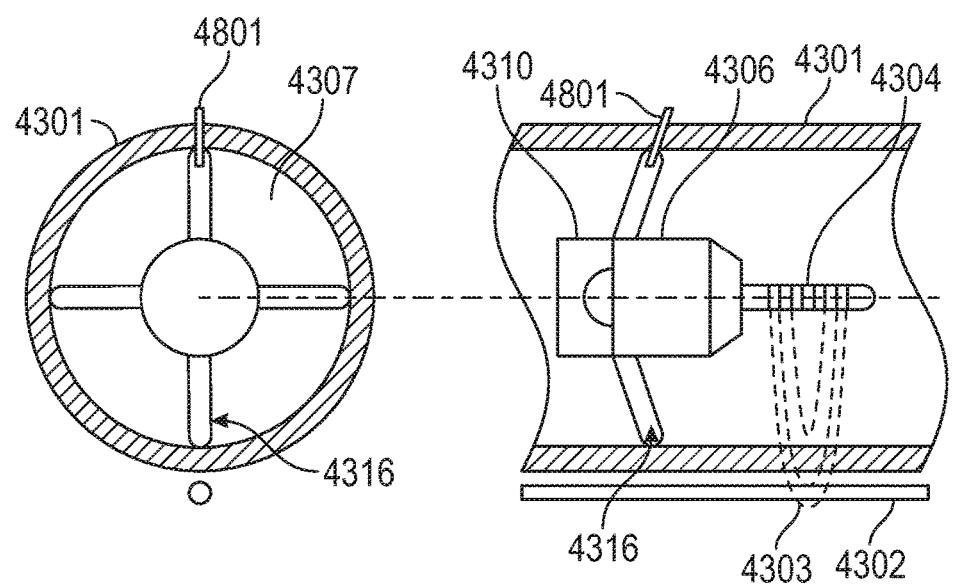
FIG. 48 illustrates generally a variation of the example midfield device from FIG. 43.

FIG. 48 illustrates generally a variation of the example device 4310 from FIG. 43. In the example 4800 of FIG. 48, at least one of the fixation features 4316 includes an electrode 4801 that is configured to penetrate the vessel wall 4301. That is, in an example, the electrode 4801 is integrated with one or more of the fixation features 4316. In another example, the electrode 4801 is a discrete electrode that is separate from the fixation features 4316. The electrode 4801 can be deployable after the device is located in position in the arterial system. In an example, the electrode 4801 includes a portion of an electrode array (e.g., a radially-extending array) provided along a portion of the midfield device 4310.

In an example, various other embodiments can include stent-based and/or spring-based systems for locating a midfield device inside a vessel. Such embodiments can have a low profile, can be constructed using biocompatible materials, and can be compatible with existing catheter-based tools and techniques.

Figure 49:
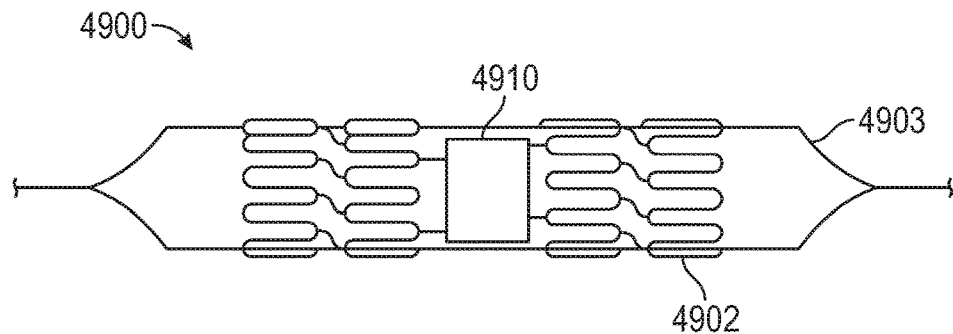
FIG. 49 illustrates generally an example of a stent-based system that can include a midfield device coupled to an expandable scaffold.

FIG. 49 illustrates generally an example of a stent-based system 4900 that can include a midfield device 4910 coupled to an expandable scaffold 4902. Although illustrated schematically in the figure by a rectangle, the midfield device 4910 can have any suitable size and shape for deployment inside a vessel. Generally, an outer hermetic housing of the midfield device 4910 has a minimal or low profile to minimize obstruction of fluid flow around or over the device, as described elsewhere herein.

The midfield device 4910 includes, or is coupled to, an antenna to receive midfield signals, such as from another implant or from a device provided externally to the patient. The midfield device 4910 can further include an energy storage element, and one or more sensors (e.g., to sense a physiologic characteristic from within the vasculature) or electrodes (e.g., to provide an electrostimulation therapy from within, or at least partially within, the vasculature).

The system 4900 can be configured for delivery to an intravascular location using a cannula. That is, the expandable scaffold 4902 and midfield device 4910 can be configured to be pushed through a lumen of a cannula toward a distal open end of the cannula for installation inside of a vessel. After exiting the lumen, the system 4900 can be expanded, using the expandable scaffold 4902, to thereby hold the midfield device 4910 inside of the vessel, and preferably toward one side wall of the vessel, to reduce obstruction of flow through the vessel. In an example, the delivery system includes or uses a balloon 4903 to expand the scaffold 4902 after deployment from the cannula.

In an example, the expandable scaffold 4902 comprises a spring material or spring construction. In this example, the scaffold 4902 is contracted or compressed inside of the delivery lumen of the cannula but the scaffold 4902 recoils or expands automatically, such as due to shape memory of the material, upon deployment from the lumen.

Figure 50:
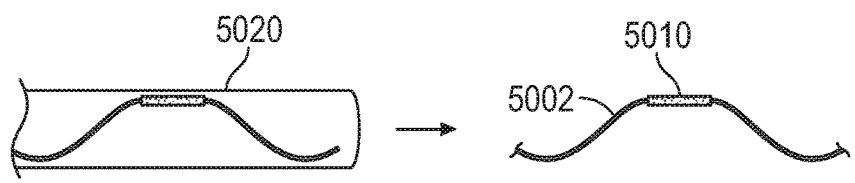
FIG. 50 illustrates generally an example of a stent-based or spring-based system that can include or use a midfield device.
Figure 51:
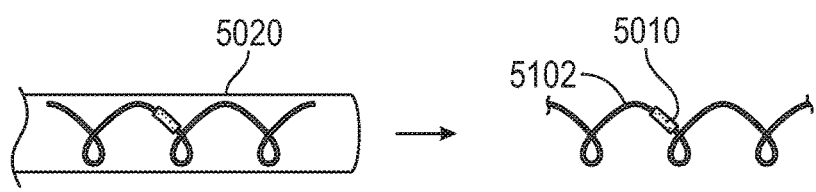
FIG. 51 illustrates generally an example of a spring-based support member coupled to a midfield device.
Figure 52:
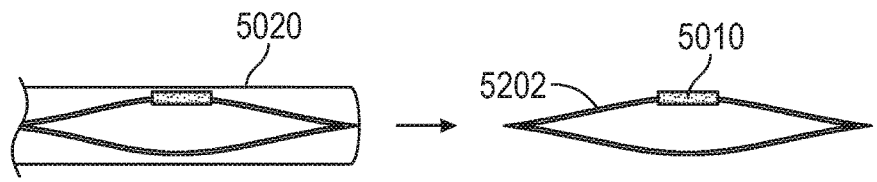
FIG. 52 illustrates generally an example of a spring-based support member coupled to a midfield device.

FIGS. 50-52 illustrate generally examples of stent-based or spring-based systems that can include or use a midfield device 5010. In the example of FIG. 50, the midfield device 5010 is coupled to a first spring support 5002. The first spring support 5002 can include at least one elongate member have a curved or wave-type shape. The midfield device 5010 can be coupled at various locations along the elongate member. In the example of FIG. 50, the midfield device 5010 is coupled at a substantially central location of the elongate member, such as near one of the member's maximum (or minimum) extents.

At left in FIG. 50, the first spring support 5002 is illustrated inside of a cannula 5020, and at right, FIG. 50 shows the first spring support 5002 deployed outside of the cannula 5020. The first spring support 5002 is compressed or contracted before deployment when it is inside of the cannula 5020. After deployment from a distal end of the cannula 5020 into a vessel, e.g., by a clinician using a push rod to slide the first spring support 5002 through the lumen of the cannula 5020, the first spring support 5002 can expand inside of the vessel and thereby force the midfield device 5010 toward or against a sidewall of the vessel. Placing the midfield device 5010 toward one sidewall of the vessel can help minimize restriction of blood flow through the vessel, and can help reduce blood flow turbulence around the device.

FIGS. 51 and 52 illustrate generally other examples of spring-based support members coupled to the same or different midfield device 5010. Like the example of FIG. 50, second and third spring-based supports 5102 and 5202 in FIGS. 51 and 52, respectively, can be compressed during a deployment procedure, such as when each member is disposed inside of the cannula 5020, and can be expanded after deployment from a delivery cannula.

In the example of FIG. 51, the second spring-based support 5102 includes at least one elongate member have a coil shape. The midfield device 5010 can be coupled at various locations along the elongate member. In the example of FIG. 51, the midfield device 5010 is coupled at a substantially central location of the elongate member.

In the example of FIG. 52, the third spring-based support 5202 includes a pair of wire members arranged to form an elongated, compressible oval-shaped assembly. The midfield device 5010 can be coupled at various locations along the assembly. In the example of FIG. 52, the midfield device 5010 is coupled at a substantially central location of the assembly such that the device is pushed toward one sidewall of the vessel when the third spring-based support 5202 expands inside of a vessel.

Figure 53:
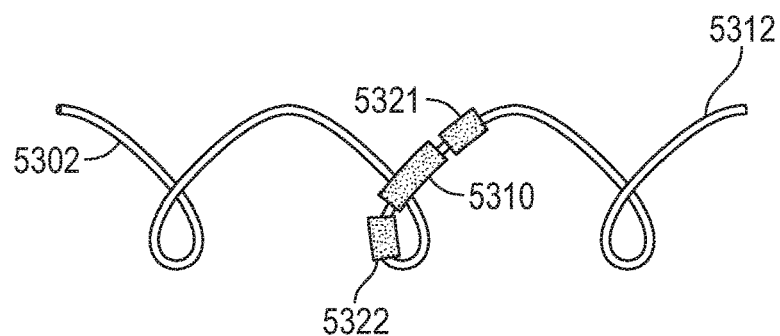
FIG. 53 illustrates generally an example of a spring-based support that includes an elongate member having a coil shape.

FIG. 53 illustrates generally an example of a fourth spring-based support 5302 that includes an elongate member having a coil shape. In the example of FIG. 53, a midfield device 5310 is coupled to the support 5302. In an example, the midfield device 5310 includes or is coupled to a portion of the support 5302 that comprises a portion of an antenna 5312 for the midfield device 5310. That is, the antenna 5312 for the midfield device 5310 can be integrated with the support 5302, or formed at least in part from the same material as the support 5302. In an example, the midfield device 5310 includes integrated electrodes or sensors, and in other examples, one or more electrodes or sensors is coupled to, and located remotely from, a main housing of the midfield device 5310. In the example of FIG. 53, the midfield device 5310 includes first and second electrodes 5321 and 5322 coupled to the support 5302 and spaced apart from the main housing of the midfield device 5310. The electrodes can be provided in fixed locations along the support 5302 or, in some examples, their positions can be adjusted by a clinician such as before or during implantation in a vessel.

In an example, a method of using the midfield device 5310 includes receiving energy at the midfield device 5310 using the antenna 5312. At least a portion of the received energy can be used in an electrostimulation therapy provided using the first and second electrodes 5321 and 5322. In an example, one or more physiologic sensors can be coupled to the midfield device 5310, and at least a portion of the received energy can be used to power the sensor(s) and/or to process information from the sensor(s) and/or to transmit information from the sensor(s) to a remote device, such as to another implant or to an external device.

In the examples of at least FIGS. 50-53, at least some portion of the respective support members can have a helical shape configured to encourage the support members to reside near or against a vessel wall when the device is deployed. Providing the support members against a vessel wall can help promote endothelialization and minimize blood flow obstruction.

Figure 54:
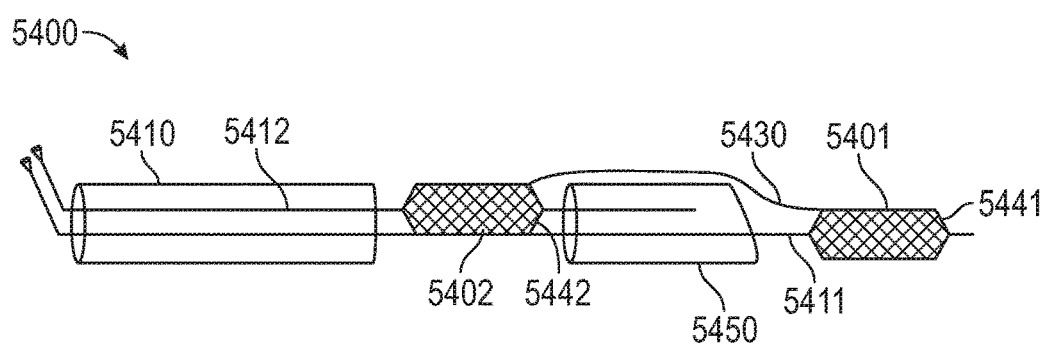
FIG. 54 illustrates generally an example of a system that can include multiple structures that are each configured for intravascular placement during a single implant procedure.

FIG. 54 illustrates generally an example of a system 5400 that can include multiple structures that are each configured for intravascular placement during a single implant procedure. The system 5400 includes a distal structure 5401 and a proximal structure 5402, and each of the distal and proximal structures 5401 and 5402 can be deployed using a common cannula 5410. In an example, the distal and proximal structures 5401 and 5402 are coupled to a common push rod. In the example of FIG. 54, the distal and proximal structures 5401 and 5402 are coupled to respective first and second push rods 5411 and 5412. In an example, each of the distal and proximal structures 5401 and 5402 includes a respective deployment device, such as a balloon.

In an example, the distal and proximal structures 5401 and 5402 are communicatively coupled, such as to provide a transmission channel for one or both of power and data between the structures. In the example of FIG. 54, the structures are coupled using a conductive lead 5430. In an example, the distal and proximal structures 5401 and 5402 are additionally or alternatively coupled using a wireless communication link.

In an example, at least one of the distal and proximal structures 5401 and 5402 includes or uses a midfield device that is coupled to a stent-based or spring-based support, such as described above in the examples of FIGS. 49-53. In an example, one of the distal and proximal structures 5401 and 5402 includes a midfield receiver, and the other of the structures includes at least one sensor or electrode configured to deliver an electrostimulation therapy.

In an example, the distal and proximal structures 5401 and 5402 are expandable outside of the cannula 5410. The distal structure 5401 can have a dedicated first balloon 5441 configured to inflate and expand the distal structure 5401 when the structure is deployed from the cannula 5410. The proximal structure 5402 can similarly have a corresponding dedicated second balloon 5442. In an example, the system 5400 includes a sleeve 5450 provided between the distal and proximal structures 5401 and 5402. The sleeve 5450 can be configured to buttress or support the vessel between the structures. In an example, one or more active or passive elements (e.g., sensors and/or electrodes) can be disposed on the sleeve 5450 and coupled to one or both of the distal and proximal structures 5401 and 5402.

In an example, the sleeve 5450 diameter is selected such that the assembly comprising the sleeve 5450 and distal structure 5401 advanced by the first push rod 5411 can be held firmly against the cannula 5410. In an example, as the cannula 5410 advances through vasculature (e.g., over a wire, such as is used for coronary artery stent placement), it also carries the sleeve 5450 and the distal structure 5410. The sleeve 5450 and distal structure 5410 can be deployed from the cannula 5410 using, e.g., the first push rod 5411 and the first balloon 5441. In an example, after the distal structure 5401 is deployed and the first balloon 5441 is deflated, the first push rod 5411 can be further advanced (e.g., up to several additional inches) to release the proximal structure 5402 from a sleeve of the main cannula 5410. Following this deployment, the first push rod 5411 can be withdrawn from the body entirely, and one or more sleeve portions of the main cannula 5410 can be withdrawn with it. Next, the proximal balloon 5442 can be expanded to deploy the proximal structure 5402. In another example, the first and second balloons 5441 and 5442 can be provided on a single catheter and push rod assembly, such as with separate lumens to independently inflate the balloons.

In examples that include a spring-based or stent-based support or member, the members can be configured to expand automatically after deployment from a cannula. In other examples, a balloon or other inflation or expansion device can be used together with the various members to expand them into a configuration that can chronically reside in a specified vessel location.

In an example, an implantable device is configured for deployment using a cannula lumen that extends through the vasculature. In some examples, the same or similar intraluminal delivery systems, such as used for vascular stent deployment, can be used to deploy an implantable neural stimulator as described herein.

Figure 55:
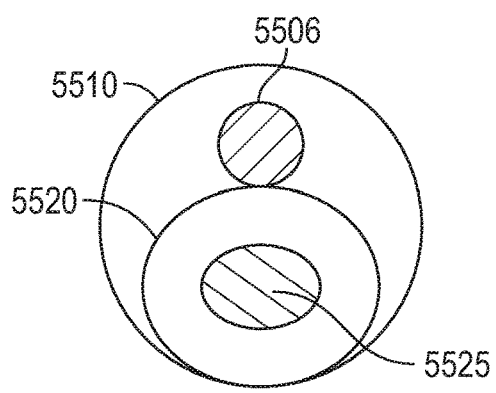
FIG. 55 illustrates generally a cross section view of a lumen that can enclose an implantable midfield device, a deployment structure, and an inflatable balloon.

FIG. 55 illustrates generally a cross section view of a lumen 5510 that can enclose an implantable device 5506 such as can include or use a midfield device, a deployment structure 5520, and an inflatable balloon 5525. The implantable device 5506 can be configured for intravascular deployment using the lumen 5510. In an example, the implantable device 5506 can be coupled to, or provided adjacent to, the deployment structure 5520 inside of the lumen 5510. The implantable device 5506 can be configured to ride on an outside portion of the deployment structure 5520 as it slides inside of the lumen 5510. In other examples, the implantable device 5506 can be configured to ride within the deployment structure 5520 (e.g., encircled or enclosed at least partially by the deployment structure 5520), such as displacing a portion of the balloon 5525.

Figure 56:
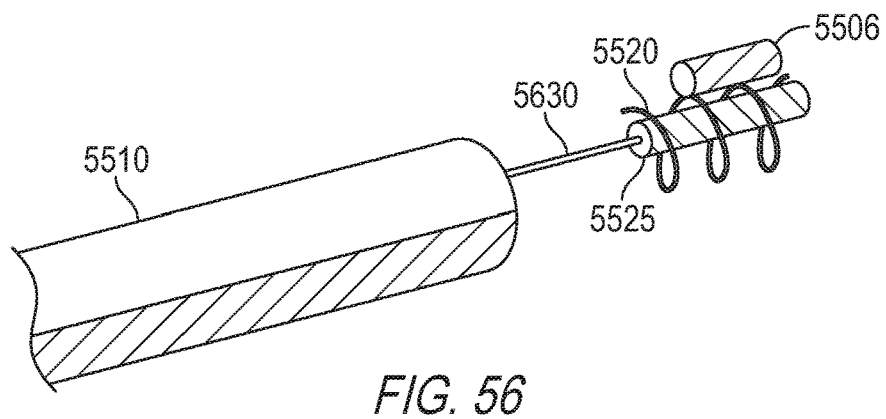
FIG. 56 illustrates generally a perspective view of an implantable device and deployment structure provided outside of a distal end of a lumen.

FIG. 56 illustrates generally a perspective view of the implantable device 5506 and deployment structure 5520 provided outside of a distal end of the lumen 5510. In an example, a push rod 5630 operable by a clinician can be used to adjust a location of the implantable device 5506 and deployment structure 5520 in the vasculature at implant. Although illustrated in FIG. 56 as having a coil or spring shape, the deployment structure 5520 can be any biocompatible structure configured to retain the implantable device 5506 in a substantially chronic position within a vessel.

Figure 57:
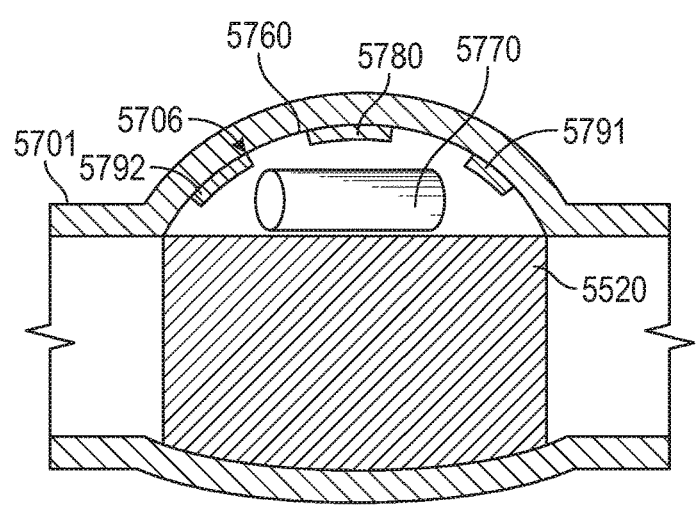
FIG. 57 illustrates generally an example of an implantable device installed in a vessel.

FIG. 57 illustrates generally an example of an implantable device 5706 installed in a vessel having a vessel wall 5701. The deployment structure 5520 is represented schematically and can have any suitable construction or configuration to encourage chronic placement of the implantable device 5706 against the vessel wall 5701.

In an example, the implantable device 5706 is a midfield device configured to receive and use energy received wirelessly using midfield signals. For example, the midfield device can include an antenna configured to receive energy from a propagating field inside of body tissue. The implantable device 5706 can include a device housing 5760, such as can include a hermetic or otherwise sealed housing structure, and various circuitry, or a hermetically sealed electronics module 5770, disposed inside of the device housing 5760. In an example, the electronics module 5770 includes one or more of a power storage circuit, a processor circuit, a memory circuit, or other circuit, as similarly described in the example first and second circuitry of FIGS. 27 and 28. In an example, the electronics module 5770 comprises a hermetic, cylindrical electronics housing to minimize its cross-sectional area. The cylindrical housing can be mounted or suspended in a biocompatible resin or epoxy with smoothed outer edges, such as to make the implantable package more streamlined and to reduce irritation to adjacent vessel walls. Other hermetic and non-cylindrical housing shapes can similarly be used.

In an example, the implantable device 5706 includes an antenna 5780 provided inside of the device housing 5760 but outside of the hermetically sealed electronics module 5770. In an example, the implantable device 5706 includes at least one and preferably at least two electrodes 5791 and 5792 provided at or near an outer-facing surface of the device housing 5760. That is, the electrodes 5791 and 5792 can be configured to face outward toward the vessel wall 5701 when the implantable device 5706 is installed using the deployment structure 5520. When properly installed, the electrodes 5791 and 5792 can contact the vessel wall 5701 to minimize signal transmission or shorting that can occur through the blood inside the vessel. Various features can be incorporated with the implantable device 5706 and/or electrodes 5791 and 5792 to help encourage the electrodes to maintain contact with the vessel walls. Some examples are shown in FIGS. 59 and 60 and are discussed below.

In the example of FIG. 57, the implantable device 5706 and deployment structure 5520 are configured to expand at least a portion of the vessel wall 5701, such as on one side of the vessel, and thus cause the vessel wall to distend or bulge slightly. By providing the implantable device 5706 in a bulged portion of the vessel, a central open area of the vessel can be provided to maintain blood flow therethrough.

Figure 58:
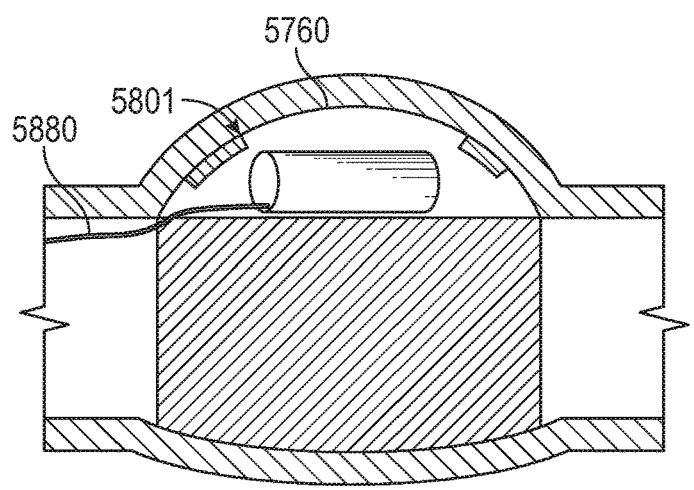
FIG. 58 illustrates generally an example of an implantable device that includes a device housing and an antenna that can extend outside of the housing.

FIG. 58 illustrates generally an example of a second implantable device 5801 configured similarly to the implantable device 5506 and/or 5706 but including an antenna 5880 that can extend outside of the device housing 5760. For example, the antenna 5880 can be a rigid or flexible structure that can reside inside the vessel after implant. Since the antenna 5880 is not constrained to being inside of, or contained within the device housing 5760, the antenna 5880 can be substantially longer or larger than the housing portion of the implant.

Figure 59:
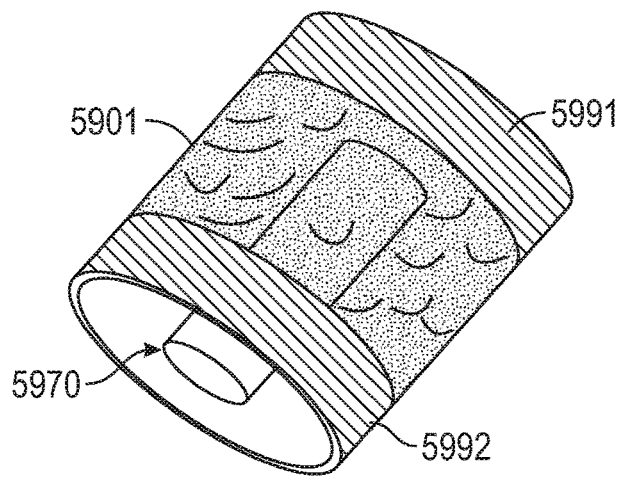
FIG. 59 illustrates generally a perspective view of an example of a first electrode assembly coupled to an electronics module for an intravascular implantable device.
Figure 60:
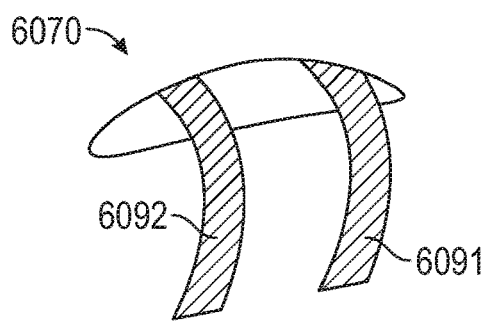
FIG. 60 illustrates generally a perspective view of an example of a second electrode assembly coupled to an electronics module for an intravascular implantable device.

FIG. 59 illustrates generally a perspective view of an example of a first electrode assembly coupled to a hermetically sealed electronics module 5970 for an intravascular implantable device. The electrode assembly is configured to encourage contact between a vessel wall and one or more electrodes. In an example, the electrode assembly includes a curved surface with one or more discrete conductive areas or electrodes. In an example, the curved surface can be selected to match a curvature of an interior vessel wall, or the surface can be flexible and can conform to a wall curvature. In examples with two or more electrodes, a non-conductive portion of the curved surface can be provided between the electrodes. In the example of FIG. 59, first and second electrodes 5991 and 5992 can be provided at opposite sides of a nonconductive membrane 5901 that separates the electrodes. The membrane 5901 can comprise various biocompatible materials and can be solid, barbed, or perforated. In an example, the membrane 5901 has a regular or irregular honeycomb configuration that helps the implant maintain chronic placement in a vessel and can, in some examples, integrate itself with the vessel wall. The membrane 5901 can help reduce or minimize current shunting between the first and second electrodes 5991 and 5992, such as by redirecting current through the adjacent vessel wall and toward a neural target.

FIG. 60 illustrates generally a perspective view of an example of a second electrode assembly coupled to a hermetically sealed electronics module 6070 for an intravascular implantable device. The electronics module 6070 is coupled to first and second electrodes 6091 and 6092 that have an arcuate shape and extend laterally relative to a body portion of the electronics module 6070. The example of FIG. 60 is similar to that of FIG. 59 but without the membrane 5901 between the electrodes 6091 and 6092.

Figure 61:
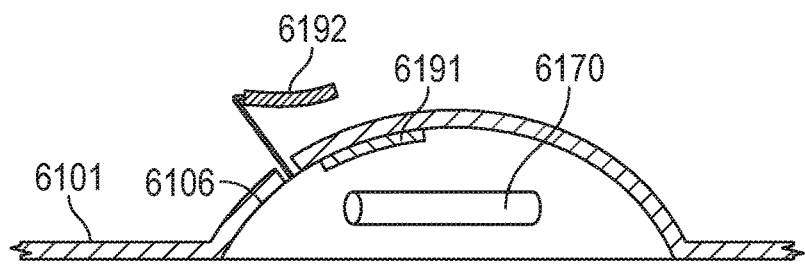
FIG. 61 illustrates generally an example of an intravascular implantable device.

FIG. 61 illustrates generally an example of an intravascular implantable device 6106. The example of FIG. 61 includes a hermetic device housing that encapsulates a hermetically sealed electronics module 6170. The implantable device 6106 can include a first electrode 6191 coupled to the electronics module 6170 and disposed on an outer-facing surface of the housing. In an example, the implantable device 6106 includes a second electrode 6192 provided on a deployment mechanism that can be configured to pierce a vessel wall. In an example, the second electrode 6192 is located outside of the vessel and therefore can be provided closer to a therapy target, and can thus be used to deliver a therapy (or sense a physiologic parameter) such as without adverse effects such as due to a vessel wall being between the electrode and the target.

Figure 62:
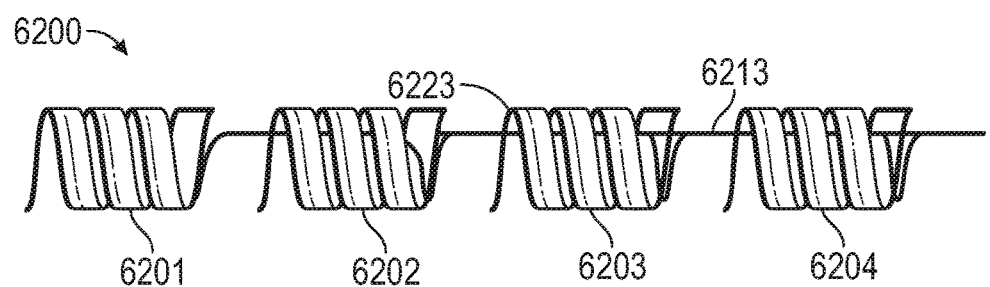
FIG. 62 illustrates generally a side view of an intravascular implantable device.

FIG. 62 illustrates generally a side view of an intravascular implantable device 6200. In an example, a midfield device can be implanted or installed and configured to deliver electrostimulation to a neural target using one or more portions of the device 6200. In an example, the device 6200 can be implanted or installed at least partially in the vascular system of a patient. For example, the device 6200 can be implanted or installed in an artery. The device 6200 can include one or more discrete electrode and/or support portions. In the example of FIG. 62, the device 6200 includes first, second, third, and fourth portions 6201, 6202, 6203, and 6204, respectively. Each of the first through fourth portions 6201-6204 can include or use an electrode and/or a support for a portion of a midfield device.

In the example of FIG. 62, the third portion 6203 includes a coiled support. The coiled support can include an elongated, substantially flat and optionally continuous material that is wound or coiled to a specified diameter. One or more portions of the coiled support can be conductive and can be coupled to a midfield device for use in physiologic parameter sensing or electrostimulation. That is, one or more portions of the coiled support can include or use an electrode. The coil diameter can be adjusted, such as at a time of implant or explant. The coil stiffness or material can be selected based on the particular application of the device 6200. For example, different materials can be used for renal applications and cardiac applications. The third portion 6203 can include a first electrode 6223 that can be coupled to or supported by the coiled support. The first electrode 6223 can be coupled to a midfield device and can be used for electrostimulation or physiologic parameter sensing together with drive or sense electronics included in the midfield device.

The example of FIG. 62 as illustrated includes four discrete portions; additional or fewer portions can be used, such as to provide a multi-polar electrostimulation or sensing device. A coupling wire 6213 can be used to couple adjacent ones of the portions of the implantable device 6200. In an example, the coupling wire 6213 is a series connection between adjacent portions of the device, and in other examples, different coupling wires can extend in parallel from each of the first through fourth portions 6201-6204 to another portion of a midfield device.

Figure 63:
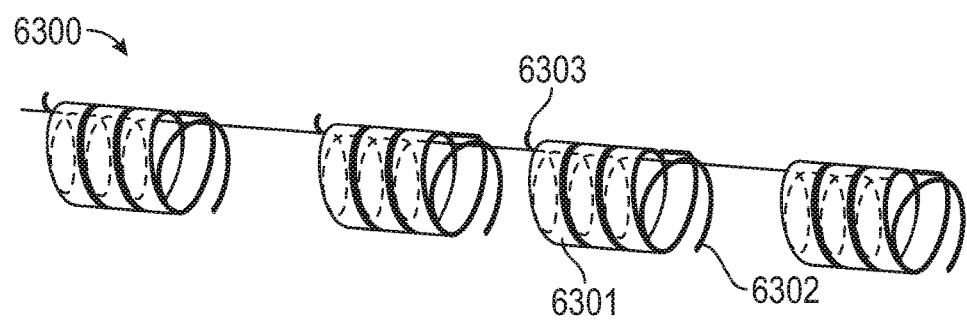
FIG. 63 illustrates generally a perspective view of a second intravascular implantable device.

FIG. 63 illustrates generally a perspective view of a second intravascular implantable device 6300. The second intravascular implantable device 6300 can include a coiled portion and one or more discrete support and/or electrode portions as similarly described above in the example of FIG. 62.

The second intravascular implantable device 6300 includes a first portion 6301 with a coiled support, and one or more portions of the support can be conductive and/or configured for use as an electrode. In an example, the first portion 6301 includes a discrete electrode extension 6302. The electrode extension 6302 can be curved to follow an inner wall shape of a vessel in which the device 6300 is installed. In an example, the first portion 6301 includes one or more tines, such as a first tine 6303. The first tine 6303 can extend orthogonally to a longitudinal axis of the coiled support. In an example, the first tine 6303 is configured to impinge on or pierce an interior vessel wall. The first tine 6303 can thus be used to anchor or fixate the implantable device 6300 at a particular specified location within a patient's vasculature. In an example, the first tine 6303 includes one or more conductive portions and can be used as an electrode when coupled to a midfield device.

Figure 64:
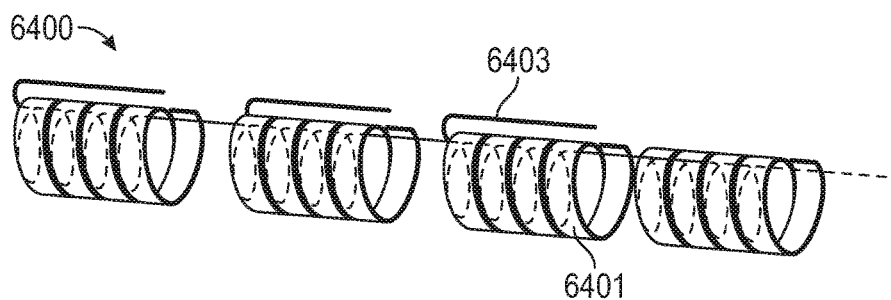
FIG. 64 illustrates generally a perspective view of a third intravascular implantable device.

FIG. 64 illustrates generally a perspective view of a third intravascular implantable device 6400. The third intravascular implantable device 6400 can include a coiled portion and one or more discrete support and/or electrode portions as similarly described above in the examples of FIGS. 62 and/or 63. In the example of FIG. 64, a first portion 6401 of the device 6400 includes an extension member 6403. In an example, the extension member 6403 extends substantially parallel to an axis of the third device's coiled support. The extension member 6403 can be configured to be deployed outside of a vessel wall, such as adjacent to the first portion 6401 of the device 6400. The extension member 6403 can help anchor or fixate the implantable device 6400 at a particular specified location within a patient's vasculature. In an example, the extension member 6403 includes one or more conductive portions and can be used as an electrode when coupled to a midfield device.

Figure 65:
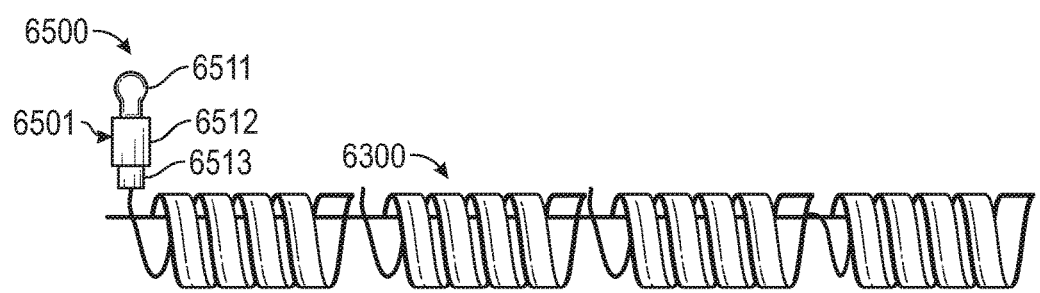
FIG. 65 illustrates generally an example of a midfield device coupled to an intravascular implantable device.

FIG. 65 illustrates generally an example 6500 of a midfield device 6501 coupled to the intravascular implantable device 6300. The midfield device 6501 can include an antenna 6511 configured to receive wireless midfield power and/or data signals, and a body portion 6512 that encloses telemetry, processing, and drive circuits, as similarly described elsewhere herein for implantable midfield devices.

The midfield device 6501 can further include an interconnect portion 6513 configured to be coupled to one or more electrodes deployed in a vessel. The midfield device 6501 can, in an example, receive a wireless power signal and, in response, use one or more electrodes on the implantable device 6300 to provide an electrostimulation therapy or to sense a physiologic parameter from a patient. In the example of FIG. 65, the midfield device 6501 is coupled to each portion of the implantable device 6300 using a serial connection. That is, a common conductor couples each electrode portion of the four illustrated portions of the device 6300 to the midfield device 6501. In other examples, a parallel connection can be used, such as to provide separate signals from the midfield device 6501 to the different discrete portions of the device 6300.

Figure 66:
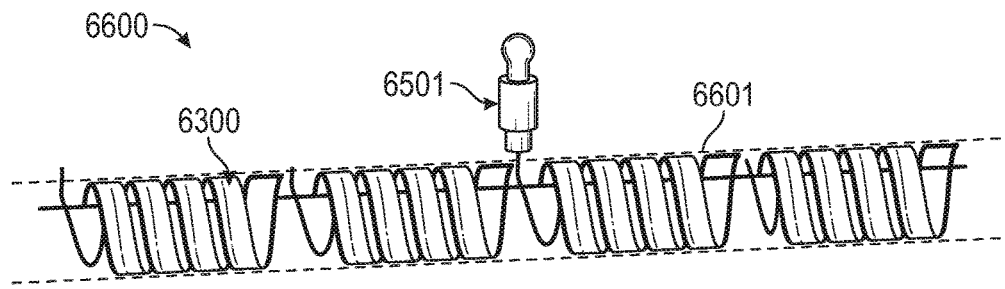
FIG. 66 illustrates generally an example of a midfield device coupled to the intravascular implantable device inside of a vessel.

FIG. 66 illustrates generally an example 6600 of the midfield device 6501 coupled to the intravascular implantable device 6300 inside of a vessel. The vessel walls 6601 are indicated by dashed lines. The coiled portions of the device 6300 abut or contact the vessel walls 6601. In the example of FIG. 66, tines from the device 6300 pierce the vessel walls 6601 at each of the different discrete coiled portions of the device 6300. As explained above, the tines can be used to fixate the device 6300 inside of the vessel, and/or the tines can include one or more conductive portions or electrodes for sensing a physiologic parameter or providing an electrostimulation to the patient. The various electrodes can be separately or commonly addressed by drive circuitry inside the midfield device 6501. In the example of FIG. 66, the midfield device 6501 is coupled to a central portion of the intravascular implantable device 6300, with conductors extending from the central portion of the device 6300 to the distal portions of the device 6300 to either side of the midfield device 6501.

Any one or more of the fixation features described herein can include a contingency (device, feature, mechanism, etc.) to pull backwards, to deflate, or to contract the device to a smaller diameter to allow for retrieval, explant (e.g., through the same vessel implant path), and/or adjustment of a placement of the various intravascular devices described herein.

Although the preceding discussion was generally directed to midfield-powered electrostimulation devices that are configured for renal nerve stimulation, the midfield-powered electrostimulation devices and features discussed herein can be deployed in other blood vessels or body locations. That is, the systems and methods discussed herein can be used to provide electrostimulation therapy to targets throughout the body, such as by locating chronically placed implantable devices in the vasculature at or near a particular target. In addition to renal system targets, other targets accessible from the vasculature can include a patient's phrenic nerves, splanchnic nerves, genital nerves, vagus nerve, or various receptors or targets in the gastrointestinal tract.

In an example, a midfield device can be deployed in a vessel that is in or near a patient's brain. Such a device can be configured to deliver electrostimulation to a neural brain target, or can be configured to sense brain activity. In an example, a midfield sensor device can record or archive measured neural activity information and report the information, in real-time or otherwise, to an external device, such as using midfield or other communication techniques.

II. Layered Midfield Transmitter Systems and Devices

In an example, a midfield transmitter device, such as corresponding to the external source 102 of the example of FIG. 1, can include a layered structure with multiple tuning elements. The midfield transmitter can be a dynamically configurable, active transceiver that is configured to provide RF signals to modulate an evanescent field at a tissue surface and thereby generate a propagating field within tissue, such as to transmit power and/or data signals to an implanted target device.

In an example, a midfield transmitter device includes a combination of transmitter and antenna features. The device can include a slot or patch antenna with a back plane or ground plane, and can include one or more microstrips or other device excitation features. In an example, the device includes one or more conductive plates that can be excited and thereby caused to generate a signal, such as in response to excitation of one or more corresponding microstrips.

Figure 67:
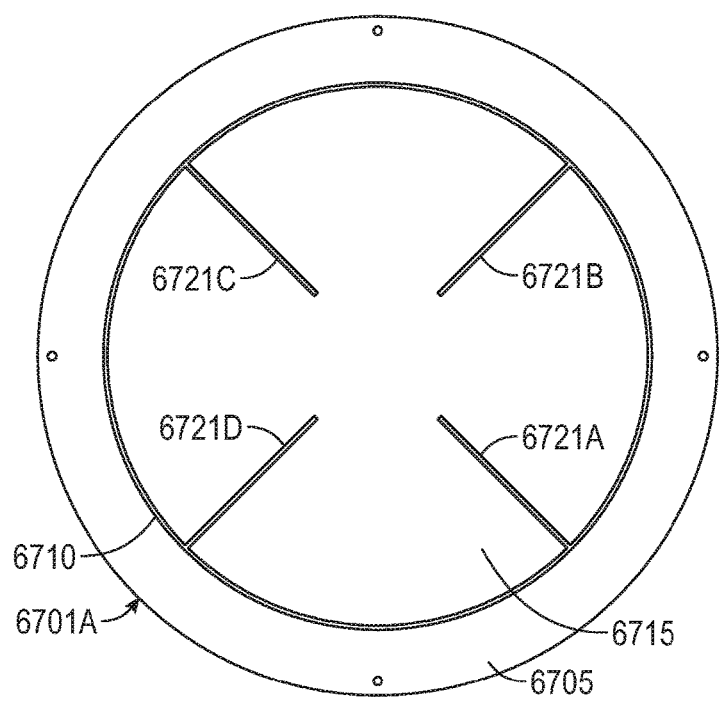
FIG. 67 illustrates generally a top view of an example of a first layer of a layered first transmitter.

FIG. 67 illustrates generally a top view of an example of a first layer 6701A of a layered first transmitter 6700. The first transmitter 6700 is illustrated as circular, however other shapes and profiles for the transmitter and various transmitter elements or layers can be similarly used. The first layer 6701A includes a conductive plate that can be etched or cut to provide various layer features. In the example of FIG. 67, the first layer 6701A includes a copper substrate that is etched with a circular slot 6710 to separate a conductive outer region 6705 from a conductive inner region 6715. In this example, the outer region 6705 includes a ring or annular feature that is separated by the circular slot 6710 from a disc-shaped feature comprising the inner region 6715. That is, the conductive inner region 6715 is electrically isolated from the conductive annulus comprising the outer region 6705. When the first transmitter 6700 is excited using one or more microstrip features, such as can be provided on a different device layer than is illustrated in FIG. 67, such as discussed below, the conductive inner region 6715 produces a tuned field, and the outer annulus or outer region 6705 can be coupled to a reference voltage or ground.

The example of FIG. 67 includes multiple tuning features with physical dimensions and locations with respect to the first layer 6701A to influence a field transmitted by the first transmitter 6700. In addition to the etched circular slot 6710, the example includes four radial slots, or arms 6721A, 6721B, 6721C, and 6721D, that extend from the circular slot 6710 toward the center of the first layer 6701A. Fewer or additional tuning features, such as having the same shape as illustrated or another shape, can similarly be used to influence a resonant frequency of the device. That is, although linear radial slots are shown, one or more differently shaped slots can similarly be used.

A diameter of the first layer 6701A and the slot 6710 dimensions can be adjusted to tune or select a resonant frequency of the device. In the example of FIG. 67, as the length of the arms 6721A-6721D increases, a resonance or center operating frequency decreases. Dielectric characteristics of one or more layers adjacent or near to the first layer 6701A can also be used to tune or influence a resonance or transmission characteristic. In the example of FIG. 67, the arms 6721A-6721D are substantially the same length. In an example, the arms can have different lengths. Orthogonal pairs of the arms can have substantially the same or different length characteristics. In an example, the first and third arms 6721A and 6721C have a first length characteristic, and the second and fourth arms 6721B and 6721D can have a different second length characteristic. Designers can adjust the arm lengths to tune a device resonance and current distribution pattern.

In an example, capacitive elements can be provided to bridge the slot 6710 in one or more places, such as to further tune an operating frequency of the transmitter. That is, respective plates of a capacitor can be electrically coupled to the outer region 6705 and the inner region 6715 to tune the device.

Dimensions of the first layer 6701A can vary. In an example, an optimal radius is determined by a desired operating frequency, characteristics of nearby or adjacent dielectric materials, and excitation signal characteristics. In an example, a nominal radius of the first layer 6701A is about 25 to 45 mm, and a nominal radius of the slot 6710 is about 20 to 40 mm. In an example, a transmitter device comprising the first layer 6701A can be made smaller at a cost of device efficiency, such as by decreasing the slot radius and/or increasing the length of the arms.

Figure 68A:
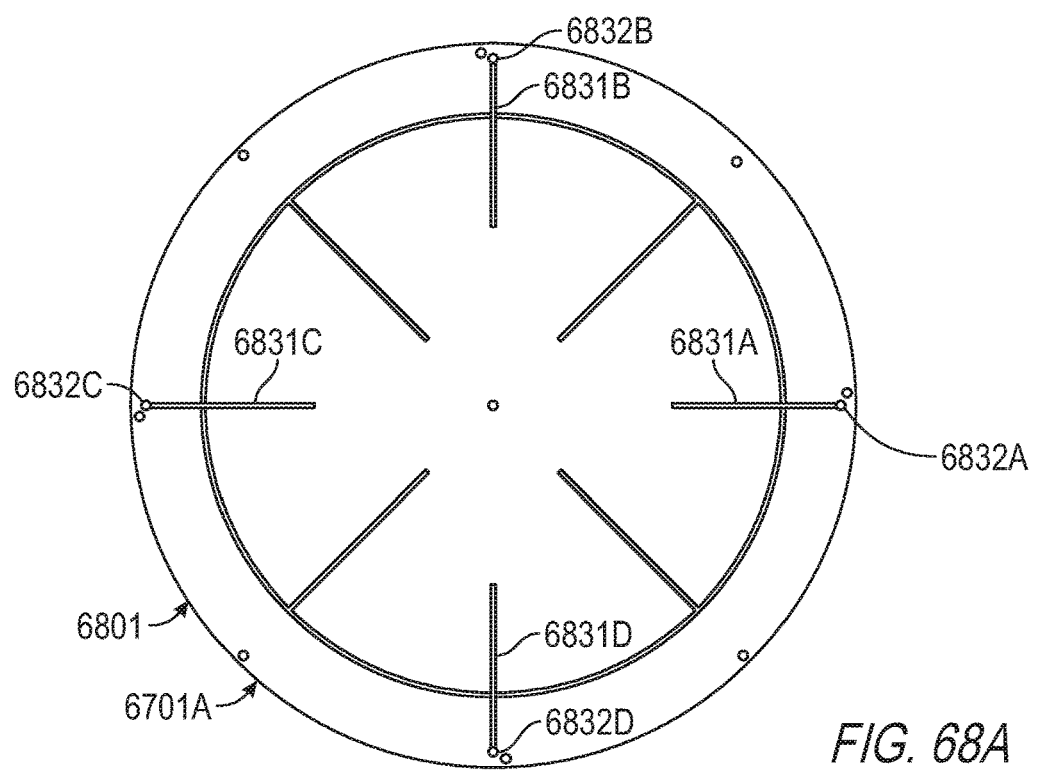
FIG. 68A illustrates generally a top view of a second layer superimposed over a first layer of a layered first transmitter.

FIG. 68A illustrates generally a top view of a second layer 6801 superimposed over the first layer 6701A of the layered first transmitter 6700. The second layer 6801 is spaced apart from the first layer 6701A, such as using a dielectric material interposed therebetween. In an example, the second layer 6801 includes multiple microstrips configured to excite the first transmitter 6700. The example of FIG. 68A includes first through fourth microstrips 6831A, 6831B, 6831C, and 6831D, corresponding respectively to the four regions of the conductive inner region 6715 of the first layer 6701A. In the example of FIG. 68A, the microstrips 6831A-6831D are oriented at about 45 degrees relative to respective ones of the arms 6721A-6721D. Different orientations or offset angles can be used. Although the example of FIG. 68A shows the microstrips 6831A-6831D spaced at equal intervals about the circular device, other non-equal spacings can be used. In an example, the device can include additional microstrips or as few as one microstrip.

The first through fourth microstrips 6831A-6831D provided on the second layer 6801 are electrically isolated from the first layer 6701A that includes the conductive annular outer region 6705 and the disc-shaped conductive inner region 6715. That is, a dielectric material can be interposed between the first and second layers 6701A and 6801 of the first transmitter 6700.

In the example of FIG. 68A, the first through fourth microstrips 6831A-6831D are coupled to respective first through fourth vias 6832A-6832D. The first through fourth vias 6832A-6832D can be electrically isolated from the first layer 6701A, however, in some examples the first through fourth vias 6832A-6832D can extend through the first layer 6701A.

In an example, one or more of the first through fourth microstrips 6831A-6831D can be electrically coupled to the conductive inner region 6715 of the first layer 6701A, such as using respective other vias that are not illustrated in the example of FIG. 68A. Such electrical connections are unnecessary to generate midfield signals using the device, however, may be useful for tuning performance of the device.

Various benefits are conferred by providing excitation microstrips, such as the first through fourth microstrips 6831A-6831D, on a layer that extends over the conductive inner region 6715 of the first layer 6701A. For example, an overall size of the first transmitter 6700 can be reduced. Various different dielectric materials can be used between the first and second layers 6701A and 6801 to reduce a size or thickness of the first transmitter 6700.

Figure 68B:
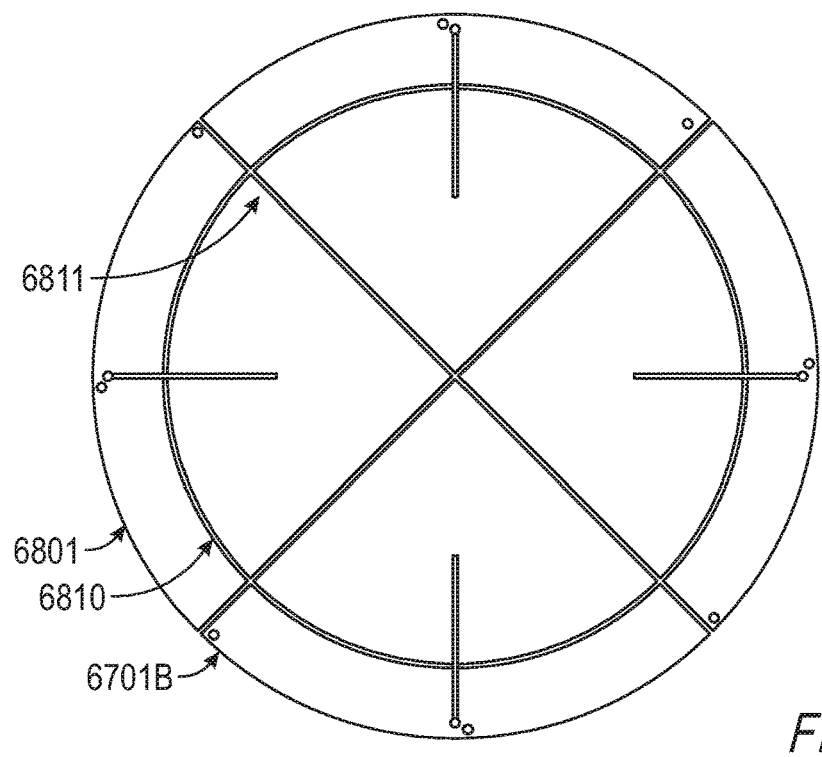
FIG. 68B illustrates generally a top view of a second layer superimposed over a different first layer of a layered transmitter.

FIG. 68B illustrates generally a top view of the second layer 6801 superimposed over a different first layer 6701B of a layered transmitter. Relative to FIG. 68A, the example of FIG. 68B includes the different first layer 6701B instead of the first layer 6701A that includes the arms 6721A-6721D. The different first layer 6701B includes a copper substrate that is etched with a circular slot 6810 to separate a conductive outer region from a conductive inner region. In addition to the etched circular slot 6810, the example includes a pair of linear slots 6811 arranged in an "X" and configured to cross at the central axis of the device. The example thus includes, on the different first layer 6701B, eight regions that are electrically decoupled, including four equally-sized sectors, or pie-piece shaped regions, and four equally-sized portions of an annulus.

In the example of FIG. 68B, the pair of linear slots 6811 extends to opposite side edges of the substrate or layer. When the device is excited (e.g., using the microstrips on the second layer 6801), the resulting current density across or over the different first layer 6701B is more concentrated at the outer annulus portions of the layer than at the inner sector portions of the layer. The device's operating frequency or resonance can be determined based on the area of the outer annulus, such as rather than being based on the length of the arms 6721A-6721D from the example of FIG. 68A. Total signal transfer efficiency from a transmitter using the embodiment of FIG. 68B to an implanted midfield receiver is similar to the efficiency from a transmitter using the embodiment of FIG. 68A, however, greater current density at the outer annulus portion of the embodiment of FIG. 68B can allow for greater steerability (that is, transmitted field steering) and thus potentially better access and transmission characteristics for communication with the implanted midfield receiver when the receiver is off-axis relative to the transmitter. Furthermore, the specific absorption rate (SAR) can be reduced when the embodiment of FIG. 68B is used, and unwanted coupling between ports can be reduced.

Figure 69:
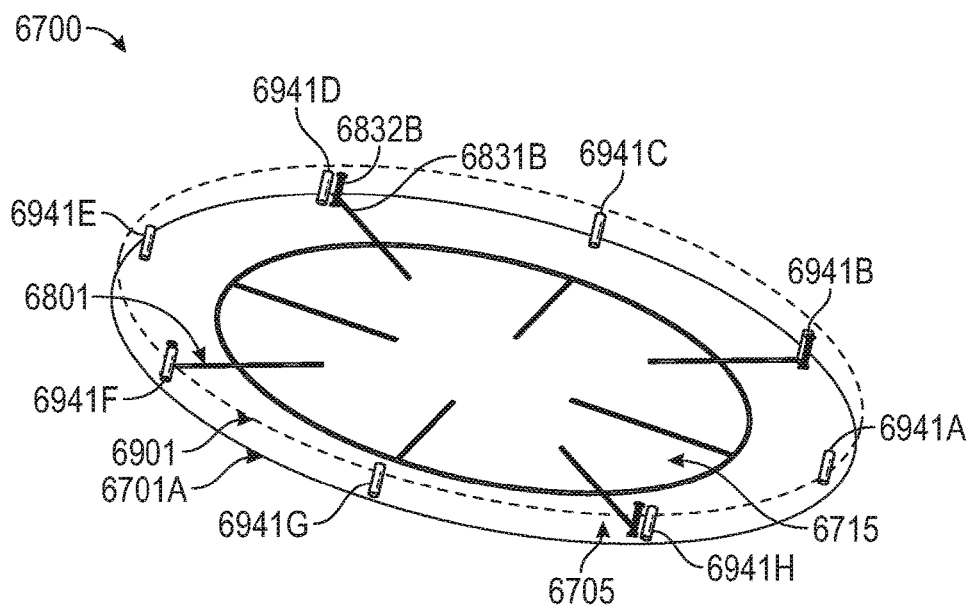
FIG. 69 illustrates generally a perspective view of an example of the layered first transmitter from FIGS. 67 and 68A.
Figure 70:
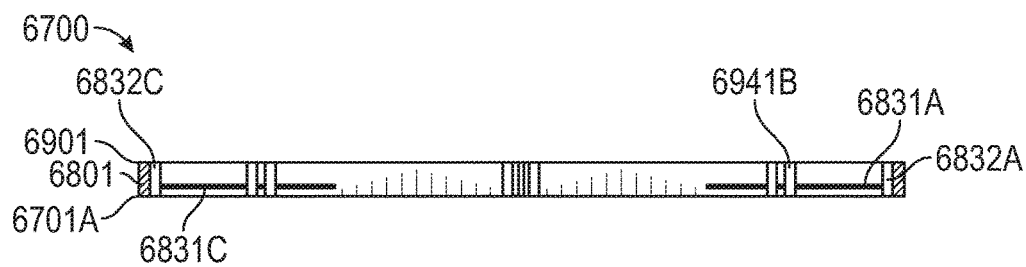
FIG. 70 illustrates generally a side, cross-section view of the layered first transmitter from FIGS. 67, 68A, and 69.

FIG. 69 illustrates generally a perspective view of an example of the layered first transmitter 6700. FIG. 70 illustrates generally a side, cross-section view of the layered first transmitter 6700. The examples include, at the bottom side of each of FIGS. 69 and 70, the first layer 6701A of the first transmitter 6700. At the top of the figures, the first transmitter 6700 includes a third layer 6901. The third layer 6901 can be a conductive layer that provides a shield or backplane for the first transmitter 6700. The second layer 6801, such as comprising one or more microstrips, can be interposed between the first and third layers 6701A and 6901. One or more dielectric layers (not illustrated) can be interposed between the first and second layers 6701A and 6801, and one or more other dielectric layers can be interposed between the second and third layers 6801 and 6901.

The examples of FIG. 69 and FIG. 70 include vias that electrically couple the outer region 6705 on the first layer 6701A with the third layer 6901. That is, ground vias 6941A-6941H can be provided to couple a ground plane (e.g., the third layer 6901) with one or more features or regions on the first layer 6701A. In the example, and as described above, each of the first through fourth microstrips 6831A-6831D is coupled to a respective signal excitation via 6832A-6832D. The signal excitation vias 6832A-6832D can be electrically isolated from the first and third layers 6701A and 6901.

In the examples of FIG. 69 and FIG. 70, the transmitting side of the illustrated device is downward. That is, when the first transmitter 6700 is used and positioned against or adjacent to a tissue surface, the tissue-facing side of the device is the downward direction in the figures as illustrated.

Providing the third layer 6901 as a ground plane confers various benefits. For example, other electronic devices or circuitry can be provided on top of the third layer 6901 and can be operated without unduly interfering with the transmitter. In an example, other radio circuitry (e.g., operating outside of the range of the midfield transmitter) can be provided over the third layer 6901, such as for radio communication with an implanted or other device (e.g., the implantable device 110, or other implantable device as described herein). In an example, a second transmitter can be provided, such as in a back-to-back relationship with the first transmitter 6700, and can be separated from the first transmitter 6700 using the ground plane of the third layer 6901.

Figure 71:
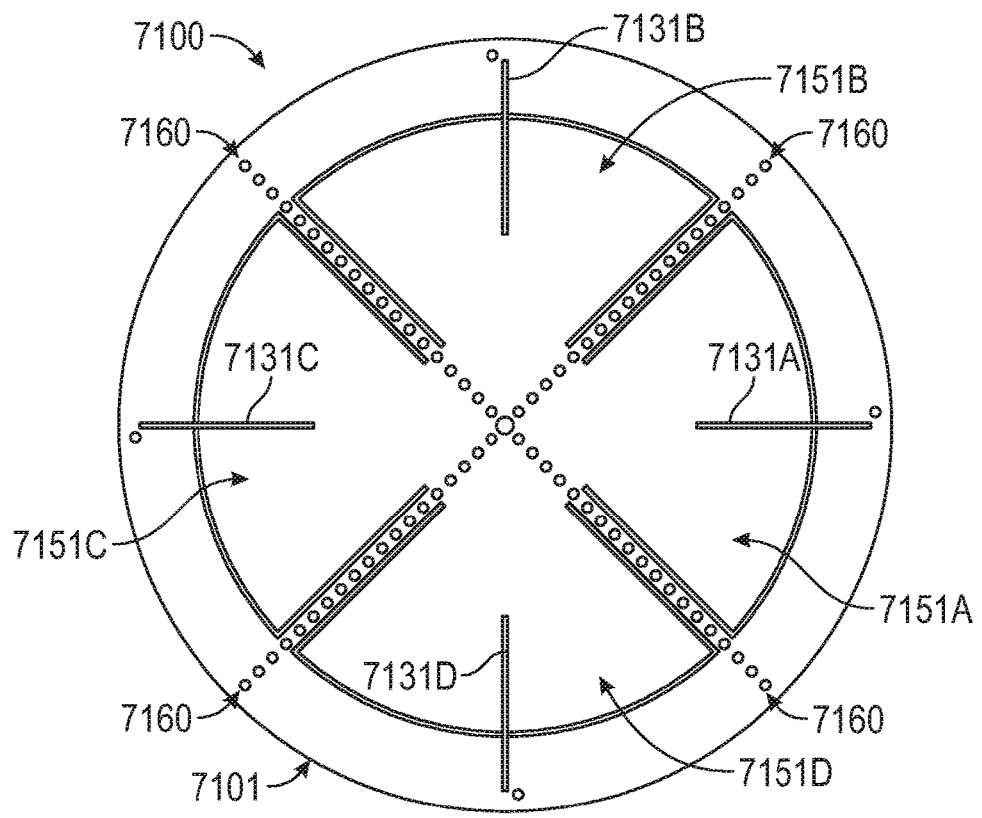
FIG. 71 illustrates generally a top view of an example of a layered second transmitter.
Figure 72:
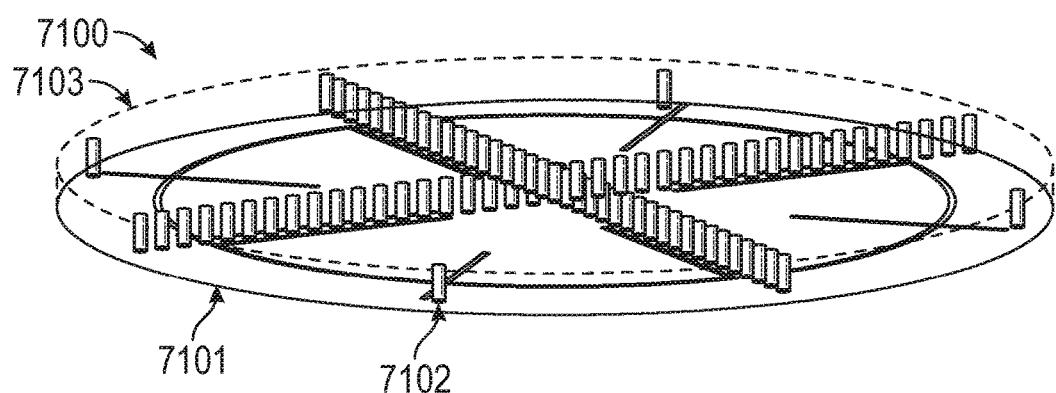
FIG. 72 illustrates generally a perspective view of the layered second transmitter from FIG. 71.

FIG. 71 illustrates generally a top view of an example of a layered second transmitter 7100. The second transmitter 7100 is similar to the first transmitter 6700 in profile and in its layered structure. The second transmitter 7100 includes microstrip excitation elements 7131A-7131D on a second layer that is offset from a first layer 7101 that includes first through fourth patch-like features 7151A-7151D. FIG. 72 illustrates generally a perspective view of the layered second transmitter 7100.

In the example of FIG. 71, the first layer 7101 includes a conductive plate that can be etched or cut to provide various layer features. The first layer 7101 includes a copper substrate that is etched to form several discrete regions. In the example of FIG. 71, the etchings partially separate the layer into quadrants. Unlike the examples of FIGS. 67-69, however, the etched portion does not create a physically isolated inner region. Instead, the example of FIG. 71 includes a pattern of vias 7160 that are used to partially electrically separate the discrete regions. The vias 7160 are coupled to another layer that serves as a ground plane. In the illustrated example, the vias 7160 are arranged in an "X" pattern corresponding to and defining the quadrants. In an example, the vias 7160 extend between the first layer 7101 and a second layer 7103, and the vias 7160 can be electrically isolated from another layer that comprises one or more microstrips. The arrangement of the vias 7160 divides the first layer 7101 into substantially separately-excitable quadrants.

The etched portions of the first layer 7101 include various linear slots, or arms, that extend from the outer portion of the first layer toward the center of the device. Similarly to the example of FIGS. 67-69, a diameter of the second transmitter device and the slot or arm dimensions can be adjusted to tune or select a resonant frequency of the device. Dielectric characteristics of one or more layers adjacent or near to the first layer 7101 can also be used to tune or influence a transmission characteristic of the second transmitter 7100.

In the example of FIG. 71, the vias 7160 and via walls provided in the "X" pattern can be used to isolate the different excitation regions, and can facilitate steering of propagating fields, such as to target an implantable device that is imprecisely aligned with the transmitter. Signal steering can be provided by adjusting various characteristics of the excitation signals that are respectively provided to the microstrips, such as the first through fourth microstrip excitation elements 7131A-7131D. For example, excitation signal amplitude and phase characteristics can be selected to achieve a particular transmission localization.

The present inventors have recognized that the vias, such as the vias 7160, provide other benefits. For example, the via walls can cause some signal reflections to and from the excitation, which in turn can provide more surface current and thereby increase an efficiency of signals transmitted to tissue.

Figure 73:
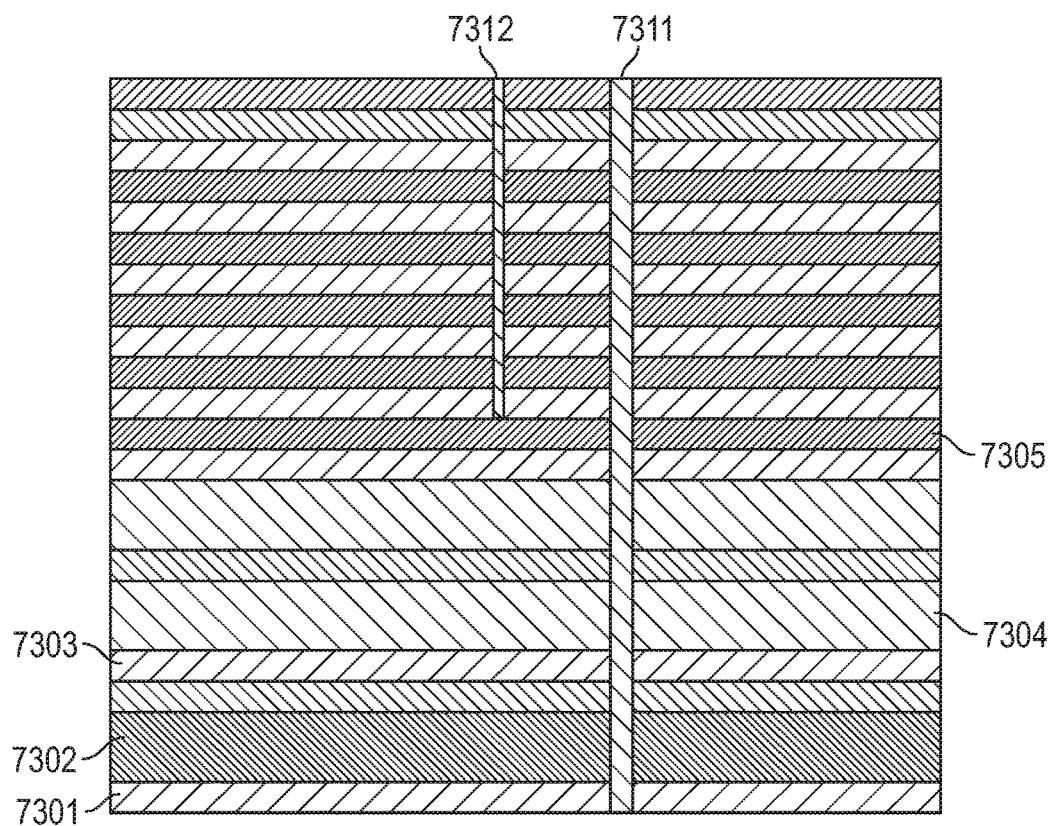
FIG. 73 illustrates generally an example of a cross-section schematic for a layered transmitter.

FIG. 73 illustrates generally an example of a cross-section schematic for a layered transmitter. The schematic can correspond generally to a portion of any one or more of the examples of FIGS. 67-72. In the example of FIG. 73, a bottom layer 7301 is a conductive first layer, such as copper, and can correspond to, e.g., the first layer 6701A of the example of FIG. 67. That is, the bottom layer 7301 in FIG. 73 can be the etched first layer 6701A in the example of FIG. 67.

Moving upward from the bottom layer 7301, FIG. 73 includes a first dielectric layer 7302. This first dielectric layer 7302 can include a low-loss dielectric material, preferably with Dk~3-13. Above the first dielectric layer 7302 can be a conductive second layer 7303. The conductive second layer 7303 can include the one or more microstrip excitation features discussed herein.

A second dielectric layer 7304 can be provided above the conductive second layer 7303. The first and second dielectric layers 7302 and 7304 can include the same or different material, and can have the same or different dielectric properties or characteristics. In an example, the first and second dielectric layers 7302 and 7304 can have different dielectric characteristics and such characteristics are selected to achieve a particular specified device resonance.

In the example of FIG. 73, the second dielectric layer 7304 includes multiple layers of dielectric material. As the second dielectric layer becomes thicker, a distance increases between the conductive second layer 7303 and a conductive third layer 7305. The conductive third layer 7305 can include backplane or ground. As the distance between the conductive second and third layers 7303 and 7305 increases, the bandwidth of the transmitter can correspondingly increase. The greater bandwidth can allow for greater data throughput, wider operating frequency range for frequency hopping, and can also improve manufacturability by increasing acceptable tolerances.

One or more vias can extend vertically through the layered assembly as illustrated in FIG. 73. For example, a first via 7311 can extend entirely through a vertical height of the device, while a second via 7312 can extend partially through the device. The vias can terminate at the various conductive layers, such as to provide electrical communication between the different layers and the drive circuitry or ground.

Various other layers can be provided above the conductive third layer 7305. For example, multiple layers of copper and/or dielectrics can be provided, such as can be used to integrate various electronic devices with the transmitter. Such devices can include one or more of a signal amplifier, sensor, transceiver, radio, or other device, or components of such devices, such as including resistors, capacitors, transistors, and the like.

Figure 74:
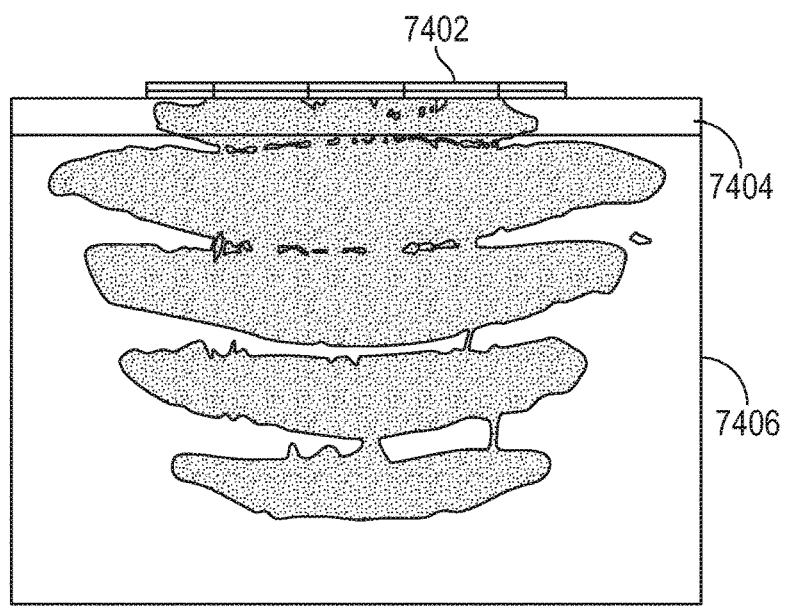
FIG. 74 illustrates generally an example that shows signal or field penetration within tissue.

FIG. 74 illustrates generally an example that shows signal or field penetration within tissue 7406. A transmitter, such as corresponding to one or more of the examples of FIGS. 67-73 or other transmitter such as the external source 102 of FIG. 1 and designated 7402 in this example, is provided at the top of the illustration. When the transmitter 7402 is activated to manipulate evanescent fields at an airgap 7404 between the transmitter 7402 and the tissue 7406, a propagating field (as illustrated by the progressive lobes in the figure) is produced that extends away from the transmitter 7402 and into the tissue 7406 toward the bottom of the illustration.

FIG. 75 illustrates generally an example that shows surface currents that result when a midfield transmitter, such as according to the examples of FIGS. 67-73, is excited. The surface current pattern closely mimics an oscillatory, optimal distribution to yield an evanescent field that will give rise to propagating fields inside of tissue (see, e.g., the example of a propagating field in FIG. 74).

In an example, the excitation signals (e.g., provided to the microstrips) that provide an optimal current pattern include oscillating signals provided to oppositely-oriented microstrips (e.g., second and fourth microstrips 6831B and 6831D in the example of FIG. 68A). In an example, the excitation signals further include signals provided to the orthogonal ports (e.g., first and third microstrips 6831A and 6831C in the example of FIG. 68A). This type or mode of excitation can be used to efficiently transfer signals to a deeply implanted receiver (e.g., a loop receiver) inside tissue. In an example, the loop receiver can be oriented in parallel with the current direction as illustrated at the center of the transmitter.

Figure 76:
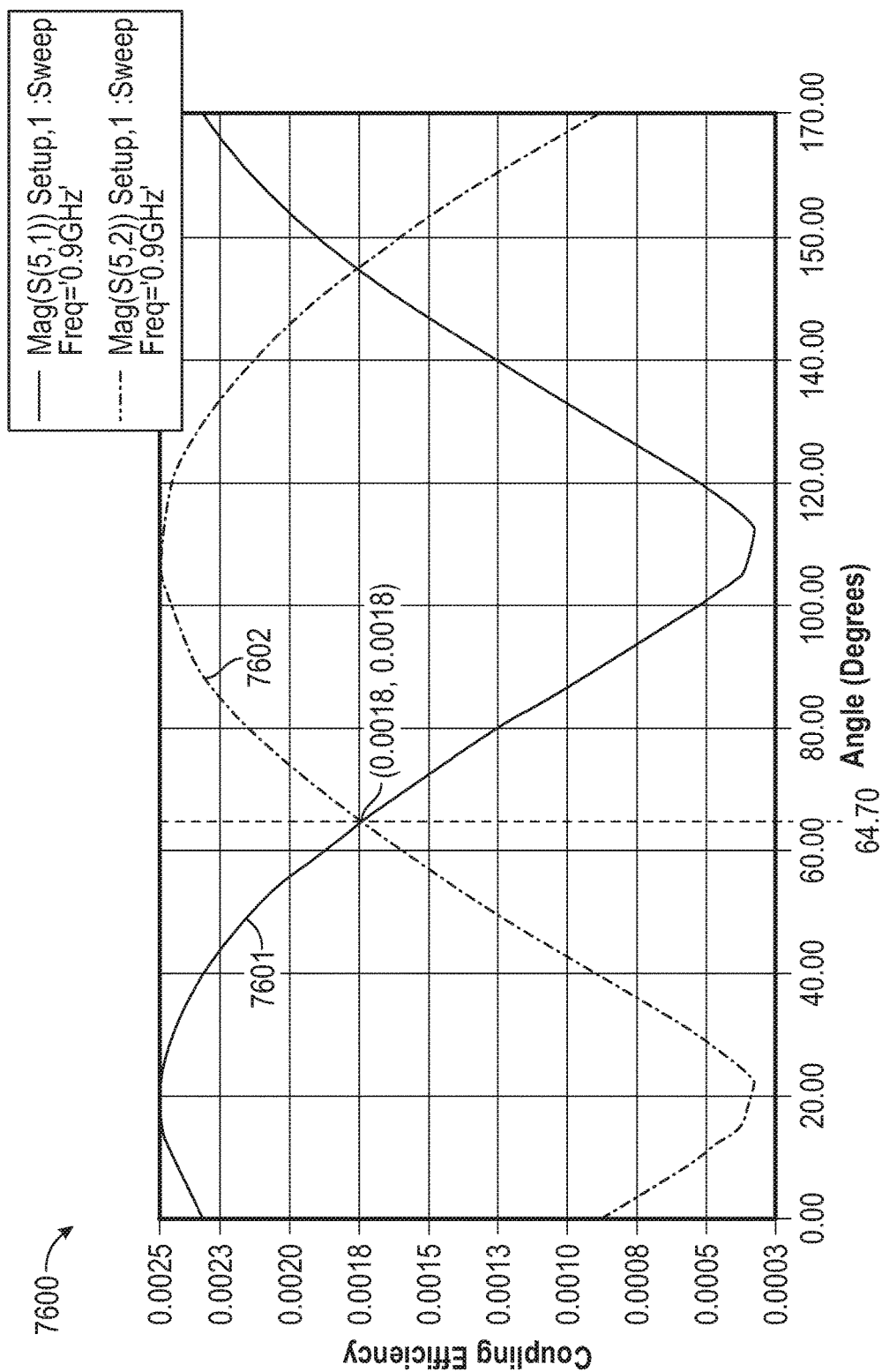
FIG. 76 illustrates generally an example of a chart that shows a relationship between coupling efficiency of transmitter ports to an implanted receiver with respect to a changing angle or rotation of the implanted receiver.

FIG. 76 illustrates generally an example of a chart 7600 that shows a relationship between coupling efficiency of the orthogonal transmitter ports to an implanted receiver with respect to a changing angle or rotation of the implanted receiver. The example illustrates that weighting the input or excitation signals provided to the orthogonal ports (e.g., to the microstrips) can be used to compensate for rotation of the implanted receiver. When the transmitter can compensate for such variations in target device location, consistent power can be delivered to the target device.

In the example of FIG. 76, a first curve 7601 shows an S-parameter, or voltage ratio of signal at the transmitter and the receiver, when a first pair of oppositely-oriented (e.g., top/bottom, or left/right) microstrips are excited by an oscillating signal. A second curve 7602 shows an S-parameter when a second pair of the oppositely-oriented microstrips are excited by an oscillating signal. The first and second pairs of microstrips are orthogonal pairs. The example illustrates that signals provided to the orthogonal pairs can be optimally weighted to achieve consistent powering with different implant angles, such as through constructive interference.

The example of FIG. 76 further illustrates that the transmitters discussed herein and their equivalents can be used to effectively steer or orient a propagating field such as without moving the transmitter or external source device itself. For example, rotational changes in the position of an implanted receiver can be compensated by weighting the signals provided to the various microstrips with different phases, such as to ensure a consistent signal is delivered to the implant. In an example, weighting can be adjusted based on a sensed or measured signal transfer efficiency, such as can be obtained using feedback from the implant itself. Adjusting the excitation signal weighting can change a direction of the transmitter current distribution, which in turn can change characteristics of the evanescent field outside of the body tissue.

Figure 77A:
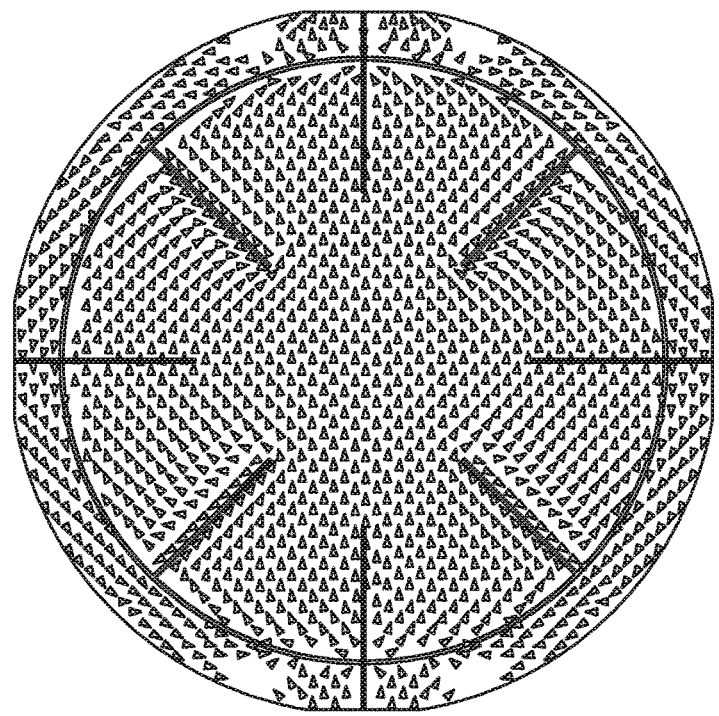
FIGS. 77A, 77B, and 77C illustrate generally examples of different polarizations of a midfield transmitter.
Figure 77B:
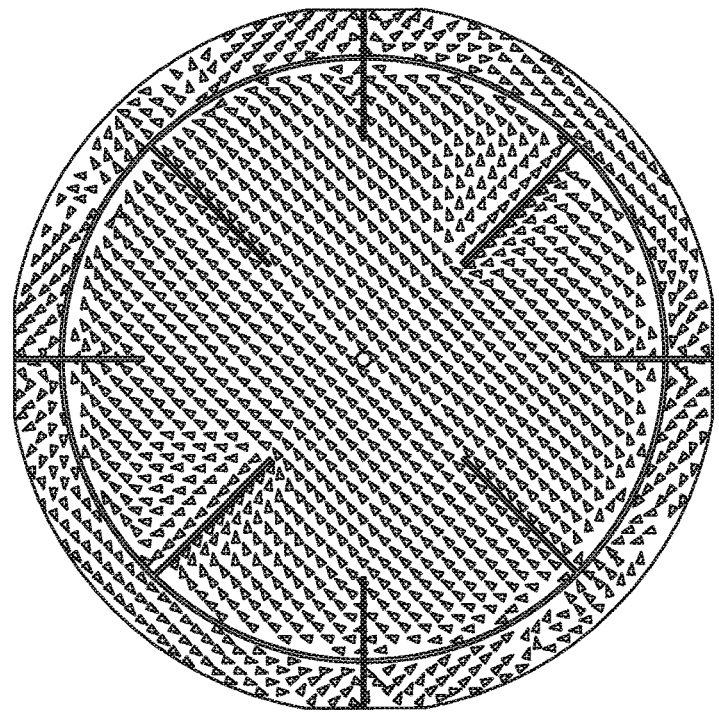
Figure 77C:
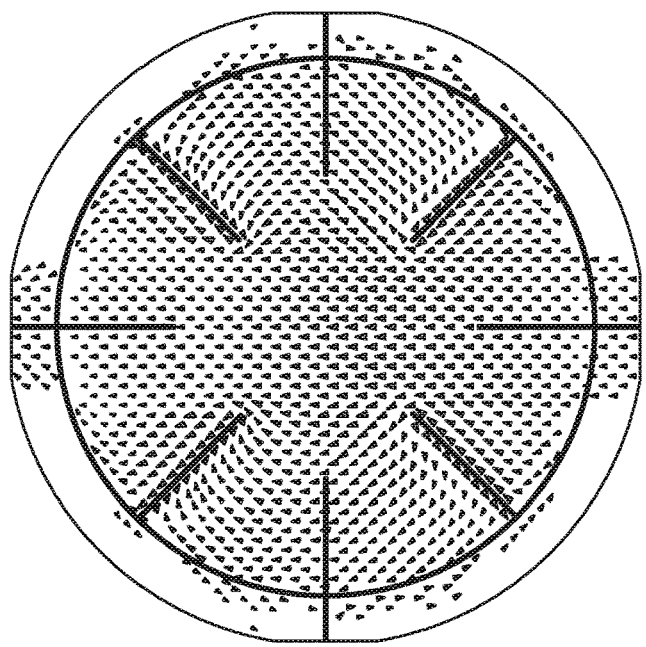

FIGS. 77A, 77B, and 77C illustrate generally examples of different polarizations of a midfield transmitter. In an example, a polarization direction of the transmitter can be changed by adjusting a phase and/or magnitude of an excitation signal provided to one or more of the microstrips or to other excitation features of a transmitter. Adjusting the excitation signals changes the current distribution over the conductive portions of the transmitter, and can be used to polarize the transmitter into or toward alignment with a receiver, such as to optimize a signal transfer efficiency. An optimal excitation signal configuration can be determined using closed loop feedback from the implanted device. For example, the external device can make a small change in signal phases and weighting of the transmissions. The implant can then use an integrated power meter to measure a strength of a received signal and communicate information about the strength to the external device, such as to determine an effect of the signal phase change. The system can converge over time using adjustments in both positive and negative directions for phase and port weighting between orthogonal ports.

The example of FIG. 77A illustrates a near-optimal current distribution in the left and right quadrants of the transmitter. In this example, the top and bottom microstrips receive a first pair of excitation signals and the orthogonal microstrips at the left and right can be unused.

The example of FIG. 77B illustrates a near-optimal current distribution that is rotated about 45 degrees relative to the example of FIG. 77A. In this example, all four of the microstrips can be excited by different excitation signals, such as with phase offsets.

The example of FIG. 77C illustrates a near-optimal current distribution that is rotated about 90 degrees relative to the example of FIG. 77A. In this example, the left and right microstrips receive a second pair of excitation signals and the orthogonal microstrips at the top and bottom are unused.

Figure 78:
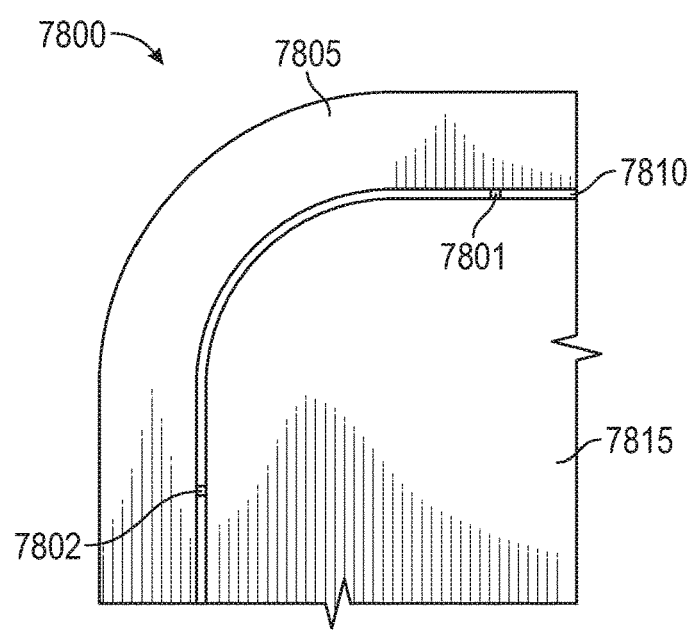
FIG. 78 illustrates generally an example of a portion of a layered midfield transmitter showing a first layer with a slot.

FIG. 78 illustrates generally an example of a portion of a layered midfield transmitter 7800 showing a first layer with a slot 7810. In an example, the slot separates an outer conductive region 7805 from an inner conductive region 7815 of the first layer. Additionally or alternatively to adding arms or radial slots to tune an operating frequency of the transmitter 7800, capacitive elements can be coupled across opposing conductive sides of the slot 7810, such as to bridge the outer and inner conductive regions 7805 and 7815. In the example of FIG. 78, first and second capacitive elements 7801 and 7802 bridge the outer and inner conductive regions 7805 and 7815 at different locations along the slot 7810. The capacitive elements for such bridging and tuning can generally be in the picofarad range. Other transmitter configurations and geometries can similarly be used to achieve the same current distribution and steerable fields.

Figure 79:
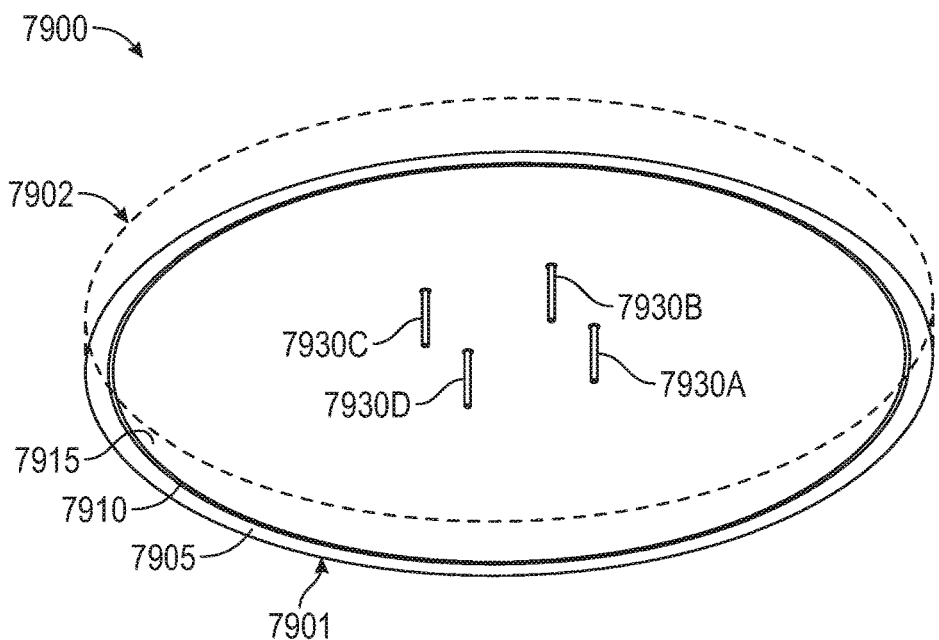
FIG. 79 illustrates generally a perspective view of an example of a layered third transmitter.

FIG. 79 illustrates generally a perspective view of an example of a layered third transmitter 7900. The examples includes, at the bottom side of the illustration, a first layer 7901 of the third transmitter 7900. At the top of the figure, the third transmitter 7900 includes a second layer 7902. The first and second layers 7901 and 7902 can be separated using a dielectric layer. Similar to the example of FIG. 67, the first layer 7901 can include a slot 7910 that separates, or electrically isolates, an outer region 7905 of the first layer 7901 from an inner region 7915 of the first layer 7901. The slot 7910 separates the annular outer region 7905 (e.g., an outer annular region) from a disc-shaped inner region 7915 (e.g., an inner disc region). In an example, the second layer 7902 can be a conductive layer that provides a shield or backplane for the third transmitter 7900.

The example of FIG. 79 includes vias 7930A-7930D that electrically couple the inner region 7915 on the first layer 7901 with drive circuitry, such as can be disposed on the second layer 7902. Ground vias (not shown) can be used to electrically couple the outer region 7905 with the second layer 7902. That is, the example of FIG. 79 can include a transmitter with an inner region 7915 of the first layer 7901 that is excitable without the use of additional layers and microstrips. In an example, the first layer 7901 can be tuned or modified, such as by adding one or more arms that extend from the slot 7910 toward a center of the device. However, the circular slot 7910 can generally be made large enough that a suitable operating resonance or frequency can be achieved without using such additional etched or deposited features as a slot.

Figure 80:
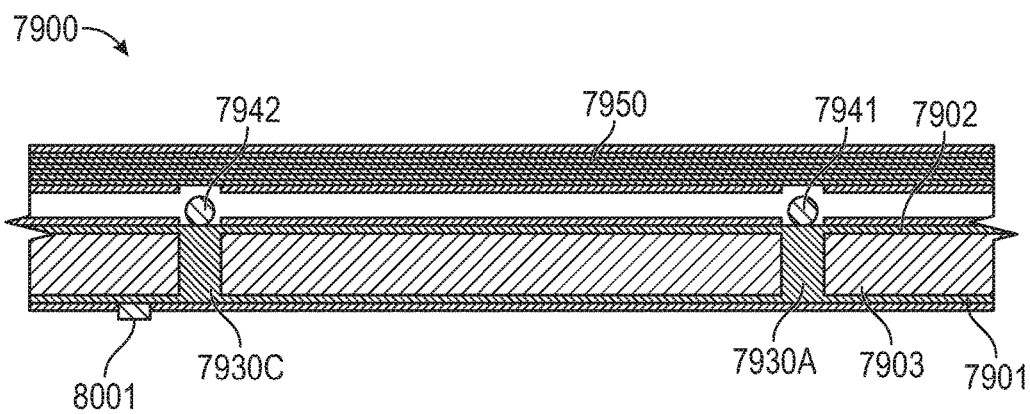
FIG. 80 illustrates generally a side, cross-section view of the layered third transmitter from FIG. 79.

FIG. 80 illustrates generally a side, cross-section view of the layered third transmitter 7900. The example of FIG. 80 illustrates generally that a dielectric layer 7903 can be provided between the first and second layers 7901 and 7902 of the third transmitter 7900. In an example, a circuit assembly 7950 can be provided adjacent to the third transmitter 7900, and can be coupled with the third transmitter 7900 such as using solder bumps 7941, 7942. Using solder bumps can be convenient to facilitate assembly by using established solder reflow processes. Other electrical connections can similarly be used. For example, the top and bottom layers can include an edge plating and/or pads to facilitate interconnection of the layers. In such an example, the top layer can optionally be smaller than the bottom layer (e.g., the top layer can have a smaller diameter than the bottom layer) and optical verification of the assembly can be performed more easily. In an example, the third transmitter 7900 can include one or more capacitive tuning elements 8001 coupled with the first layer 7901, such as at or adjacent to the slot 7910.

III. Embodiments of Related Computer Hardware and/or Architecture

Figure 81:
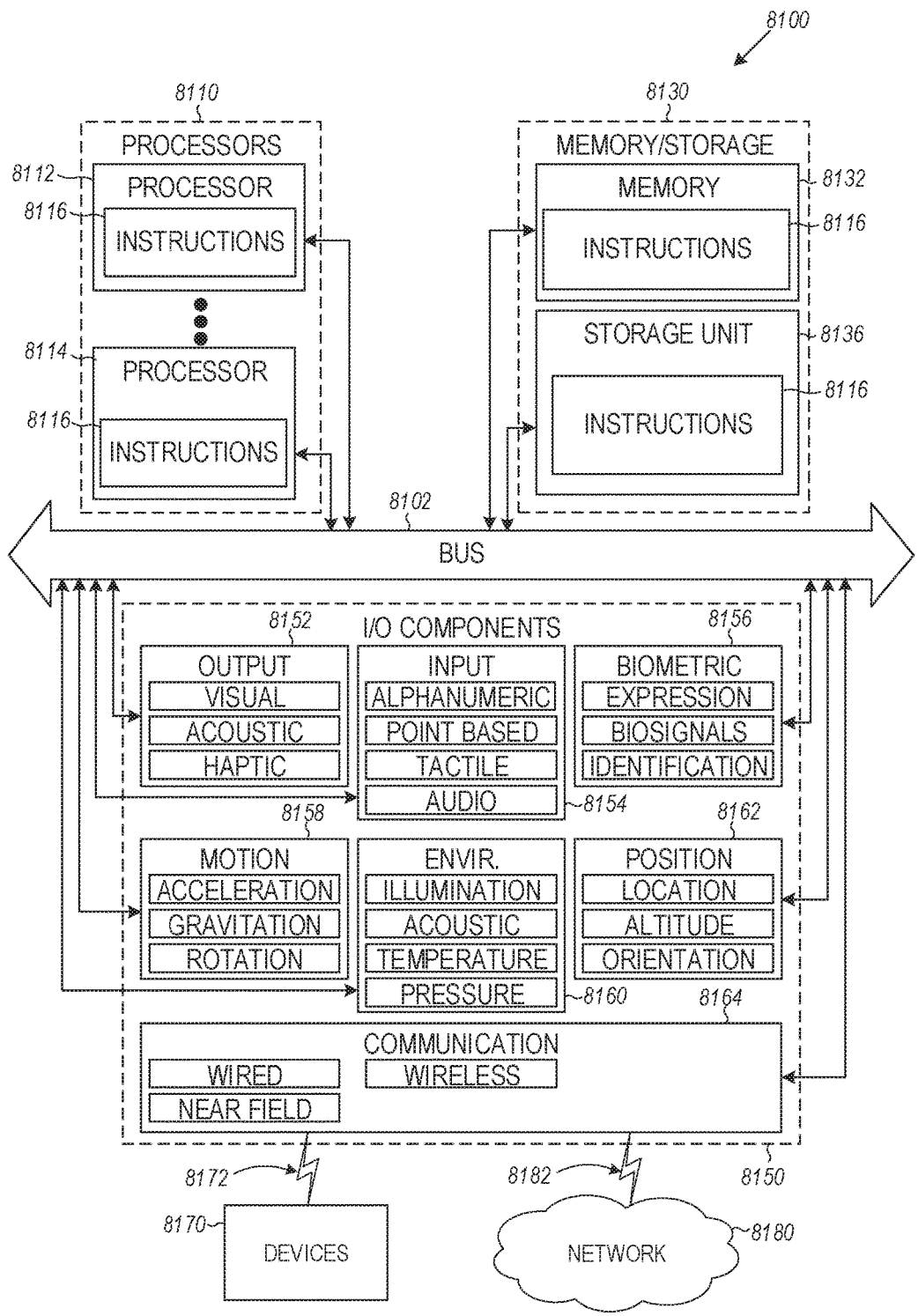
FIG. 81 illustrates a block diagram of an embodiment of a machine upon which one or more methods discussed herein can be performed or in conjunction with one or more systems or devices described herein may be used.

FIG. 81 illustrates, by way of example, a block diagram of an embodiment of a machine 8100 upon which one or more methods discussed herein can be performed or in conjunction with one or more systems or devices described herein may be used. FIG. 81 includes reference to structural components that are discussed and described in connection with several of the embodiments and figures above. In one or more examples, the implantable device 110, the source 102, the sensor 107, the processor circuitry 210, the digital controller 548, circuitry in the circuitry housing 606-606C, system control circuitry, power management circuitry, the controller, stimulation circuitry, energy harvest circuitry, synchronization circuitry, the external device, control circuitry, feedback control circuitry, the implanted device, location circuitry, control circuitry, other circuitry of the implantable device, and/or circuitry that is a part of or connected to the external source, can include one or more of the items of the machine 8100. The machine 8100, according to some example embodiments, is able to read instructions from a machine-readable medium (e.g., a machine-readable storage medium) and to perform any one or more of the methodologies, one or more operations of the methodologies, or one or more circuitry functions discussed herein, such as the methods described herein. For example, FIG. 81 shows a diagrammatic representation of the machine 8100 in the example form of a computer system, within which instructions 8116 (e.g., software, a program, an application, an applet, an app, or other executable code) for causing the machine 8100 to perform any one or more of the methodologies discussed herein can be executed. The instructions transform the general, non-programmed machine into a particular machine programmed to carry out the described and illustrated functions in the manner described. In alternative embodiments, the machine 8100 operates as a stand-alone device or can be coupled (e.g., networked) to other machines. In a networked deployment, the machine 8100 can operate in the capacity of a server machine or a client machine in a server-client network environment, or as a peer machine in a peer-to-peer (or distributed) network environment. Various portions of the machine 8100 can be included in, or used with, one or more of the external source 102 and the implantable device 110. In one or more examples, different instantiations or different physical hardware portions of the machine 8100 are separately implanted at the external source 102 and the implantable device 110.

In one or more examples, the machine 8100 can comprise, but is not limited to, a server computer, a client computer, a personal computer (PC), a tablet computer, a laptop computer, a cellular telephone, a smart phone, a mobile device, a wearable device (e.g., a smart watch), a smart home device (e.g., a smart appliance), other smart devices, a web appliance, a network router, a network switch, a network bridge, or any machine capable of executing the instructions 8116, sequentially or otherwise, that specify actions to be taken by machine 8100. Further, while only a single machine 8100 is illustrated, the term "machine" shall be taken to include a collection of machines 8100 that individually or jointly execute the instructions 8116 to perform any one or more of the methodologies discussed herein.

The machine 8100 can include processors 8110, memory 8130, or I/O components 8150, which can be configured to communicate with each other such as via a bus 8102. In one or more examples embodiment, the processors 8110 (e.g., a Central Processing Unit (CPU), a Reduced Instruction Set Computing (RISC) processor, a Complex Instruction Set Computing (CISC) processor, a Graphics Processing Unit (GPU), a Digital Signal Processor (DSP), an Application Specific Integrated Circuitry (ASIC), a Radio-Frequency Integrated Circuitry (RFIC), another processor, or any suitable combination thereof) can include, for example, processor 8112 and processor 8114 that can execute instructions 8116. The term "processor" is intended to include multi-core processors that can include two or more independent processors (sometimes referred to as "cores") that can execute instructions contemporaneously. Although FIG. 81 shows multiple processors, the machine 8100 can include a single processor with a single core, a single processor with multiple cores (e.g., a multi-core process), multiple processors with a single core, multiple processors with multiples cores, or any combination thereof.

The memory/storage 8130 can include a memory 8132, such as a main memory, or other memory storage, and a storage unit 8136, both accessible to the processors 8110 such as via the bus 8102. The storage unit 8136 and memory 8132 store the instructions 8116 embodying any one or more of the methodologies or functions described herein. The instructions 8116 can also reside, completely or partially, within the memory 8132, within the storage unit 8136, within at least one of the processors 8110 (e.g., within the processor's cache memory), or any suitable combination thereof, during execution thereof by the machine 8100. Accordingly, the memory 8132, the storage unit 8136, and the memory of processors 8110 are examples of machine-readable media.

As used herein, "machine-readable medium" means a device able to store instructions and data temporarily or permanently and can include, but is not be limited to, random-access memory (RAM), read-only memory (ROM), buffer memory, flash memory, optical media, magnetic media, cache memory, other types of storage (e.g., Erasable Programmable Read-Only Memory (EEPROM)) and/or any suitable combination thereof. The term "machine-readable medium" should be taken to include a single medium or multiple media (e.g., a centralized or distributed database, or associated caches and servers) able to store instructions 8116. The term "machine-readable medium" shall also be taken to include any medium, or combination of multiple media, that is capable of storing instructions (e.g., instructions 8116) for execution by a machine (e.g., machine 8100), such that the instructions, when executed by one or more processors of the machine 8100 (e.g., processors 8110), cause the machine 8100 to perform any one or more of the methodologies described herein. Accordingly, a "machine-readable medium" refers to a single storage apparatus or device, as well as "cloud-based" storage systems or storage networks that include multiple storage apparatus or devices. The term "machine-readable medium" excludes signals per se.

The I/O components 8150 can include a wide variety of components to receive input, provide output, produce output, transmit information, exchange information, capture measurements, and so on. The specific I/O components 8150 that are included in a particular machine will depend on the type of machine. For example, portable machines such as mobile phones will likely include a touch input device or other such input mechanisms, while a headless server machine will likely not include such a touch input device. It will be appreciated that the I/O components 8150 can include many other components that are not shown in FIG. 81. The I/O components 8150 are grouped according to functionality merely for simplifying the following discussion and the grouping is in no way limiting. In various example embodiments, the I/O components 8150 can include output components 8152 and input components 8154. The output components 8152 can include visual components (e.g., a display such as a plasma display panel (PDP), a light emitting diode (LED) display, a liquid crystal display (LCD), a projector, or a cathode ray tube (CRT)), acoustic components (e.g., speakers), haptic components (e.g., a vibratory motor, resistance mechanisms), other signal generators, and so forth. The input components 8154 can include alphanumeric input components (e.g., a keyboard, a touch screen configured to receive alphanumeric input, a photo-optical keyboard, or other alphanumeric input components), point based input components (e.g., a mouse, a touchpad, a trackball, a joystick, a motion sensor, or other pointing instrument), tactile input components (e.g., a physical button, a touch screen that provides location and/or force of touches or touch gestures, or other tactile input components), audio input components (e.g., a microphone), and the like.

In further example embodiments, the I/O components 8150 can include biometric components 8156, motion components 8158, environmental components 8160, or position components 8162 among a wide array of other components. For example, the biometric components 8156 can include components to detect expressions (e.g., hand expressions, facial expressions, vocal expressions, body gestures, or eye tracking), measure physiologic signals (e.g., blood pressure, heart rate, body temperature, perspiration, or brain waves, neural activity, or muscle activity), identify a person (e.g., voice identification, retinal identification, facial identification, fingerprint identification, or electroencephalogram based identification), and the like.

The motion components 8158 can include acceleration sensor components (e.g., accelerometer), gravitation sensor components, rotation sensor components (e.g., gyroscope), and so forth. In one or more examples, one or more of the motion components 8158 can be incorporated with the external source 102 or the implantable device 110, and can be configured to detect motion or a physical activity level of a patient. Information about the patient's motion can be used in various ways, for example, to adjust a signal transmission characteristic (e.g., amplitude, frequency, etc.) when a physical relationship between the external source 102 and the implantable device 110 changes or shifts.

The environmental components 8160 can include, for example, illumination sensor components (e.g., photometer), temperature sensor components (e.g., one or more thermometer that detect ambient temperature), humidity sensor components, pressure sensor components (e.g., barometer), acoustic sensor components (e.g., one or more microphones that detect background noise), proximity sensor components (e.g., infrared sensors that detect nearby objects), gas sensors (e.g., gas detection sensors to detection concentrations of hazardous gases for safety or to measure pollutants in the atmosphere), or other components that can provide indications, measurements, or signals corresponding to a surrounding physical environment. The position components 8162 can include location sensor components (e.g., a Global Position System (GPS) receiver component), altitude sensor components (e.g., altimeters or barometers that detect air pressure from which altitude can be derived), orientation sensor components (e.g., magnetometers), and the like. In one or more examples, the I/O component(s) 8150 can be a part of the implantable device 110 and/or the external source 102.

Communication can be implemented using a wide variety of technologies. The I/O components 8150 can include communication components 8164 operable to couple the machine 8100 to a network 8180 or devices 8170 via coupling 8182 and coupling 8172 respectively. For example, the communication components 8164 can include a network interface component or other suitable device to interface with the network 8180. In further examples, communication components 8164 can include wired communication components, wireless communication components, cellular communication components, Near Field (nearfield) Communication (NFC) components, midfield communication components, farfield communication components, and other communication components to provide communication via other modalities. The devices 8170 can be another machine or any of a wide variety of peripheral devices.

Moreover, the communication components 8164 can detect identifiers or include components operable to detect identifiers. For example, the communication components 8164 can include Radio Frequency Identification (RFID) tag reader components, NFC smart tag detection components, optical reader components (e.g., an optical sensor to detect one-dimensional bar codes such as Universal Product Code (UPC) bar code, multi-dimensional bar codes such as Quick Response (QR) code, Aztec code, Data Matrix, Dataglyph, MaxiCode, PDF417, Ultra Code. UCC RSS-2D bar code, and other optical codes), or acoustic detection components (e.g., microphones to identify tagged audio signals). In addition, a variety of information can be derived via the communication components 8164, such as, location via Internet Protocol (IP) geo-location, location via Wi-Fi® signal triangulation, location via detecting a NFC beacon signal that can indicate a particular location, and so forth.

In some embodiments, the systems comprise various features that are present as single features (as opposed to multiple features). For example, in one embodiment, the system includes a single external source and a single implantable device or stimulation device with a single antenna. Multiple features or components are provided in alternate embodiments.

In some embodiments, the system comprises one or more of the following: means for tissue stimulation (e.g., an implantable stimulation device), means for powering (e.g., a midfield powering device or midfield coupler), means for receiving (e.g., a receiver), means for transmitting (e.g., a transmitter), means for controlling (e.g., a processor or control unit), etc.

Although various general and specific embodiments are described herein, it will be evident that various modifications and changes can be made to these embodiments without departing from the broader spirit and scope of the present disclosure. Accordingly, the specification and drawings are to be regarded in an illustrative rather than a restrictive sense. The accompanying drawings that form a part of this application show, by way of illustration, and not of limitation, specific embodiments in which the subject matter can be practiced. The embodiments illustrated are described in sufficient detail to enable those skilled in the art to practice the teachings disclosed herein. Other embodiments can be used or derived therefrom, such that structural and logical substitutions and changes can be made without departing from the scope of this disclosure. This Detailed Description, therefore, is not to be taken in a limiting sense, and the scope of various embodiments is defined only by the appended claims, along with the full range of equivalents to which such claims are entitled. Specific embodiments or examples are illustrated and described herein, however, it should be appreciated that any arrangement calculated to achieve the same purpose can be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 kHz" includes "10 kHz." Terms or phrases preceded by a term such as "substantially" or "generally" include the recited term or phrase. For example, "substantially parallel" includes "parallel" and "generally cylindrical" includes cylindrical.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention(s) and embodiments should be determined with reference to the appended claims, along with the full scope of equivalents to which such claims are entitled.

What is claimed is:

1. An implantable system comprising an elongate structure configured for implantation in a patient body using a cannula, the system comprising:
    an elongate circuit board assembly including, in order along its lengthwise direction, a proximal portion, a first flexible portion, a central portion, a second flexible portion, and a distal portion; and
    a hermetic enclosure configured to enclose the elongate circuit board assembly, wherein the hermetic enclosure includes:
    a first end cap with a conductive first feedthrough coupled to a conductor on the proximal portion of the elongate circuit board assembly; and
    a second end cap with a conductive second feedthrough coupled to a conductor on the distal portion of the elongate circuit board assembly;
    wherein the first and second flexible portions have different length characteristics.

2. The implantable system of claim 1, further comprising an antenna coupled to the first feedthrough, and wherein the first flexible portion has a lesser length than the second flexible portion.

3. The implantable system of claim 1, further comprising at least one electrostimulation electrode coupled to the second feedthrough.

4. The implantable system of claim 1, further comprising multiple electrostimulation electrodes provided at different locations along the elongate structure, wherein the second end cap includes multiple conductive feedthroughs coupled to respective conductors on the distal portion of the elongate circuit board assembly, and wherein the multiple electrostimulation electrodes are coupled to respective ones of the multiple conductive feedthroughs.

5. The implantable system of claim 1, wherein the proximal, distal, and central portions of the elongate circuit board assembly are more rigid than the first and second flexible portions of the elongate circuit board assembly.

6. The implantable system of claim 5, wherein a rigidity of the proximal, distal, and central portion of the elongate circuit board assembly is due at least in part to a solder mask provided on the proximal, distal, and central portions.

7. The implantable system of claim 1, further comprising a welding or brazing material coupling the first and second end caps to the enclosure.

8. The implantable system of claim 1, wherein the proximal portion or the distal portion comprises solder bumps coupling the circuit board to the first or second end cap respectively.

9. The implantable system of claim 1, further comprising a dielectric filler on a portion of the elongate circuit board assembly inside the enclosure.

10. The implantable system of claim 1, wherein the conductor on the proximal portion of the elongate circuit board comprises a via coupled to the first feedthrough.

11. An implantable system comprising an elongate structure configured for implantation in a patient body using a cannula, the system comprising:
    an elongate circuit board assembly including, in order along its lengthwise direction, a proximal portion, a first flexible portion, and a distal portion; and a hermetic enclosure configured to enclose the elongate circuit board assembly, wherein the hermetic enclosure includes:
a first end cap with a conductive first feedthrough coupled to a conductor on the proximal portion of the elongate circuit board assembly; and
a second end cap with a conductive second feedthrough coupled to a conductor on the distal portion of the elongate circuit board assembly;
wherein the proximal and distal portions have different length characteristics.

12. The implantable system of claim 11, wherein the elongate circuit board assembly further includes a central portion and a second flexible portion interposed between the first flexible portion and the distal portion.

13. The implantable system of claim 12, further comprising an antenna coupled to the first feedthrough, and wherein the first flexible portion has a lesser length than the second flexible portion.

14. The implantable system of claim 11, further comprising at least one electrostimulation electrode coupled to the second feedthrough.

15. The implantable system of claim 11, further comprising multiple electrostimulation electrodes provided at different locations along the elongate structure, wherein the second end cap includes multiple conductive feedthroughs coupled to respective conductors on the distal portion of the elongate circuit board assembly, and wherein the multiple electrostimulation electrodes are coupled to respective ones of the multiple conductive feedthroughs.

16. The implantable system of claim 11, wherein the proximal and distal portions of the elongate circuit board assembly are more rigid than the first flexible portion of the elongate circuit board assembly.

17. The implantable system of claim 16, wherein a rigidity of the proximal and distal portions of the elongate circuit board assembly is due at least in part to a solder mask provided on the proximal and distal portions.

18. The implantable system of claim 11, wherein the conductor on the proximal portion of the elongate circuit board comprises a via coupled to the first feedthrough.

* * * * *